(12) United States Patent
Duan et al.

(10) Patent No.: US 8,324,401 B2
(45) Date of Patent: Dec. 4, 2012

(54) INDANE MODULATORS OF GLUCOCORTICOID RECEPTOR, AP-1, AND/OR NF-κB ACTIVITY AND USE THEREOF

(75) Inventors: Jingwu Duan, Yardley, PA (US); Bin Jiang, Norristown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 501 days.

(21) Appl. No.: 12/542,762

(22) Filed: Aug. 18, 2009

(65) Prior Publication Data

US 2009/0325961 A1 Dec. 31, 2009

Related U.S. Application Data

(62) Division of application No. 11/642,508, filed on Dec. 20, 2006, now Pat. No. 7,592,461.

(60) Provisional application No. 60/752,353, filed on Dec. 21, 2005.

(51) Int. Cl.
  *A61K 31/4164* (2006.01)
  *A61K 31/426* (2006.01)
  *C07D 233/54* (2006.01)

(52) U.S. Cl. ............ 548/338.1; 548/373.1; 514/396; 514/406; 514/448; 549/70; 564/148; 564/150; 558/411

(58) Field of Classification Search .................. None
See application file for complete search history.

(56) References Cited

U.S. PATENT DOCUMENTS

| | | | | |
|---|---|---|---|---|
| 3,565,897 | A * | 2/1971 | Heerdt et al. | 544/297 |
| 4,224,341 | A | 9/1980 | Bayssat et al. | |
| 4,873,241 | A * | 10/1989 | Napier et al. | 514/237.8 |
| 5,047,534 | A | 9/1991 | Peet et al. | |
| 5,362,878 | A | 11/1994 | Chang et al. | |
| 6,013,674 | A | 1/2000 | Morin, Jr. et al. | |
| 2003/0055093 | A1* | 3/2003 | Strobel et al. | 514/367 |
| 2004/0014992 | A1 | 1/2004 | Meltzer et al. | |
| 2004/0204368 | A1 | 10/2004 | Ohmoto et al. | |
| 2005/0085517 | A1 | 4/2005 | De Nanteuil et al. | |
| 2005/0209297 | A1 | 9/2005 | Sanner et al. | |

FOREIGN PATENT DOCUMENTS

| | | |
|---|---|---|
| BE | 641514 * | 6/1964 |
| DE | 38 27 253 | 3/1989 |
| EP | 0 310 745 | 4/1989 |
| EP | 0 418 071 | 3/1991 |
| EP | 0 945 438 | 9/1999 |
| GB | 2 292 558 | 2/1996 |
| WO | WO 92/03434 | 3/1992 |
| WO | WO 94/19349 | 9/1994 |
| WO | WO 96/20193 | 7/1996 |
| WO | WO 98/25907 | 6/1998 |
| WO | WO 99/14207 | 3/1999 |
| WO | WO 99/24416 | 5/1999 |
| WO | WO 99/27965 | 6/1999 |
| WO | WO 01/25190 | 4/2001 |
| WO | WO 02/070479 | 9/2002 |
| WO | WO 02/081443 | 10/2002 |
| WO | WO 02/099388 | 12/2002 |
| WO | WO 03/031410 | 4/2003 |
| WO | WO 03/035622 | 5/2003 |
| WO | WO-2004/087142 A1 * | 10/2004 |
| WO | WO 2004/096220 | 11/2004 |
| WO | WO 2005/103050 | 11/2005 |

OTHER PUBLICATIONS

Chemical Abstracts Registry No. 684212-99-5 indexed in the Registry file on STN CAS Online May 21, 2004.*
Ozols et al., CA 61:18056, 1964.*
Baldwin, Jr., A.S., "The transcription factor NF-κB and human disease", The Journal of Clinical Investigation, vol. 107, No. 1, pp. 3-6 (2001).
Burke, J.R., "Targeting IκB kinase for the treatment of inflammatory and other disorders", Current Opinion in Drug Discovery & Development, vol. 6, No. 5, pp. 720-728 (2003).
Caldenhoven, E. et al., "Negative Cross-Talk between RelA and the Glucocorticoid Receptor: A Possible Mechanism for the Antiinflammatory Action of Glucocorticoids", Molecular Endocrinology, vol. 9, No. 4, pp. 401-412 (1995).
Chakravarti, D. et al., "Role of CBP/P300 in nuclear receptor signalling", Nature, vol. 383, pp. 99-103 (1996).
Diamond, M.I. et al., "Transcription Factor Interactions: Selectors of Positive or Negative Regulation from a Single DNA Element", Science, vol. 249, pp. 1266-1272 (1990).
Fagerholm, V. et al., "Altered glucose homeostasis in $\alpha_{2A}$-adrenoceptor knockout mice", European Journal of Pharmacology, vol. 505, pp. 243-252 (2004).

(Continued)

*Primary Examiner* — Laura L. Stockton
(74) *Attorney, Agent, or Firm* — Burton Rodney; Laurelee A. Duncan

(57) ABSTRACT

Novel non-steroidal compounds are provided that are useful in treating diseases associated with modulation of the glucocorticoid receptor, AP-1, and/or NF-κB activity including obesity, diabetes, inflammatory and immune diseases having the structure of formula (I):

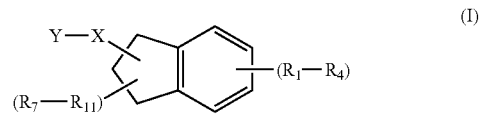

(I)

or enantiomers, diastereomers, or a pharmaceutically-acceptable salt, or hydrate, thereof, where X is $A_1QA_2$-; Q is a bond, —C(=O)—, —OC(O)—, —C(=O)$NR_5$—, —$SO_p$—, —$SO_pNR_5$—, —C(O)O—, —$NR_5C(O)$—, —OC(O)$NR_5$—, —$NR_5C(O)O$—, —S(O)$_pNR_5C(O)$—, —C(O)$NR_5S(O)_p$—, —$NR_5S(O)_p$—, or —$NR_5C(=O)NR_6$—. Y is selected from hydrogen, $C_{1-6}$alkyl, $OR_{16}$, substituted $C_{1-6}$alkyl, cycloalkyl, aryl, heterocyclo and heteroaryl. $A_1$ and $A_2$ are independently selected from a bond, $C_{1-3}$alkylene, or $C_{1-3}$alkenylene, and $R_1$-$R_{11}$ are defined herein. Also provided are pharmaceutical compositions, combinations, and methods of treating obesity, diabetes and inflammatory- or immune-associated diseases comprising said compounds.

10 Claims, No Drawings

OTHER PUBLICATIONS

Firestein, G.S. et al., "Signal Transduction and Transcription Factors in Rheumatic Disease", Arthritis & Rheumatism, vol. 42, No. 4, pp. 609-621 (1999).

Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).

Kamei, Y. et al., "A CBP Integrator Complex Mediates Transcriptional Activation and AP-1 Inhibition by Nuclear Receptors", Cell, vol. 85, pp. 403-414 (1996).

Manning, A.M., et al., "Targeting JNK for Therapeutic Benefit: from Junk to Gold?", Nature, vol. 2, pp. 554-565 (2003).

Miesfeld, R. et al., "Characterization of a steroid hormone receptor gene and mRNA in wild-type and mutant cells", Nature, vol. 312, pp. 779-781 (1984).

Peltz, G., "Transcription factors in immune-mediated disease", Current Opinion in Biotechnology, vol. 8, pp. 467-473 (1997).

Reichardt, H.M. et al., "DNA Binding of the Glucocorticoid Receptor is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Sato, N. et al., "Design and Synthesis of the Potent, Orally Available, Brain-Penetrable Arylpyrazole Class of Neuropeptide Y5 Receptor Antagonists", J. Med. Chem., vol. 46, No. 5, pp. 666-669 (2003).

Weinberger, C. et al., "Domain structure of human glucocorticoid receptor and its relationship to the v-*erb-A* oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

\* cited by examiner

US 8,324,401 B2

INDANE MODULATORS OF GLUCOCORTICOID RECEPTOR, AP-1, AND/OR NF-κB ACTIVITY AND USE THEREOF

This application is a divisional of U.S. patent application Ser. No. 11/642,508, filed Dec. 20, 2006, now U.S. Pat. No. 7,592,461, which claims priority benefit under Title 35 §119(e) of U.S. Provisional Application No. 60/752,353 filed Dec. 21, 2005, the content of which is incorporated herein by reference.

FIELD OF THE INVENTION

The present invention relates to new non-steroidal compounds which are effective modulators of the glucocorticoid receptor, AP-1, and/or NF-κB activity and thus are useful in treating diseases such as obesity, diabetes and inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A S, *Journal of Clin. Investigation*, 107, 3 (2001); Firestein, G. S., and Manning, A. M., *Arthritis and Rheumatism*, 42, 609 (1999); and Peltz, G., *Curr. Opin. in Biotech.* 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. and Davis, R. J., *Nature Rev. Drug Disc.*, V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK, BMS-345541, has been shown to be efficacious in animal models of inflammatory disease. See Burke, J. R., *Curr. Opin. Drug Discov. Devel.*, September; 6(5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228, 640-742, (1985); Weinberger et al., *Nature*, 318, 670-672 (1986) and for results in rats see Miesfeld, R., *Nature*, 312, 779-781, (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62, 1189 (1990); Yang-Yen, H. F. et al., *Cell*, 62, 1205 (1990); Diamond, M. I. et al., *Science* 249, 1266 (1990); and Caldenhoven, E. et al., *Mol. Endocrinol.*, 9, 401 (1995). Other mechanisms such as sequestration of co-activators by GR have also been proposed. See Kamer, Y. et al., *Cell*, 85, 403 (1996); and Chakravarti, D. et al., *Nature*, 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Tuckermann, J. et al., *Cell*, 93, 531 (1998) and Reichardt, H. M., *EMBO J.*, 20, 7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are which are effective modulators of the glucocorticoid receptor, AP-1, and/or NF-κB activity and thus are useful in treating diseases such as obesity, diabetes and inflammatory or immune associated diseases, and to a method for using such compounds to treat these and related diseases.

In accordance with the present invention, compounds are provided having the structure of formula (I)

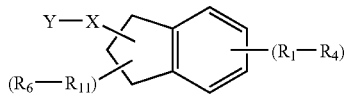

particularly compounds within the scope of formulae (IA) having the structure:

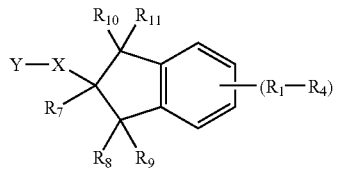

or an enantiomer, diastereomer, or a pharmaceutically-acceptable salt thereof, in which:

$R_1$, $R_2$, $R_3$, and $R_4$ are independently selected from (i) hydrogen, halogen, alkyl, substituted alkyl, alkenyl, substituted alkenyl, alkynyl, substituted alkynyl, nitro, azide, cyano, $OR_{12}$, $NR_{12}R_{13}$, —$(O)_t$—$C(=O)R_{12}$, —$(O)_t$—$CO_2R_{12}$, —(O), —$C(=O)NR_{12}R_{13}$, $NR_{12}C(=O)R_{13}$, $NR_{12}C(O)OR_{13}$, $NR_{12}C(S)OR_{13}$, $S(O)_pR_{18q}R_{18}$, $NR_{13}S(O)_pR_{18}$, $N(S(O)_pR_{18})_2$, $S(O)_pNR_{12}R_{13}$, cycloalkyl, heterocyclo, aryl, or heteroaryl; and/or (ii) together with the atoms to which they are attached one of $R_1$-$R_4$ is combined with another one of $R_1$-$R_4$ located on an adjacent carbon atom to form a fused ring; X is -$A_1QA_2$-;

Q is a bond, —$C(=O)$—, —$OC(O)$—, —$C(=O)NR_5$—, —$SO_p$—, —$SO_pNR_5$—, —$C(O)O$—, —$NR_5C(O)$—, —$OC(O)NR_5$—, —$NR_5C(O)O$—, —$S(O)_pNR_5C(O)$—, —$C(O)NR_5S(O)_p$— —$NR_5S(O)_p$—, or —$NR_5C(=O)NR_6$—;

$A_1$ and $A_2$ are independently selected from a bond, $C_{1-3}$alkylene, and $C_{1-3}$alkenylene;

$R_5$ and $R_{5a}$ are independently selected from hydrogen, alkyl, substituted alkyl, $C_{3-6}$cycloalkyl, $C_{3-6}$cycloalkenyl, heterocyclo, aryl, and heteroaryl;

$R_7$, $R_8$, $R_9$, $R_{10}$, and $R_{11}$ are independently selected from:

(i) hydrogen, halogen, alkyl, substituted alkyl, alkenyl, substituted alkenyl, alkynyl, substituted alkynyl, nitro, cyano, $OR_{14}$, $SR_{14}$, $NR_{14}R_{15}$, $C(=O)R_{14}$, $CO_2R_{14}$, $C(=O)NR_{14}R_{15}$, —O—$C(=O)R_{14}$, $NR_{14}C(=O)R_{15}$, $NR_{14}C(=O)OR_{15}$, $NR_{14}C(=S)OR_{15}$, $S(O)_pR_{19}$, $NR_{14}S(O)_pR_{19}$, $S(O)_pNR_{14}R_{15}$, cycloalkyl, cycloalkenyl, heterocyclo, aryl, and heteroaryl, provided that:

(a) if X is —$NR_5C(O)$— where Y is attached to the nitrogen atom, then $R_7$ is selected from a group other than $NR_{14}R_{15}$ or —$NR_{14}C(=O)R_{15}$; and/or (b) if X is —$NR_5C(O)$— where Y is attached to the nitrogen atom, then one or more of $R_7$, $R_8$, $R_9$, $R_{10}$, and/or $R_{11}$ is a heterocyclo, the heterocyclo is selected from a group other than maleimide; and/or (ii) $R_8$ and $R_9$, and/or $R_{10}$ and $R_{11}$ are taken together to form an oxo, alkenyl, substituted alkenyl or, together with the atom to which they are both attached $R_8$ and $R_9$, and/or $R_{10}$ and $R_{11}$ combine to form a spirocyclic group; and/or (iii) $R_7$ is taken together with one of $R_8$ or $R_{11}$ to form a double bond;

Y is selected from hydrogen, $C_{1-6}$alkyl, $OR_{16}$, substituted $C_{1-6}$alkyl, cycloalkyl, aryl, heterocyclo and heteroaryl; provided that if X is —$NR_5C(O)$— where Y is attached to the nitrogen atom, then Y is selected from a group other than pyridine, pyrimidine, pyridone or pyrazole substituted with a phenyl ring;

$R_{12}$, $R_{13}$, $R_{14}$, $R_{15}$, and $R_{16}$ at each occurrence are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) together with the atoms to which they are attached $R_{12}$ is combined with $R_{13}$ and/or $R_{14}$ is combined with $R_{15}$ to form a heteroaryl or heterocyclo ring;

$R_{18}$ and $R_{19}$ at each occurrence are independently selected from alkyl, substituted alkyl, alkenyl, substituted alkenyl, alkynyl, substituted alkynyl, cycloalkyl, cycloalkenyl, aryl, heteroaryl, and heterocyclo;

t at each occurrence is 0 or 1; and p at each occurrence is 1 or 2.

Preferred compounds within the scope of formulae (IA) above, including enantiomers, diastereomers, or a pharmaceutically-acceptable salt, or a hydrate, thereof, are those in which Q is a bond, —$C(=O)NR_5$—, —$NR_5(CO)$—, —$SO_pNR_5$—, —$NR_5C(=O)NR_6$, or —$SO_pNR_5$—

Also preferred compounds within the scope of formulae (IA) above, are those, including enantiomers, diastereomers, or a pharmaceutically-acceptable salt, or hydrate, thereof, in which Y is selected from (i) hydrogen, methyl, ethyl, hydroxy; or $CF_3$; or (ii) phenyl, thiazole, imidazole, thiadiazole, triazole, thiophene, indazole, imidazolinyl, pyrazole, tetrahydroimdazopyridine, imidazopyridine, thiazolopyridine, benzoimidazole, or benzothiazole, each ring of which is substituted, as valence allows, by one to three groups, $R_{20}$, $R_{21}$ and/or $R_{22}$;

$R_{20}$, $R_{21}$ and $R_{22}$ are independently selected from (i) hydrogen, halogen, alkyl, substituted alkyl, alkenyl, substituted alkenyl, alkynyl, substituted alkynyl, nitro, azide, cyano, oxo, =S, $OR_{23}$, $NR_{23}R_{24}$, —$(O)_t$—$C(=O)R_{23}$, —$(O)_t$—$CO_2R_{23}$, —$(O)_t$—$C(=O)NR_{23}R_{24}$, $NR_{24}C(=O)R_{23}$, $NR_{24}C(O)OR_{23}$, $NR_{24}C(S)OR_{23}$, $S(O)_pR_{25}$, $NR_{24}S(O)_pR_{25}$, $S(O)_pNR_{23}R_{24}$, cycloalkyl, heterocyclo, aryl, and heteroaryl, wherein t is 0 or 1; and/or (ii) together with the atoms to which they are attached $R_{21}$ combines with $R_{22}$ to form a fused ring (Preferably $R_{21}$ and $R_{22}$ are independently selected from hydrogen, $C_{1-6}$alkyl, substituted $C_{1-6}$alkyl, halogen, oxo, =S, amino, phenyl, substituted phenyl, napthyl, and substituted napthyl.);

$R_{23}$ and $R_{24}$ at each occurrence are independently selected from (i) hydrogen, alkyl, alkenyl, alkynyl, $C_{3-7}$cycloalkyl, cycloalkenyl, aryl, a 4- to 7-membered heteroaryl, and a 5- to 7-membered heteroaryl heterocyclo; or (ii) together with the atoms to which they are attached $R_{23}$ is combined with $R_{24}$ to form a heteroaryl or heterocyclo ring, wherein each $R_{23}$ and $R_{24}$, except hydrogen is optionally substituted further with one to three substituents selected from $R_{26}$; and $R_{25}$ is selected from alkyl, substituted alkyl, alkenyl, substituted alkenyl, alkynyl, substituted alkynyl, cycloalkyl, cycloalkenyl, aryl, heteroaryl, and heterocyclo, wherein each $R_{25}$ is optionally substituted further with one to three substituents selected from $R_{26}$; and $R_{26}$ is selected from $(C_{1-6})$alkyl, $(C_{2-6})$alkenyl, hydroxy, halogen, cyano, nitro, $CF_3$, $O(C_{1-6}$alkyl), $OCF_3$, $C(=O)H$, $C(=O)(C_{1-6}$alkyl), $CO_2H$, $CO_2(C_{1-6}$alkyl), $NHCO_2(C_{1-6}$ alkyl), —S($C_{1-6}$alkyl), —$NH_2$, NH($C_{1-6}$alkyl), N($C_{1-6}$alkyl)$_2$, N($CH_3$)$_3^+$, $SO_2$($C_{1-6}$alkyl), C(=O)($C_{1-4}$alkylene)$NH_2$, C(=O)($C_{1-4}$alkylene)NH(alkyl), C(=O)($C_{1-4}$alkylene)N($C_{1-4}$alkyl)$_2$, $C_{3-7}$cycloalkyl, phenyl, benzyl, phenylethyl, phenyloxy, benzyloxy, napthyl, a four- to seven-membered heterocylo, and a five to six membered heteroaryl.

More preferred compounds are those in which Y is a ring as described above, that is substituted, as valence allows, by one to three groups, $R_{20}$, $R_{21}$ and/or $R_{22}$ selected from hydrogen, $C_{1-6}$alkyl, substituted $C_{1-6}$alkyl, halogen, oxo, thio, amino, phenyl, substituted phenyl, napthyl, and substituted napthyl. Particularly preferred are those compounds in which in which Y is selected from a fused or unfused five-membered heteroaryl or heterocyclo ring having at least one heteroatom selected from N, O or S, wherein said ring is substituted by one to three groups, $R_{20}$, $R_{21}$ and/or $R_{22}$, selected from hydrogen, $C_{1-6}$alkyl, substituted $C_{1-6}$alkyl, halogen, oxo, thio, amino, phenyl, substituted phenyl, napthyl, and substituted napthyl.

Other preferred compounds within the scope of formulae (IA) above, or enantiomers, diastereomers, or a pharmaceutically-acceptable salt, or a hydrate, thereof, are those in which $A_1$ and $A_2$ are independently a bond or $C_{1-3}$alkylene substituted with hydrogen, halogen, cyano, nitro, or hydroxy. Particularly preferred are compounds where $A_1$ and $A_2$ are independently a bond, methylene, or methylene substituted with hydroxy or fluoro. Even more particularly preferred are compounds where both $A_1$ and $A_2$ are each a bond.

Also preferred compounds within the scope of formulae (IA) above, are those, including enantiomers, diastereomers, or a pharmaceutically-acceptable salt, or hydrate, thereof, in which $R_7$ is selected from: (i) halogen, alkyl, substituted alkyl, alkenyl, substituted alkenyl, alkynyl, substituted alkynyl, nitro, cyano, $OR_{14}$, $SR_{14}$, $NR_{14}R_{15}$, C(=O)$R_{14}$, $CO_2R_{14}$, C(=O)$NR_{14}R_{15}$, —O—C(=O)$R_{14}$, $NR_{14}$C(=O)$R_{15}$, $NR_{14}$C(=O)$OR_{15}$, $NR_{14}$C(=S)$OR_{15}$, $NR_{14}$S(O)$_pR_{19}$, S(O)$_pNR_{14}R_{15}$, cycloalkyl, cycloalkenyl, heterocyclo, aryl, and heteroaryl; and/or (ii) $R_7$ is taken together with one of $R_8$ or $R_{11}$ to form a double bond. More preferred compounds within this scope are those in which $R_8$, $R_9$ $R_{10}$, and $R_{11}$ are independently hydrogen, hydroxy, cyano, nitro, $C_{1-6}$alkyl, substituted $C_{1-6}$alkyl, a five- to six-membered heteroaryl, a five- to six-membered heterocyclo, or aryl; $R_7$ is hydroxy, cyano, nitro, $C_{1-6}$alkyl, substituted $C_{1-6}$alkyl, a five- to six-membered heteroaryl, a five- to six-membered heterocyclo, or aryl; or where possible $R_8$ and $R_9$, and/or $R_{10}$ and $R_{11}$ are taken together to form oxo, or together with the atom to which they are both attached $R_8$ and $R_9$, and/or $R_{10}$ and $R_{11}$ combine to form a spiro cycloalkenyl ring. Particularly preferred compounds are those in which $R_7$ is $C_{1-4}$alkyl; $R_8$ and $R_9$ are independently selected from (i) hydrogen and $C_{1-6}$alkyl; and (ii) phenyl, benzyl, a five-membered heterocyclo, and a five-membered heteroaryl, each ring of which is optionally substituted with one to two groups selected from hydroxy, cyano, halogen, —O$C_{1-6}$alkyl (e.g. methoxy), and $C_{1-6}$alkyl; and $R_{10}$ and $R_{11}$, are both hydrogen.

Preferred compounds within the scope of formulae (IA) above, are those, including enantiomers, diastereomers, or a pharmaceutically-acceptable salt, or hydrate, thereof, in which $R_1$, $R_2$, $R_3$, and $R_4$ are independently (i) hydrogen, halogen, cyano, nitro, $C_{1-6}$alkyl, substituted $C_{1-6}$alkyl, $CF_3$, CHO, $C_{2-4}$alkenyl, $C_{2-4}$alkynyl, —O($C_{1-6}$alkyl), hydroxy, —OC(O)O($C_{1-6}$alkyl), —OC(O)$NH_{0-2}$($C_{1-6}$alkyl)$_{2-0}$, OC(O)($C_{1-6}$alkyl), C(O)$_2$H, C(O)$C_{1-6}$alkyl, C(O)$NH_{0-2}$($C_{1-6}$alkyl)$_{2-0}$, —(CH$_2$)$_{0-3}$$NH_{0-2}$($C_{1-6}$alkyl)$_{2-0}$, NHC(O)$C_{1-6}$alkyl, NS(O)$_2C_{1-6}$alkyl, NHC(O)O$C_{1-6}$alkyl, phenoxy, benzyloxy, phenyl acetylene, trimethylsilyl acetylene, $C_{3-6}$cycloalkyl, aryl (such as phenyl) or a five- to six membered heterocyclo or heteroaryl ring (e.g. pyrrole, tetrazole, imidazole, pyrazole, piperidine, pyridine, morpholine), each containing at least one N atom.

Yet other preferred compounds within the scope of formulae (IA) above, are those, including enantiomers, diastereomers, or a pharmaceutically-acceptable salt, or a hydrate, thereof, wherein X is —NR$_5$C(O)—. More preferably Y is attached to the nitrogen atom. More preferred compounds within this scope are those wherein:

Y is selected from (i) hydrogen, methyl, ethyl, hydroxy; or $CF_3$; or (ii) phenyl, thiazole, imidazole, thiadiazole, triazole, thiophene, indazole, imidazolinyl, pyrazole, tetrahydroimdazopyridine, imidazopyridine, thiazolopyridine, benzoimidazole, or benzothiazole, each ring of which is substituted, as valence allows, by one to three groups, $R_{20}$, $R_{21}$ and/or $R_{22}$;

$R_{20}$, $R_{21}$ and $R_{22}$ are independently selected from (i) hydrogen, halogen, alkyl, substituted alkyl, alkenyl, substituted alkenyl, alkynyl, substituted alkynyl, nitro, azide, cyano, oxo, =S, $OR_{23}$, $NR_{23}R_{24}$, —(O), —C(=O)$R_{23}$, —(O), —$CO_2R_{23}$, —(O), —C(=O)$NR_{23}R_{24}$, $NR_{24}$C(=O)$R_{23}$, $NR_{24}$C(O)$OR_{23}$, $NR_{24}$C(S)$OR_{23}$, S(O)$_pR_{25}$, $NR_{24}$S(O)$_pR_{25}$, S(O)$_pNR_{23}R_{24}$, cycloalkyl, heterocyclo, aryl, and heteroaryl, wherein t is 0 or 1; and/or (ii) together with the atoms to which they are attached $R_{21}$ combines with $R_{22}$ to form a fused ring (Preferably $R_{21}$ and $R_{22}$ are independently selected from hydrogen, $C_{1-6}$alkyl, substituted $C_{1-6}$alkyl, halogen, oxo, =S, amino, phenyl, substituted phenyl, napthyl, and substituted napthyl.);

$R_{23}$ and $R_{24}$ at each occurrence are independently selected from (i) hydrogen, alkyl, alkenyl, alkynyl, $C_{3-7}$cycloalkyl, cycloalkenyl, aryl, a 4- to 7-membered heteroaryl, and a 5- to 7-membered heteroaryl heterocyclo; or (ii) together with the atoms to which they are attached $R_{23}$ is combined with $R_{24}$ to form a heteroaryl or heterocyclo ring, wherein each $R_{23}$ and $R_{24}$, except hydrogen is optionally substituted further with one to three substituents selected from $R_{26}$; and $R_{25}$ is selected from alkyl, substituted alkyl, alkenyl, substituted alkenyl, alkynyl, substituted alkynyl, cycloalkyl, cycloalkenyl, aryl, heteroaryl, and heterocyclo, wherein each $R_{25}$ is optionally substituted further with one to three substituents selected from $R_{26}$; and $R_{26}$ is selected from ($C_{1-6}$)alkyl, ($C_{2-6}$)alkenyl, hydroxy, halogen, cyano, nitro, $CF_3$, O($C_{1-6}$alkyl), $OCF_3$, C(=O)H, C(=O)($C_{1-6}$alkyl), $CO_2H$, $CO_2$($C_{1-6}$alkyl), $NHCO_2$($C_{1-6}$alkyl), —S($C_{1-6}$alkyl), —$NH_2$, NH($C_{1-6}$alkyl), N($C_{1-6}$alkyl)$_2$, N($CH_3$)$_3^+$, $SO_2$($C_{1-6}$alkyl), C(=O)($C_{1-4}$alkylene)$NH_2$, C(=O)($C_{1-4}$alkylene)NH(alkyl), C(=O)($C_{1-4}$alkylene)N($C_{1-4}$alkyl)$_2$, $C_{3-7}$cycloalkyl, phenyl, benzyl, phenylethyl, phenyloxy, benzyloxy, napthyl, a four- to seven-membered heterocylo, and a five to six membered heteroaryl.

More preferred groups, $R_{20}$, $R_{21}$ and/or $R_{22}$ include groups in which the ring is substituted, as valence allows, from one to three groups selected from hydrogen, $C_{1-6}$alkyl, substituted $C_{1-6}$alkyl, halogen, oxo, thio, amino, phenyl, substituted phenyl, napthyl, and substituted napthyl. Particularly preferred are those compounds in which in which Y is selected from a fused or unfused five-membered heteroaryl or heterocyclo ring having at least one heteroatom selected from N, O or S.

Even more preferred compounds within the scope of formulae (IA), particularly within the scope of compounds described in paragraphs [0016] and [0020], including enantiomers, diastereomers, or a pharmaceutically-acceptable salt, or a hydrate, thereof, are those wherein:

Y is

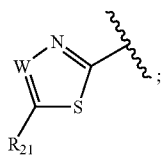

W is $CR_{22}$ or N.

Particularly preferred compounds are those having the formula (IC)

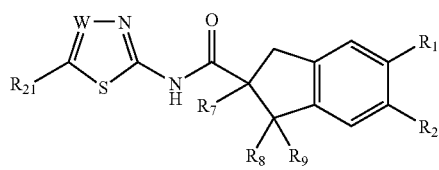

or an enantiomer, diastereomer, a pharmaceutically-acceptable salt, or a hydrate, thereof, wherein:

$R_1$ and $R_2$ are independently hydrogen, halogen, cyano, nitro, $NH_2$, $C_{1-6}$alkyl, $CF_3$, —$(CH_2)_{0-10}OH$, —$CH(OH)C_{1-6}$alkyl, $CH(OH)C_{1-6}$aryl, CHO, $C_{2-4}$alkenyl, $C_{2-4}$alkynyl, —$O(C_{1-6}$alkyl), —$OC(O)O(C_{1-6}$alkyl), —$OC(O)NH_{0-1}(C_{1-6}$alkyl)$_{2-0}$, —$OC(O)(C_{1-6}$alkyl), —$CO_2H$, —$C(O)C_{1-6}$alkyl, —$C(O)NH_{0-2}(C_{1-6}$alkyl)$_{2-0}$, —$(CH_2)_{0-3}NH_{0-2}(C_{1-6}$alkyl)$_{2-0}$, —$NHC(O)C_{1-6}$alkyl, —$NHS(O)_2C_{1-6}$alkyl, —$N(S(O)_2C_{1-6}$alkyl)$_2$, —$NHC(O)OC_{1-6}$alkyl, phenoxy, benzyloxy, phenyl acetylenyl, trimethylsilyl acetylenyl, $C_{3-6}$cycloalkyl, a five- to six membered heterocyclo containing at least one N atom, or a five- to six membered heteroaryl containing at least one N atom (more preferably $R_1$ and $R_2$ are independently, (i) hydrogen, methyl, ethyl, propyl, cyclopropyl, methoxy, phenoxy, hydroxymethyl, —$CH_2NMe_2$, —$CH_2NHMe$, —$CH(OH)Me$, —$NH$(PMB), —$CH(OH)$phenyl, hydroxy, iodo, bromo, chloro, cyano, $NH_2$, $NMe_2$, —$NHS(O)_2Me$, —$N(S(O)_2Me)_2$, —$NHCO_2Me$, —$CO_2H$, —$CONH_2$, —$NHC(O)Me$, —$C(O)CH_3$, —$OC(O)OMe$, —$O(C(O)NHMe$, —$OC(O)NMe_2$, —$OC(O)Me$, —$OC(O)OMe$, —CHO, tetrazolyl, imidazolyl, pyrazolyl, (substituted with hydrogen and methyl), piperidinyl, morpholinyl, cyclopropyl, 1- and 3-propenyl, 2-phenylethenylenyl, 2-phenylethylenyl, phenylacetylenyl, pyridinyl, (trimethylsilyl)acetylenyl, acetylenyl, ethenyl, 1-propynyl, or phenyl substituted with $C(O)N(CH_3)_2$ or (ii) together with the atoms to which they are attached $R_1$ and $R_2$ are combined to form a fused dioxo ring);

$R_7$ is $C_{1-4}$alkyl (more preferably methyl);

$R_8$ and $R_9$ are independently selected from
(i) hydrogen and $C_{1-6}$alkyl; and
(ii) phenyl, benzyl, a five-membered heterocyclo, and a five-membered heteroaryl, each ring optionally substituted with one to two groups selected from hydroxy, cyano, halogen, —$OC_{1-6}$alkyl (e.g. methoxy), and $C_{1-6}$alkyl; and $R_{21}$ and $R_{22}$ are independently hydrogen, $C_{1-6}$alkyl, $CF_3$, or aryl (more preferably $R_{21}$ and $R_{22}$ are independently (i) hydrogen, methyl, ethyl, or $CF_3$; (ii) substituted methylene (more preferably, methylene substituted by optionally substituted phenyl, particularly 4-((4-pyridinyl)phenyl)methyl), or 4-((4-(methyloxy)phenyl)methyl)); or (iii) napthyl or phenyl, each of which is optionally substituted by halogen, or —$OC_{1-4}$alkyl; or CONH(optionally substituted phenyl), (more particularly napthyl or phenyl is 4-halogen (particularly fluoro)-1-naphthalenyl, or 3-(((3-chloro-4-(methyloxy)phenyl)amino)carbonyl)phenyl)).

Other preferred compounds within the scope of formulae (IA) above, are those, including enantiomers, diastereomers, or a pharmaceutically-acceptable salt, or a hydrate, thereof, wherein Q is a bond, —NHC(O)NH—, —$NHC(O)_2$—, —$SO_2NHC(O)$—; —$SO_2NH$—, or —C(O)NH—. Particularly preferred compounds within this scope are those in which $A_1$ and $A_2$ are independently a bond, methylene, or methylene substituted with hydroxy or fluoro; and Y is
(i) hydrogen, methyl, ethyl, or $CF_3$; or
(ii) a phenyl, thiophene, thiazole, thiadiazole, triazole, imidazoline, imidazopyridine, or benzothiazole ring, of which is substituted, as valence allows, from one to two groups selected from hydrogen, oxo, amino, =S, and $C_{1-6}$ alkyl.

In particular, where Q is —$SO_2NHC(O)$— having the sulfur atom attached to Y, $A_1$ and $A_2$ are each a bond, and Y is methyl or phenyl; where Q is —$SO_2NH$— having the sulfur atom attached to Y, $A_1$ and $A_2$ are each a bond, and Y is methyl; where Q is a bond, $A_1$ is a bond, $A_2$ is methylene or CH(OH)—, and Y is thiophene, thiazole, thiadiazole, triazole, imdazoline, imdazopyridine, or benzothiazole ring, each of which is substituted, as valence allows, from one to two groups selected from hydrogen, oxo, $NH_2$, =S, methyl, and ethyl; where Q is —NHC(O)NH—, $A_1$ and $A_2$ are each a bond, and Y is methyl and phenyl; where Q is —$NC(O)_2$— having the nitrogen atom attached to Y, $A_1$ is methylene and $A_2$ is a bond, and Y is phenyl; and where Q is —C(O)NH— having the carbon atom attached to Y, $A_1$ is methylene or —$CF_2$—; $A_2$ is a bond, Y is methyl, ethyl, $CF_3$, thiophene, thiazole, and thiadiazole.

All aspects of the preferred compounds, for example, the individual variable definitions, may be combined with aspects of other preferred compounds to form other preferred compounds.

In another embodiment of the present invention, there is provided pharmaceutical compositions useful in treating endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease (e.g. diabetes) as well as other uses as described herein, which includes a therapeutically effective amount (depending upon use) of a compound of formula (I) of the invention and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, that is a disease associated with the expression product of a gene whose transcription is stimulated or repressed by glucocorticoid receptors, or a disease associated with AP-1- and/or NFκB-induced transcription, or a disease associated with AP-1 and/or NFκB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ

(particularly AP-1), such as inflammatory and immune disorders, cancer and tumor disorders, such as solid tumors, lymphomas and leukemia, and fungal infections such as mycosis fungoides.

Inflammatory or autoimmune diseases that may be treated can be selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, Type I and Type II diabetes, juvenile diabetes, obesity, asthma, inflammatory bowel disease, Crohn's disease, ulcerative colitis, pyoderma gangrenum, systemic lupus erythematosis, myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, viteligo, alopecia areata, autoimmune alopecia, autoimmune hypopituatarism, Guillain-Barre syndrome, and alveolitis; contact hypersensitivity, delayed-type hypersensitivity, contact dermatitis, uticaria, skin allergies, respiratory allergies, hayfever, allergic rhinitis and gluten-sensitive enteropathy, osteoarthritis, acute pancreatis, chronic pancreatitis, acute respiratory distress syndrome, Sezary's syndrome, restenosis, stenosis and artherosclerosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, psoriasis, seborrheic dermatitis, seasonal or perennial allergic rhinitis, bronchial asthma, contact dermatitis, atopic dermatitis, drug hypersensitivity reactions, allergic conjuncivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, ulcerative colitis, regional enteritis, Crohn's disease, Sjogren's syndrome, autoimmune vasculitis, multiple sclerosis, myasthenia gravis, sepsis, and chronic obstructive pulmonary disease. The treatment of diseases or disorders selected from transplant rejection, rheumatoid arthritis, psoriatic arthritis, multiple sclerosis, Type I diabetes, asthma, inflammatory bowel disease, systemic lupus erythematosis, psoriasis and chronic pulmonary disease are preferred.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary adrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta. These terms, as used herein, refer to glucocorticoid receptor from any source, including but not limited to: human glucocorticoid receptor as disclosed in Weinberger, et al. *Science* 228, p 640-742 (1985), and in Weinberger, et al. *Nature*, 318, p 670-672 (1986); rat glucocorticoid receptor as disclosed in Miesfeld, R. *Nature*, 312, p 779-781 (1985); mouse glucocortoid receptor as disclosed in Danielson, M. et al. *EMBO J.*, 5, 2513; sheep glucocorticoid receptor as disclosed in Yang, K., et al. *J. Mol. Endocrinol.* 8, p 173-180 (1992); marmoset glucocortoid receptor as disclosed in Brandon, D. D., et al, *J. Mol. Endocrinol.* 7, p 89-96 (1991); and human GR-beta as disclosed in Hollenberg, S M. et al. *Nature*, 318, p 635, 1985, Bamberger, C. M. et al. *J Clin Invest.* 95, p 2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, sepsis. Preferred methods include the treatment of transplant rejection, rheumatoid arthritis, psoriatic arthritis, multiple sclerosis, Type 1 diabetes, asthma, inflammatory bowel disease, systemic lupus erythematosis, psoriasis and chronic pulmonary disease.

In addition, in accordance with the present invention a method of treating a disease associated with AP-1-induced and/or NF-κB-induced transcription (particularly AP-1-induced transcription) is provided wherein a compound of formula (I) of the invention is administered to a patient at risk of developing the disease in a therapeutically effective amount to induce NHR transrepression of the AP-1-induced and/or NF-κB-induced transcription (particularly AP-1-induced transcription), thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, psoriatic arthritis, multiple sclerosis, Type 1 diabetes, asthma, inflammatory bowel disease, systemic lupus erythematosis, psoriasis and chronic pulmonary disease.

METHODS OF SYNTHESIS

The compounds of the present invention may be synthesized by many methods available to those skilled in the art of organic chemistry. General synthetic schemes, in accordance with the present invention, for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

Scheme 1 outlines a general synthesis for a series of indan-2-ylactamides. A number of 1,3-indanediones 1 are commercially available or can be readily prepared. Reaction of 1 with t-butyl bromoacetate in the presence of $K_2CO_3$ in DMSO gives acid 2 after hydrolysis with trifluoroacetic acid. The acid 2 can be coupled with a large variety of amines 3 using well-known peptide coupling conditions such as hydroxybenzotriazole (HOBt) and a carbodiimide such as EDC to give 1,3-dioxoindan-2-ylactamides 4. Alternatively, the diketo moiety in 2 can be reduced under typical hydrogenation conditions to give indan-2-ylacetic acid 5, which is converted to amide 6 under the previously discussed peptide coupling conditions.

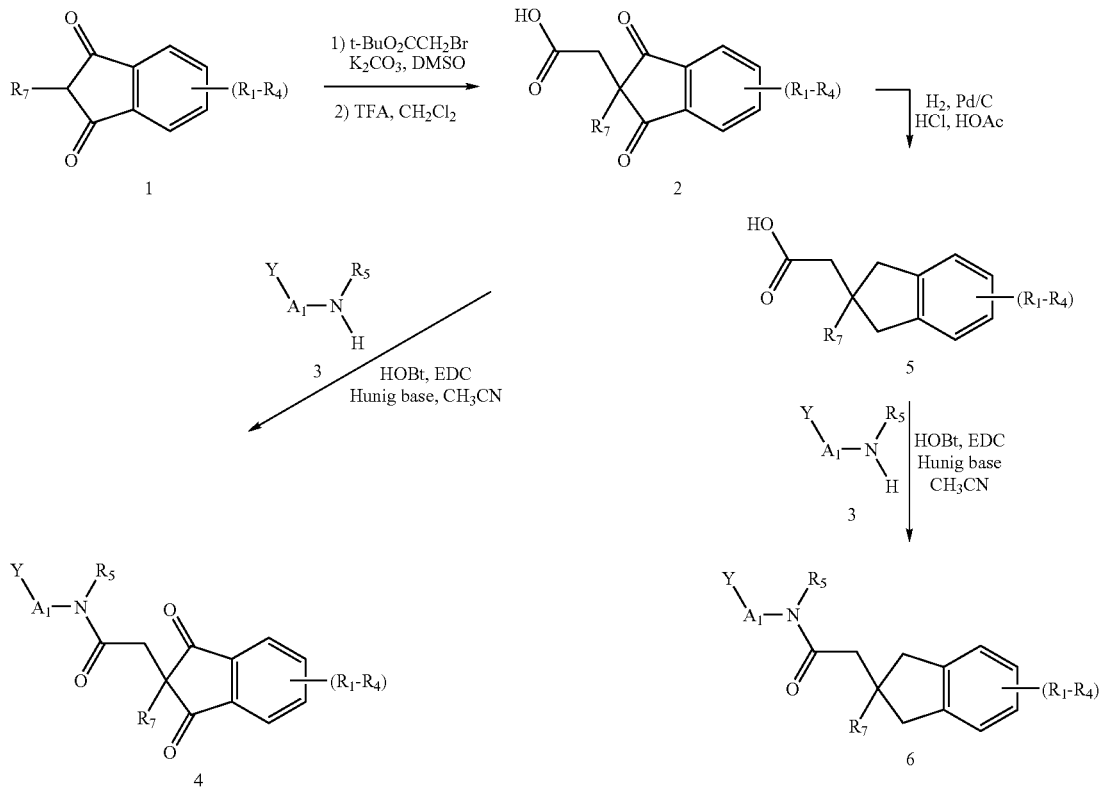

SCHEME 1

Scheme 2 outlines a general synthesis for a series of 2-substituted indane-2-carboxamides. Reaction of the enolate of indanecarboxylate 7 with R$_7$-LG, where LG is an appropriate leaving group such as chloro, bromo or iodo, gives neopentyl ester 8. After saponification with NaOH and coupling with amine 3 using previously described conditions, the desired product 10 can be obtained.

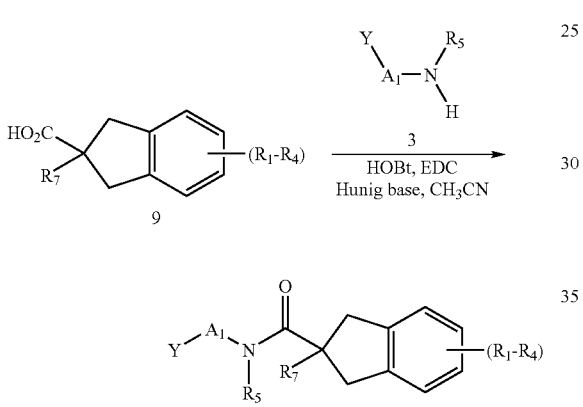

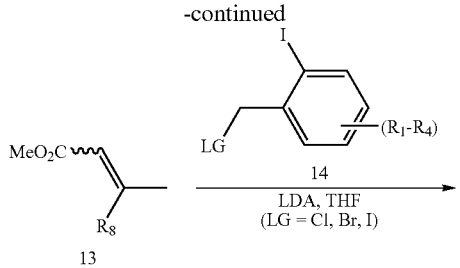

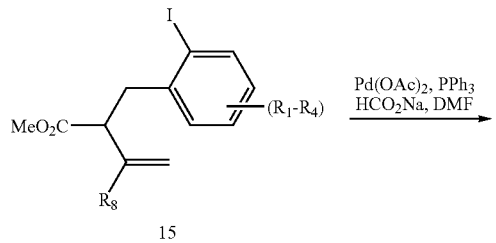

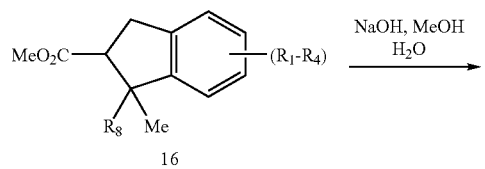

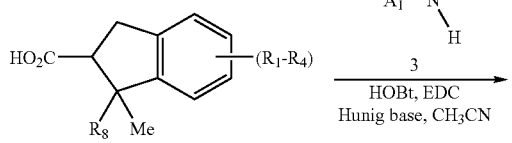

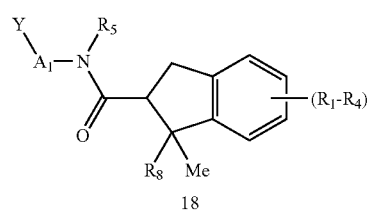

Scheme 3 outlines a general synthesis for a series of 1,1-di-substituted indane-2-carboxamides. Horner-Emmons reaction of methyl diethylphosphonoacetate (11) with methyl ketone 12 using sodium hydride as base gives enoate 13, normally as a mixture of cis and trans isomers. The geometry of the olefin is inconsequential. Treatment of the mixture with LDA generates a dienoate, which is reacted with an appropriate 2-iodobenzyl halide 14 to regioselectively give β,γ,-unsaturated ester 15. Using conditions reported by Beckwith and Gerba, compound 15 can be converted to indane 16 by treatment with Pd(OAc)$_2$, PPh$_3$ and sodium formate. See Beckwith and Gerba, *Aust. J. Chem.* 1992, Vol. 45 at 289 (1992). From 16, compound 18 is prepared following the saponification and coupling sequence described previously.

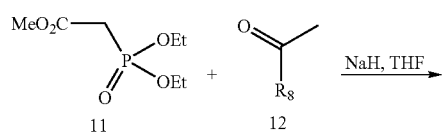

Scheme 4 outlines a general synthesis for a series of 1,2-di-substituted indane-2-carboxamides. Starting from indanone 19, sequential reaction of its enolate (generated with LDA) with R$_7$-LG (LG=halide) and methyl cyanoformate can stereoselectively give the trans product 20. Reaction of 20 with the aluminum amide of 3, generated by reaction with trimethylaluminum in situ, gives the desired amide product 21. The benzylic ketone in 20 can be reduced with triethylsilane and trifluoroacetic acid to give 22. Ester 22 can be converted to amide 23 using the previously described saponification and coupling sequence or the one-step trimethylaluminum condition. By reversing the reaction sequence of R$_7$-LG and methyl cyanoformate, cis-indanone 24 can be obtained stereoselectively from 19. Following analogous chemistry, compound 24 can be converted to the cis-isomers of 21 and 23.

SCHEME 4

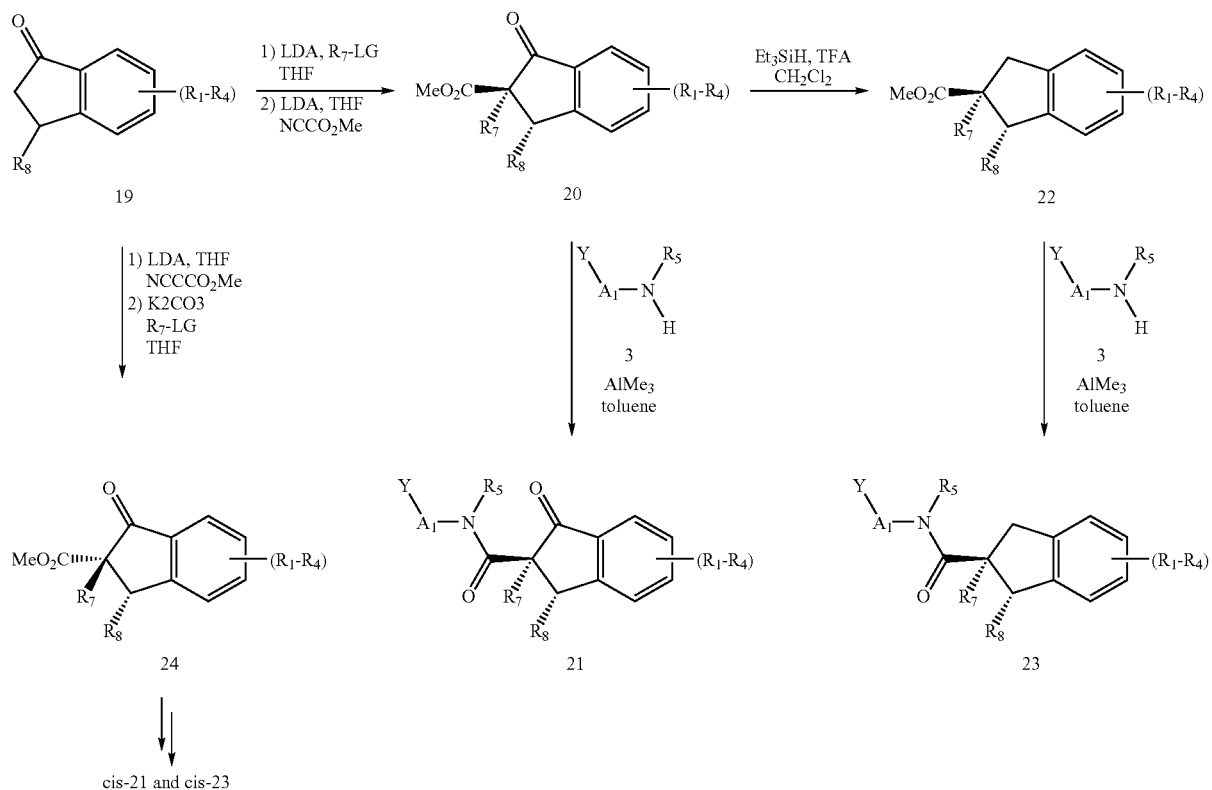

Scheme 5 outlines an alternative synthesis for a series of 1,2-di-substituted indane-2-carboxamides. Knoevenagel reaction of β-ketoester 25 with an aldehyde ($R_8$—CHO), using piperidine and acetic acid as catalysts, gives ester 26. Nazarov cyclization of 26 is accomplished with $AlCl_3$ in nitroethane at elevated temperature, to give indanone 27. Alkylation of ketoester 27 can be effected with mild bases such as $K_2CO_3$ and alkylating agents $R_7$-LG, where the leaving group (LG) is a chloride, bromide, iodide or sulfonate. Reduction of the ketone carbonyl can be achieved using triethylsilane in the presence of boron trifluoride etherate, to give 29. Saponification of the hindered ester 29 can be sluggish under the standard NaOH/MeOH/$H_2O$ at reflux conditions. Addition of DMSO to this mixture usually accelerates the reaction. Coupling of the acid product 30 with amine 3 proceeds under previously described coupling conditions to complete the synthesis of 31.

SCHEME 5

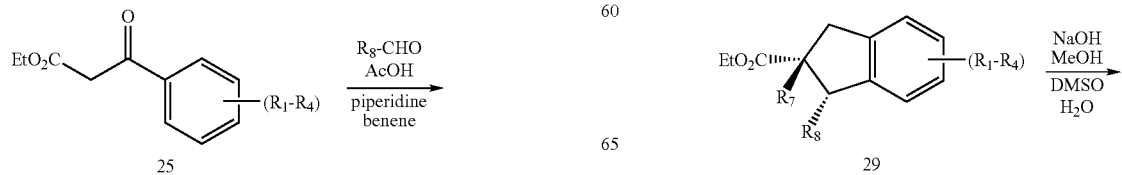

-continued

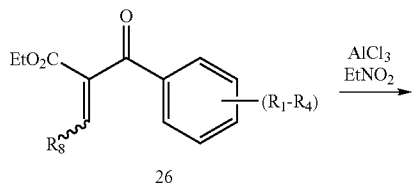

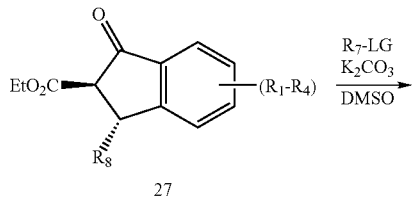

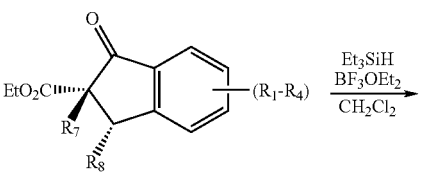

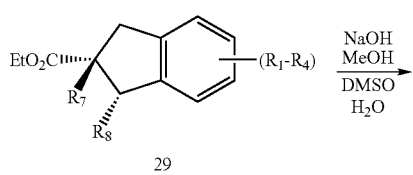

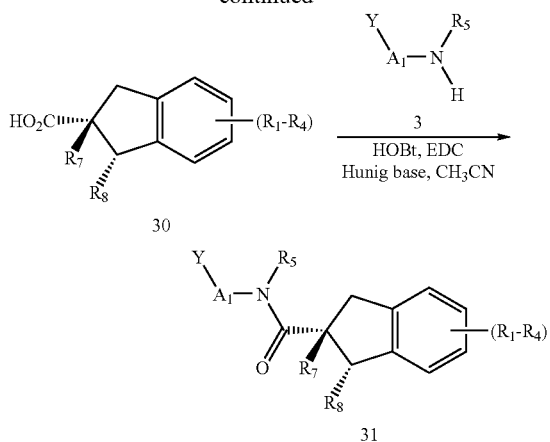

Scheme 6 outlines another synthesis for a series of 1,2-disubstituted indane-2-carboxamides. Carbomethoxylation of indanone 32, in the presence of NaH and dimethyl carbonate, gives a β-ketoester intermediate, which is reacted with $R_7$-LG and $K_2CO_3$ to yield 33. Nucleophilic addition to indanone 33 with a Grignard reagent ($R_8$—MgX, where X is a halide) gives a tertiary alcohol. The nucleophilic addition can also be effected with organolithium and organozinc reagents. The tertiary alcohol product is deoxygenated with triethylsilane and trifluoroacetic acid to give indane 34, which is converted to 35 using the saponification and coupling sequence described previously.

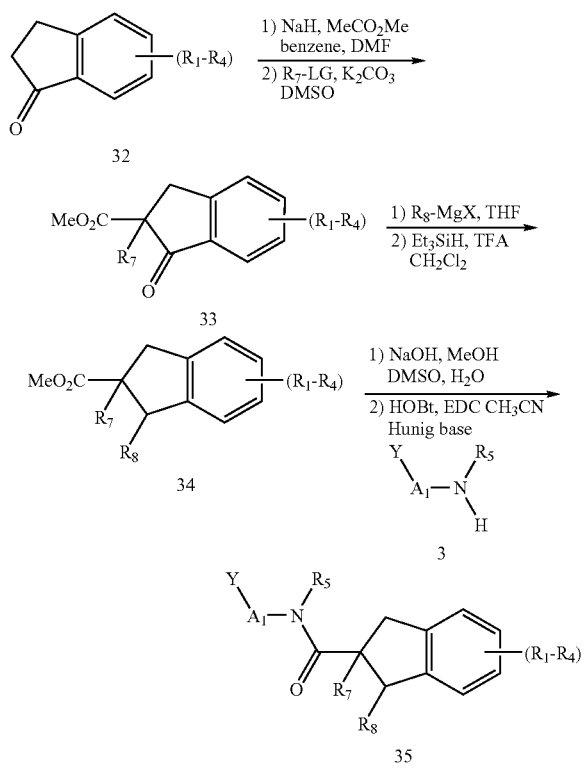

DEFINITION OF TERMS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$) hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)$ $R_b$, $SO_3H$, —$PO(OH)_2$, —$C(=O)R_a$, —$CO_2R_a$, —$C(=O)$ $NR_aR_b$, —$C(=O)(C_{1-4}alkylene)NR_aR_b$, —$C(=O)NR_a$ $(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2(alkyl)$, $C_{3-7}$cycloalkyl, phenyl, benzyl, phenylethyl, napthyl, a four to seven membered heterocylo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from ($C_{1-6}$)alkyl, ($C_{2-6}$)alkenyl, hydroxy, halogen, cyano, nitro, $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_{1-6}alkyl)$, —$S(C_{1-6}alkyl)$, —$NH_2$, $NH(C_{1-6}alkyl)$, $N(C_{1-6}alkyl)_2$, $N(CH_3)_3^+$, $SO_2(C_{1-6}$ alkyl), $C(=O)(C_{1-4}alkylene)NH_2$, $C(=O)(C_{1-4}alkylene)NH$ (alkyl), $C(=O)(C_{1-4}alkylene)N(C_{1-4}alkyl)_2$, $C_{3-7}$cycloalkyl, phenyl, benzyl, phenylethyl, phenyloxy, benzyloxy, napthyl, a four to seven membered heterocylo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

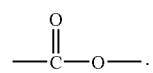

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl $(C_{0-4})$alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substitutents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO$_2$—, —NH—, and —NHSO$_2$—.

Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—(CH$_2$)$_{1-5}$NH—CH$_2$—, —O—(CH$_2$)$_{1-5}$S(=O)—CH$_2$—, —NHSO$_2$—CH$_2$—, —CH$_2$—NH—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1-2}$alkylene, or $C_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; $A_2$ is a bond, $C_{1-3}$alkylene, $C_{2-3}$alkenylene, —C$_{1-4}$alkylene-NR$_d$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteralkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an alkyl or substituted alkyl group as defined above having one or two oxygen atoms (—O—) in the alkyl chain. For example, the term "alkoxy" includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$alkyl, and so forth.

The term "thioalkyl" or "alkylthio" refers to an alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an alkyl or substituted alkyl group as defined above having one or two nitrogen (—NR—) atoms in the alkyl chain. For example, the term "aminoalkyl" includes the groups —NR—$C_{1-6}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$-aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_3$)$_2$. A lower aminoalkyl comprises an aminoalkyl having one to four carbon atoms. "Amino" refers to the group NH$_2$.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, $C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

It should be understood that the selections for alkoxy, thioalkyl, and aminoalkyl will be made by one skilled in the field to provide stable compounds. Thus, for example, in compounds of formula (I), when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "acyl" refers to a carbonyl group linked to an organic radical, more particularly, the group C(=O)$R_e$, as well as the bivalent groups C(=O)— or —C(=O)$R_e$—, which are linked to organic radicals or ring A in compounds of formula (I). The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in compounds of formula (I), when it is recited that G can be "acyl," this is intended to encompass a selection for G of C(=O)— and also the groups —C(=O)$R_e$— or —$R_e$C(=O)—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" refers to a carboxy group

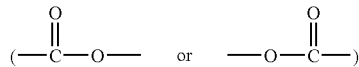

linked to an organic radical (CO$_2$R$_e$), as well as the bivalent groups —CO$_2$—, —CO$_2$R$_e$— which are linked to organic radicals in compounds of formula (I), wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.)

Accordingly, in compounds of formula (I), when it is recited that G can be "alkoxycarbonyl," this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" refers to the group C(=O)NR$_a$R$_b$, wherein the groups R$_a$ and R$_b$ are defined as recited above in the definition for substituted alkyl groups.

The term "sulfonyl" refers to a sulphoxide group linked to an organic radical in compounds of formula (I), more particularly, the monovalent group S(O)$_{1-2}$—R$_e$, or the bivalent group —S(O)$_{1-2}$— linked to organic radicals in compounds of formula (I). Accordingly, in compounds of formula (I), when it is recited that G can be "sulfonyl," this is intended to encompass a selection for G of —S(=O)— or —SO$_2$— as well as the groups —S(=O)R$_e$—, —R$_e$S(=O)—, —SO$_2$R$_e$—, or —R$_e$SO$_2$—, wherein in this instance, the group R$_e$ will be selected from those recited above for acyl and alkoxycarbonyl groups.

The term "sulfonamidyl" refers to the group —S(O)$_2$NR$_a$R$_b$, wherein R$_a$ and R$_b$ are as defined above for substituted alkyl groups. Additionally, the sulfonamidyl group may be bivalent, in which case one of the groups R$_a$ and R$_b$ will be a bond. Thus, in compounds of formula (I), when it is stated that G may be sulfonamidyl, it is intended to mean that G is a group —S(O)$_2$NR$_a$—.

The term "cycloalkyl" refers to fully saturated and partially unsaturated hydrocarbon rings of 3 to 9, preferably 3 to 7 carbon atoms. Accordingly, the term "cycloalkyl" is intended to include a cycloalkenyl (e.g. cyclohexenyl) ring. The term "cycloalkyl" includes such rings having zero, one, two or three substituents, and as valence allows, are selected from halogen, trifluoromethyl, trifluoromethoxy, alkyl, substituted alkyl, alkenyl, substituted alkenyl, alkynyl, substituted alkynyl, nitro, cyano, azide, oxo (=O), OR$_a$, SR$_a$, (=S), —NR$_a$R$_b$, —N(alkyl)$_3^+$, —(O)—C(=O)R$_a$, —(O)—C(=O)OR$_a$, —(O)—C(=O)NR$_a$R$_b$—NR$_a$SO$_2$, —NR$_a$SO$_p$R$_c$, —SO$_p$R$_c$, —SO$_p$NR$_a$R$_b$, —SO$_p$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, NR$_a$C(S)OR$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$)alkyl, (C$_{2-4}$)alkenyl, halogen, hydroxy, cyano, nitro, CF$_3$, O(C$_{1-4}$ alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$ alkyl), C(=O)(C$_{1-4}$alkylene)NH$_2$, C(=O)(C$_{1-4}$alkylene)NH (alkyl), and/or C(=O)(C$_{1-4}$alkylene)N(C$_{1-4}$alkyl)$_2$.

Accordingly, in compounds of formula (I), the term "cycloalkyl" includes cyclopropyl, cyclobutyl, cyclopentyl, cyclohexyl, cycloheptyl, cyclooctyl, etc., as well as the following ring systems,

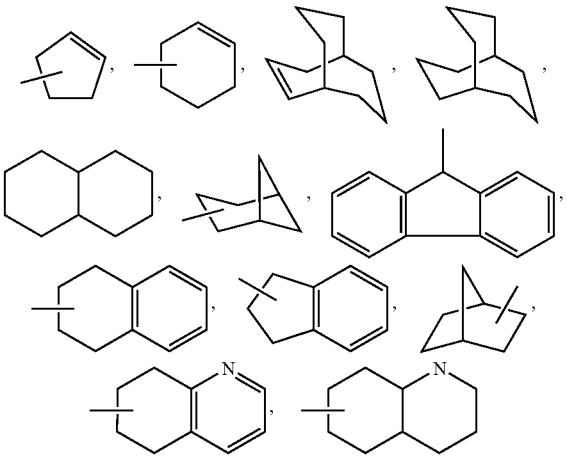

and the like, which optionally may be substituted at any available atoms of the ring(s). Preferred cycloalkyl groups include cyclopropyl, cyclobutyl, cyclopentyl, cyclohexyl,

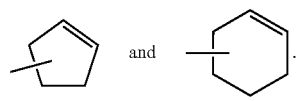

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "aryl" refers to phenyl, biphenyl, 1-naphthyl and 2-naphthyl. The term "aryl" includes such rings having zero, one, two or three substituents, and as valence allows, are selected from halogen, trifluoromethyl, trifluoromethoxy, alkyl, substituted alkyl, alkenyl, substituted alkenyl, alkynyl, substituted alkynyl, nitro, cyano, azide, oxo (=O), OR$_a$, SR$_a$, (=S), —NR$_a$R$_b$, —N(alkyl)$_3^+$, —(O)—C(=O)R$_a$, —(O)—C(=O)OR$_a$, —(O)—C(=O)NR$_a$R$_b$—NR$_a$SO$_2$, —NR$_a$SO$_p$R$_c$, —SO$_p$R$_c$—SO$_p$NR$_a$R$_b$, —SO$_p$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, NR$_a$C(S)OR$_b$, —NR$_a$(C$_{1-4}$alkylene)CO$_2$R$_b$, =N—OH, =N—O-alkyl, aryl, cycloalkyl, heterocyclo, and/ or heteroaryl wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, $O(C_{1-4}$alkyl$)$, $OCF_3$, $C(=O)H$, $C(=O)(C_{1-4}$alkyl$)$, $CO_2H$, $CO_2(C_{1-4}$alkyl$)$, $NHCO_2(C_{1-4}$alkyl$)$, $-S(C_{1-4}$alkyl$)$, $-NH_2$, $NH(C_{1-4}$alkyl$)$, $N(C_{1-4}$alkyl$)_2$, $N(C_{1-4}$alkyl$)_3^+$, $SO_2(C_{1-4}$alkyl$)$, $C(=O)(C_{1-4}$alkylene$)NH_2$, $C(=O)(C_{1-4}$alkylene$)NH($alkyl$)$, and/or $C(=O)(C_{1-4}$alkylene$)N(C_{1-4}$alkyl$)_2$.

Thus, examples of aryl groups include:

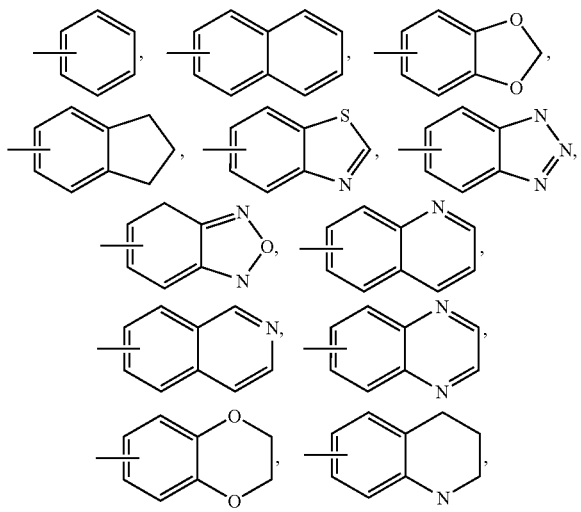

and the like, which optionally may be substituted at any available carbon or nitrogen atom. A preferred aryl group is optionally-substituted phenyl.

The terms "heterocyclo" or "heterocyclic" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain carbon, nitrogen, or sulfur atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents, and as valence allows, are selected from halogen, trifluoromethyl, trifluoromethoxy, alkyl, substituted alkyl, alkenyl, substituted alkenyl, alkynyl, substituted alkynyl, nitro, cyano, azide, oxo (=O), $OR_a$, $SR_a$, (=S), $-NR_aR_b$, $-N($alkyl$)_3^+$, $-(O)-C(=O)R_a$, $-(O)-C(=O)OR_a$, $-(O)-C(=O)NR_aR_b$, $-NR_aSO_2$, $-NR_aSO_pR_c$, $-SO_pR_c$, $-SO_pNR_aR_b$, $-SO_pNR_aC(=O)R_b$, $SO_3H$, $-PO(OH)_2$, $-C(=O)R_a$, $-CO_2R_a$, $-C(=O)NR_aR_b$, $-C(=O)(C_{1-4}$alkylene$)NR_aR_b$, $-C(=O)NR_a$ $(SO_2)R_b$, $-CO_2(C_{1-4}$alkylene$)NR_aR_b$, $-NR_aC(=O)R_b$, $-NR_aCO_2R_b$, $NR_aC(S)OR_b$, $-NR_a(C_{1-4}$alkylene$)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}$alkyl$)$, $OCF_3$, $C(=O)H$, $C(=O)(C_{1-4}$alkyl$)$, $CO_2H$, $CO_2(C_{1-4}$alkyl$)$, $NHCO_2(C_{1-4}$alkyl$)$, $-S(C_{1-4}$alkyl$)$, $-NH_2$, $NH(C_{1-4}$alkyl$)$, $N(C_{1-4}$alkyl$)_2$, $N(C_{1-4}$alkyl$)_3^+$, $SO_2(C_{1-4}$alkyl$)$, $C(=O)(C_{1-4}$alkylene$)NH_2$, $C(=O)(C_{1-4}$alkylene$)NH($alkyl$)$, and/or $C(=O)(C_{1-4}$alkylene$)N(C_{1-4}$alkyl$)_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

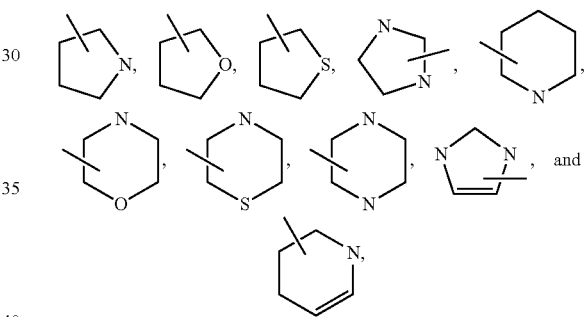

which optionally may be substituted.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain carbon, nitrogen or sulfur atoms, and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents, and as valence allows, are selected from halogen, trifluoromethyl, trifluoromethoxy, alkyl, substituted alkyl, alkenyl, substituted alkenyl, alkynyl, substituted alkynyl, nitro, cyano, azide, oxo (=O), $OR_a$, $SR_a$, (=S), $-NR_aR_b$, $-N($alkyl$)_3^+$, $-(O)-C(=O)R_a$, $-(O)-C(=O)NR_a$, $-(O)-C(=O)NR_aR_b-NR_aSO_2$, $-NR_aSO_pR_c$, $-SO_pR_c-SO_pNR_aR_b$, SO$_p$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, NR$_a$C(S)NR$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above. When a heteroaryl is substituted with a further ring, said ring in turn is optionally substituted with one to two of (C$_{1-4}$)alkyl, (C$_{2-4}$)alkenyl, halogen, hydroxy, cyano, nitro, CF$_3$, O(C$_{1-4}$ alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, SO$_2$(C$_{1-4}$ alkyl), C(=O)(C$_{1-4}$alkylene)NH$_2$, C(=O)(C$_{1-4}$alkylene)NH(alkyl), and/or C(=O)(C$_{1-4}$alkylene)N(C$_{1-4}$alkyl)-2

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

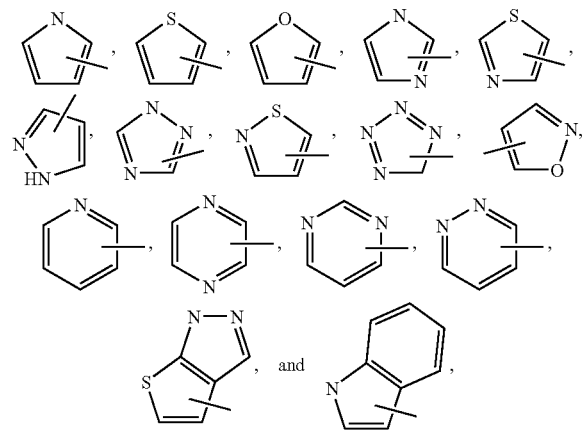

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include C$_{1-6}$alkylbenzyl, 4-methoxybenzyl, indanyl, phthalyl, methoxymethyl, C$_{1-6}$alkanoyloxy-C$_{1-6}$alkyl, e.g. acetoxymethyl, pivaloyloxymethyl or propionyloxymethyl, C$_{1-6}$alkoxycarbonyloxy-C$_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups:

(1-alkanoyloxy)alkyl such as,

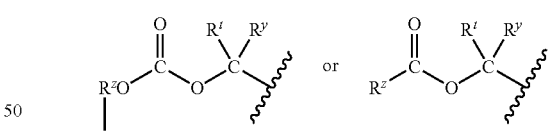

wherein R$^z$, R$^t$ and R$^y$ are H, alkyl, aryl or arylalkyl; however, R$^z$O cannot be HO.

Examples of such prodrug esters include

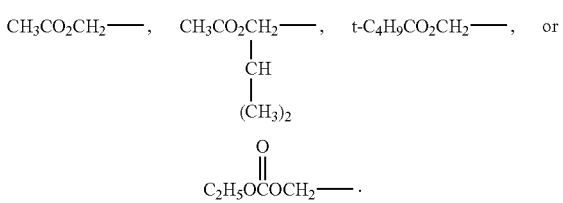

Other examples of suitable prodrug esters include

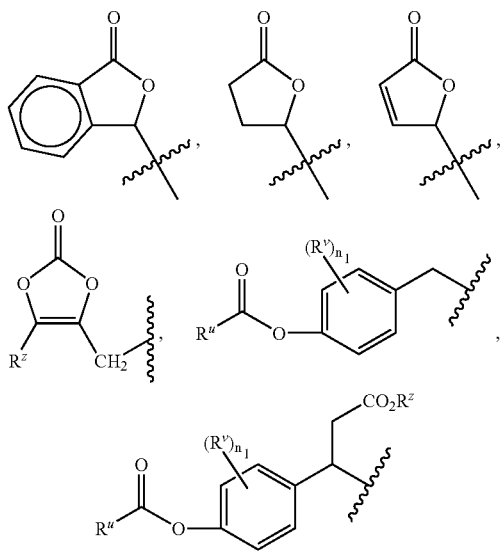

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992).

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or
arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g. hydrate) form.

COMBINATIONS

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf), The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

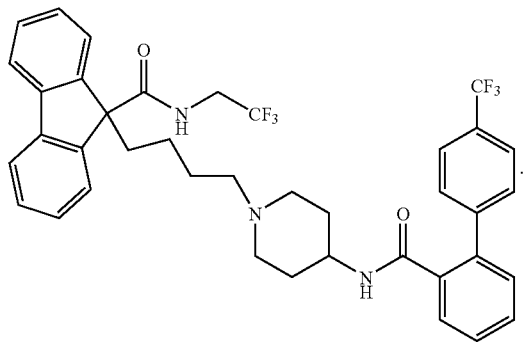

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., J. Med. Chem., Vol. 31, No. 10, pp. 1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, Vol. 2, pp. 1-40 (1996).

In addition, other squalene synthetase inhibitors suitable for use herein include the terpenoid pyrophosphates disclosed by P. Ortiz de Montellano et al., J. Med. Chem., 1977, 20, 243-249, the farnesyl diphosphate analog A and presqualene pyrophosphate (PSQ-PP) analogs as disclosed by Corey and Volante, J. Am. Chem. Soc., 98, 1291-1293 (1976), phosphinylphosphonates reported by McClard, R. W. et al., J. Am. Chem. Soc., 1987, 109, 5544 (1987), and cyclopropanes reported by Capson, T. L., PhD dissertation, Dept. Med. Chem. U of Utah, Abstract, Table of Contents, pp. 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future, 24, 9-15 (1999), (Avasimibe); "The ACAT inhibitor, C1-1011 is effective in the prevention and regression of aortic fatty streak area in hamsters", Nicolosi et al., *Atherosclerosis* (Shannon, Irel). 137 (1), 77-85 (1998), "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.* (1998), 16(1), 16-30; "RP 73163: a bioavailable alkylsulfinyl-diphenylimidazole ACAT inhibitor", Smith, C., et al, *Bioorg. Med. Chem. Lett.* 6(1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., *Inflammation: Mediators Pathways* 173-98 (1995), Publisher: CRC, Boca Raton, Fla.; "ACAT inhibitors: potential anti-atherosclerotic agents", Sliskovic et al, *Curr. Med. Chem.* 1(3), 204-25 1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Stout et al, *Chemtracts: Org. Chem.* 8(6), 359-62 (1995), or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's ezetimibe ($SCH_{58235}$) and SCH48461 as well as those disclosed in *Atherosclerosis* 115, 45-63 (1995) and *J. Med. Chem.* 41, 973 (1998).

The hypolipidemic agent may be an ileal $Na^+$/bile acid cotransporter inhibitor such as disclosed in *Drugs of the Future*, 24, 425-430 (1999).

The lipid-modulating agent may be a cholesteryl ester transfer protein (CETP) inhibitor such as Pfizer's CP 529,414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", *Brit. J Pharmacology* 120, 1199-1206 (1997), and Cornicelli et al, "15-Lipoxygenase and its Inhibition: A Novel Therapeutic Target for Vascular Disease", *Current Pharmaceutical Design*, 5, 11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998).

The antidiabetic agent may be an SGLT2 inhibitor such as disclosed in U.S. application Ser. No. 09/679,027, filed Oct. 4, 2000 employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]2-cyano-(S)-pyrrolidine) (Novartis) (preferred) as disclosed by Hughes et al, Biochemistry, 38(36), 11597-11603, (1999), TSL-225 (tryptophyl-1,2,3,4-tetrahydro-isoquinoline-3-carboxylic acid (disclosed by Yamada et al, Bioorg. & Med. Chem. Lett. 8 1537-1540 (1998), 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be A19677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with A19677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenyl-butyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C. A. 102:72588v and Jap. J. Pharmacol. 40:373 (1986); Ciba-Geigy's CGS 14824 (3-([1-ethoxy-carbonyl-3-phenyl-(1S)-propyl]amino)-2,3,4,5-tetrahydro-2-oxo-1-(3S)-benzepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J Cardiovasc. Pharmacol. 9:39 (1987); R 31-2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1, 2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, U.S. Pat. No. 5,552,397, U.S. Pat. No. 5,504,080, U.S. Pat. No. 5,612, 359,U.S. Pat. No. 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S—(R*,R*)]-hexahydro-6-[(2-mercapto-1-oxo-3-phenyl-propyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physician's Desk Reference.

PHARMACEUTICAL FORMULATIONS

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula I of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transcriptional assays.

Compounds of the invention, including the compounds described in the examples hereof, have been tested in at least one of the assay(s) described below and have glucocorticoid receptor (GR)/Dexamethasone (Dex) inhibition activity (>25% at 10 µM) and/or AP-1 inhibition activity ($EC_{50}$ less than 15 µM).

Identical and/or similar assays are described in copending provisional application No. 60/396,907, filed Jul. 18, 2002 which is incorporated in its entirety herein by reference.

GR (Dex) Binding Assay

In order to measure the binding of compounds to Site I on the glucocorticoid receptor a commercially available kit was used (Glucocorticoid receptor competitor assay kit, Panvera Co., Madison, Wis.). Briefly, a cell lysate containing recombinantly expressed human full-length glucocorticoid receptor was mixed with a fluorescently labeled glucocorticoid (4 nM FITC-dexamethasone) plus or minus test molecule. After one hour at room temperature, the fluorescence polarization (FP) of the samples were measured. The FP of a mixture of receptor, fluorescent probe (i.e. FITC-dexamethasone) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 0.1 nM to 40 µM.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e. are ligands for the specific NHR.

Cellular Transrepressional Assay

To measure the ability of test molecules to inhibit AP-1 induced transcriptional activity we utilized an A549 cell which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K., et al., *J. Biol. Chem.*, December 29; 270(52):31315-20 (1995) may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB. Additionally, AR mediated transrepression may be measured by the assay described in Palvimo J J, et al. *J. Biol. Chem.*, September 27; 271(39):24151-6 (1996), and PR mediated transrepression may be measured by the assay described in Kalkhoven E., et al. *J. Biol. Chem.*, March 15; 271(11):6217-24 (1996).

ABBREVIATIONS

The following abbreviations are employed in the following Preparations and Examples:
Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane HMPA=hexamethyl phosphoric triamide
HOAc or AcOH=acetic acid
TFA=trifluoroacetic acid
TFAA=trifluoroacetic anhydride
i-Pr$_2$NEt=diisopropylethylamine
Et$_3$N=triethylamine
NMM=N-methyl morpholine
DMAP=4-dimethylaminopyridine
NaBH$_4$=sodium borohydride
NaBH(OAc)$_3$=sodium triacetoxyborohydride
DIBALH=diisobutyl aluminum hydride
LAH or LiAlH$_4$=lithium aluminum hydride
n-BuLi=n-butyllithium
LDA=lithium diisopropylamide
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
NaN(TMS)$_2$=sodium hexamethyldisilazide or sodium bis(trimethylsilyl)amide
Ph$_3$P=triphenylphosphine
Pd(OAc)$_2$=Palladium acetate
(Ph$_3$P)$_4$Pd$^0$=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
Reverse phase HPLC=reverse phase high performance liquid chromatography, using a YMC ODS S5 column and a binary solvent A/solvent B eluents Solvent A=10% MeOH—90% H$_2$O—0.1% TFA
Solvent B=90% MeOH—10% H$_2$O—0.1% TFA
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point

EXAMPLES

The following Examples illustrate embodiments of the inventive compounds and starting materials, and are not intended to limit the scope of the claims.

Example 1

2-(2-phenyl-2,3-dihydro-1H-inden-2-yl)-N-1,3-thiazol-2-ylacetamide

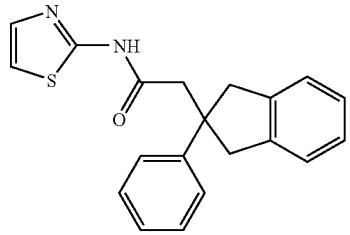

(1a) K$_2$CO$_3$ was added to a solution of 2-phenyl-2H-indene-1,3-dione (2.20 g, 10 mmol) and t-butyl bromoacetate (2.93 g, 1.5 eq) in DMSO (20 mL). After stirring at room temperature overnight, the mixture was quenched with water (100 mL) and extracted with ether-hexane (1:1, 3×100 mL). The combined extracts were washed with water (10 mL), brine (10 mL), dried (MgSO$_4$) and concentrated to about 30 mL. The precipitate was collected by filtration and washed with hexane (2×10 mL) to give a white solid (2.94 g, 87%). MS Found: (M+Na)$^+$=359.

(1b) Trifluoroacetic acid (5 mL) was added to a solution of the ester from reaction 1a (1.00 g, 2.97 mmol) in dichloromethane (5 mL). After 2 h at room temperature, the mixture was concentrated to give the desired acid as a white solid (830 mg, 100%). MS Found: (M+Na)$^+$=303.

(1c) Palladium hydroxide on carbon (500 mg, 10% by weight) was added to the acid from reaction 1b (500 mg, 1.78 mmol) in acetic acid (20 mL) and concentrated HCl (10 mL). The resultant mixture was reacted under hydrogen (50 psi) for 14 h using a Parr Shaker. The catalyst was removed by filtration. The filtrate was concentrated to give the desired acid as a white solid (450 mg, 100%). MS Found: (M–H)$^-$=251.

(1d) 2-Aminothiazole (20 mg, 2 eq), BOP (67 mg, 1.5 eq) and Hunig base (0.087 mL, 5 eq) were added to the acid from reaction IC (25.2 mg, 0.100 mmol) in DMF (2 mL) at room temperature. The resultant mixture was stirred at room temperature for 1 h and heated to 70° C. for 1 h. After evaporation of DMF under vacuum, the residue was purified by reverse phase HPLC (70-100% solvent B gradient) to give Example 1 (20.4 mg, 61%). MS Found: (M+H)$^+$=335.

Example 2

N-(4-((4-(4-pyridinyl)phenyl)methyl)-1,3-thiazol-2-yl)-2,3-dihydro-1H-indene-2-carboxamide

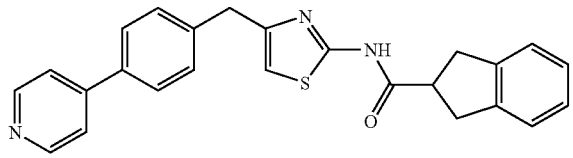

A MeCN (1 mL) solution of indane-2-carboxylic acid (16.8 mg, 0.1 mmol), 2-amino-4-(4-(pyridin-4-yl)benzyl)thiazole (28 mg, 1 eq, for synthesis, see WO2004009017), 1-ethyl-3-(3-dimethylaminopropyl)carbodiimide hydrochloride (33 mg, 1.7 eq), 1-hydroxybenzotriazole hydrate (15.4 mg, 1.1 eq) and N,N-diisopropylethylamine (40 µL, 2.2 eq) was heated to reflux overnight. The crude mixture was purified by preparative reverse-phase HPLC (60-100% solvent B gradient) to give Example 2 (8.1 mg, 15%). MS Found: (M+H)$^+$=412.

Example 3

2-(phenylmethyl)-N-1,3-thiazol-2-yl-2,3-dihydro-1H-indene-2-carboxamide

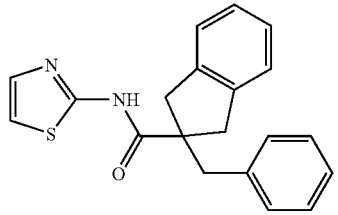

(3a) Iodomethane (2.9 mL, 1.5 eq) was added to a DMSO (100 mL) suspension of 2-indancarboxylic acid (5 g, 30.8 mmol) and K$_2$CO$_3$ (7.41 g, 1.7 eq). After stirring at room temperature overnight, the mixture was quenched with water (200 mL) and extracted with ether (2×100 mL). The combined extracts were washed with water (100 mL), brine (100 mL), dried (MgSO$_4$) and concentrated to give yellow oil (4.9 g, 90%). MS Found: (M+H)$^+$=177.

(3b) A 2.5 M hexane solution of butyllithium (3.46 mL, 1.3 eq) was added to diisopropylamine (1.24 mL, 1.4 eq) in THF (10 mL) at −78° C. The mixture was stirred at −78° C. for 20 min, warmed to 0° C. for 5 min then cooled to −78° C. The ester from reaction 3a (1.14 g, 6.48 mmol) in THF (10 mL) was added. The mixture was stirred at −40° C. for 30 min then cooled to −78° C. Benzyl bromide (1.54 mL, 2 eq) was added. The mixture was stirred at −78° C. overnight, quenched with saturated NH$_4$Cl (20 mL) and extracted with EtOAc (3×50 mL). The combined extracts were dried (MgSO$_4$), concentrated and purified by silica gel chromatography (ISCO 120 g silica gel cartridge, 0 to 10% EtOAc-hexanes) to give a colorless oil (1.50 g, 87%). MS Found: (M+Na)=289.

(3c) A 1 N aqueous solution of NaOH (10 mL) was added to the ester from reaction 3b (1.43 g, 5.38 mmol) in MeOH (10 mL). The mixture was heated to reflux for 1 h, concentrated and acidified with concentrated HCl (1 mL). The mixture was extracted with chloroform (50 mL). The extract was dried (MgSO$_4$) and concentrated to give a white solid (1.30 g, 96%).

(3d) Using a procedure similar to Example 2, the acid from reaction 3c (86 mg, 0.34 mmol) was coupled with 2-aminothiazole (35 mg, 1 eq) to give Example 3 (93 mg, 82%). MS Found: (M+H)$^+$=335.

Example 4

2-((4-(methyloxy)phenyl)methyl)-N-1,3-thiazol-2-yl-2,3-dihydro-1H-indene-2-carboxamide

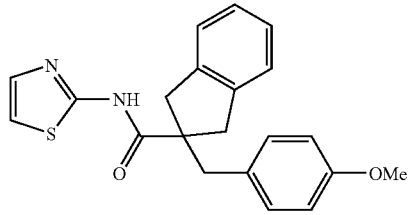

(4a) Using a procedure similar to reaction 3b, the ester from reaction 3a (0.50 g, 2.84 mmol) was reacted with 4-methoxybenzyl bromide (0.5 mL, 1.3 eq) to give the ester (0.49 g, 58%) as a colorless oil. MS Found: (M+Na)$^+$=319.

(4b) Using a procedure similar to reaction 3c, the ester from reaction 4a (0.23 g, 0.77 mmol) was hydrolyzed to give the acid (0.20 g, 92%) as a white solid. MS Found: (M+Na)$^+$=305.

(4c) Using a procedure similar to Example 2, the acid from reaction 4b (50.8 mg, 0.18 mmol) was coupled with 2-aminothiazole (20.9 mg, 1.2 eq) to give Example 4 (59.8 mg, 91%). MS Found: (M+H)$^+$=365.

Example 5

2-((4-hydroxyphenyl)methyl)-N-1,3-thiazol-2-yl-2,3-dihydro-1H-indene-2-carboxamide

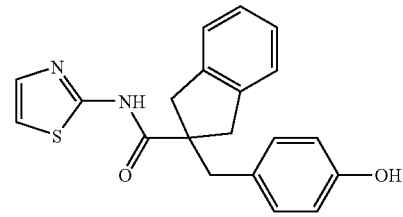

Boron tribromide (0.01 mL, 2.4 eq) was added to Example 4 (16 mg, 0.044 mmol) in dichloromethane (5 mL) at 0° C. After stirring at 0° C. for 2 h, the reaction mixture was quenched with saturated NaHCO$_3$ (20 mL). The dichloromethane layer was concentrated and purified by reverse-phase HPLC (70-100% solvent B gradient) to give Example 5 (9.8 mg, 64%). MS Found: (M+H)$^+$=351.

Example 6

2-((3-(methyloxy)phenyl)methyl)-N-1,3-thiazol-2-yl-2,3-dihydro-1H-indene-2-carboxamide

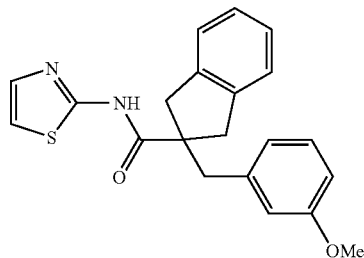

(6a) Using a procedure similar to reaction 3b, the ester from reaction 3a (0.42 g, 2.37 mmol) was reacted with 3-methoxybenzyl bromide (0.4 mL, 1.2 eq) to give the desired ester (0.32 g, 45%). MS Found: (M+Na)$^+$=319.

(6b) Using a procedure similar to reaction 3c, the ester from reaction 6a (0.18 g, 0.61 mmol) was hydrolyzed to give the crude acid (0.17 g). MS Found: (M+Na)$^+$=305.

(6c) Using a procedure similar to Example 2, the acid from reaction 6b (13 mg, 0.046 mmol) was coupled with 2-aminothiazole (23 mg, 5 eq) to give Example 6 (12.5 mg, 74%). MS Found: (M+H)$^+$=365.

Example 7

2-((3-hydroxyphenyl)methyl)-N-1,3-thiazol-2-yl-2,3-dihydro-1H-indene-2-carboxamide

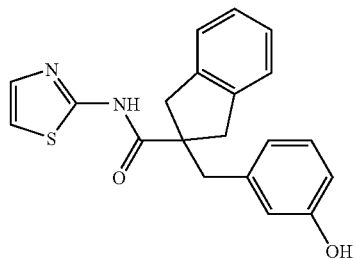

Using a procedure similar to Example 5, Example 6 (12.5 mg, 0.034 mmol) was converted to Example 7 (5.5 mg, 46%). MS Found: (M+H)$^+$=351.

Examples 10 and 11 rac-(1R,2S)-1-methyl-1-phenyl-N-1,3-thiazol-2-yl-2,3-dihydro-1H-indene-2-carboxamide and rac-(1R,2R)-1-methyl-1-phenyl-N-1,3-thiazol-2-yl-2,3-dihydro-1H-indene-2-carboxamide, respectively

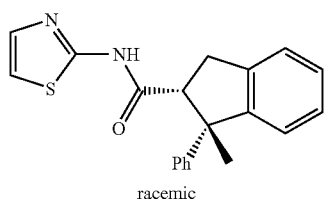

racemic

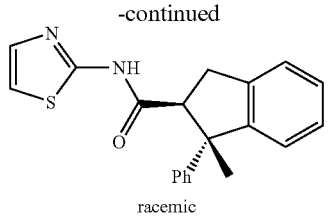

racemic (10a) Sodium hydride (1.89 g, 1.18 eq, 60% in mineral oil) was added to methyl diethylphosphonoacetate (8.81 mL, 1.2 eq) in THF (200 mL) at room temperature. After 2 h at room temperature, acetophenone (4.67 mL, 40 mmol) was added dropwise. The resultant mixture was stirred at room temperature for 3 h, at reflux for 2 h, then quenched with sat NH$_4$Cl (200 mL). After evaporation of THF in vacuo, the aqueous residue was extracted with EtOAc (3×100 mL). The combined extracts were washed with brine, dried (MgSO$_4$) and concentrated. Silica gel chromatography (EtOAc-Hex, 3:97 then 5:95) gave the desired enoate (4.915 g, 70%).

(10b) A 2.0 M solution of LDA (1.65 mL, 1.1 eq, from Aldrich) was added dropwise to a solution of the enoate from reaction 10a (528 mg, 3.0 mmol) in THF (40 mL) at −78° C. After 2 h at this temperature, 2-iodobenzyl bromide (1.12 g, 1.2 eq) in THF (5 mL) was added dropwise. The resultant mixture was allowed to slowly warm to room temperature overnight and quenched with sat NH$_4$Cl (100 mL). After evaporation of THF in vacuo, the aqueous residue was extracted with EtOAc (3×80 mL). The combined extracts were washed with brine, dried (MgSO$_4$) and concentrated. Silica gel chromatography (EtOAc-Hex, 2:98 then 3:97 then 4:96) provided the desired product (857 mg) which was contaminated with unreacted enoate (~29%).

(10c) A mixture of the impure ester from reaction 10b (857 mg), Pd(OAc)$_2$ (38 mg, 0.17 mmol), PPh$_3$ (164 mg, 0.624 mmol) and sodium formate (127 mg, 1.87 mmol) in DMF (20 mL) was heated under N$_2$ at 90° C. for 16 h. The mixture was quenched with water (50 mL) and extracted with ether (3×50 mL). The combined extracts were washed with brine, dried (MgSO$_4$) and concentrated. Silica gel chromatography (EtOAc-Hex, 3:97 then 4:96) provided the desired indane ester as a 3.5:1 mixture of trans and cis isomers (402 mg, 50% for two steps). MS Found: (M+Na)=289.

(10d) A 2 M toluene solution of trimethylaluminum (0.387 mL, 6 eq) was added to a mixture of the ester from reaction 10c (34.4 mg, 0.129 mmol) and 2-aminothiazole (77.4 mg, 6 eq) in toluene (8 mL). After 10 min at room temperature and 3 days at 95° C., the mixture was quenched with trifluoroacetic acid (0.1 mL) and concentrated. Purification by reverse phase HPLC (70% to 100% solvent B gradient) provide the cis isomer Example 10 (7.7 mg, 18%) and the trans isomer Example 11 (18.5 mg, 43%). MS Found for both isomers: (M+H)$^+$=335.

Example 12 rac-(1R,2R)-1-methyl-1-(1-oxido-4-pyridinyl)-N-1,3-thiazol-2-yl-2,3-dihydro-1H-indene-2-carboxamide

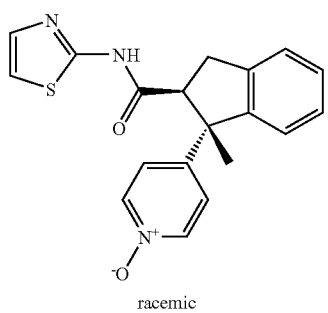

racemic (12a-c) Using a procedure similar to reactions 10a-c, the pyridyl-substituted indane ester was prepared from 4-acetylpyridine and methyl diethylphosphonoacetate. MS Found: (M+H)⁺=268.

(12d) A 1 N solution of NaOH (10 mL) was added to the indane ester from reaction 12c (240.8 mg, 0.902 mmol) in MeOH (10 mL). After 1.5 h at 70° C., the mixture was treated with trifluoroacetic acid (1 mL) and concentrated. Purification by reverse phase HPLC provided the corresponding trans acid (227.6 mg, 69%) and cis acid (39.3 mg), both as TFA salts. MS Found: (M+H)⁺=254.

(12e) A mixture of the trans acid from reaction 12d (30.7 mg, 0.0837 mmol), meta-chloroperbenzoic acid (130 mg, 77% pure from Aldrich) and CH₂Cl₂ (6 mL) was stirred at room temperature for 20 h and concentrated. Purification by reverse phase HPLC provided the pyridine-N-oxide acid (22.5 mg, 100%). MS Found: (M+H)⁺=270.

(12f) Using a procedure similar to reaction Id, the acid from reaction 12e was reacted with 2-aminothiazole to give Example 12 (22.3 mg, 76%). MS Found: (M+H)⁺=352.

Example 13 rac-(1R,2R)-1-methyl-N-(4-((4-(methyloxy)phenyl)methyl)-1H-imidazol-2-yl)-1-phenyl-2,3-dihydro-1H-indene-2-carboxamide

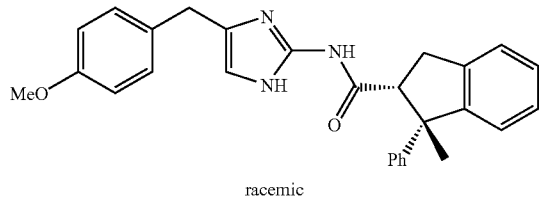

racemic

Using a sequence similar to the synthesis of Example 11, Example 13 was prepared using 2-amino-4-(4-methoxybenzyl)imidazole (for synthesis, see WO 2004/009017). MS Found: (M+H)⁺=438.

Example 14 rac-(1R,2S)-1-methyl-1-(4-((phenylmethyl)oxy)phenyl)-N-1,3-thiazol-2-yl-2,3-dihydro-1H-indene-2-carboxamide

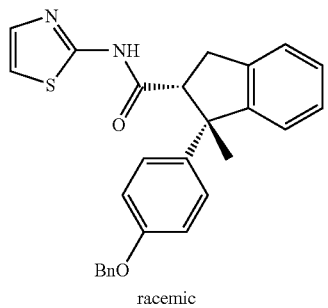

racemic (14a) Using a procedure similar to reaction 10a 4-benzyloxyacetophenone (3.86 g, 17.1 mmol) was reacted with tert-butyl diethylphosphonoacetate (5.11 g, 1.2 eq) to give the desired enoate (4.24 g, 77%) as a 4:1 E/Z mixture.

(14b) Using a procedure similar to reaction 10b the enoate from reaction 14a (1.44 g, 4.44 mmol) was reacted with 2-iodobenzyl bromide (1.31 g, 1 eq) to give the coupled product (1.33 g, 55%). MS Found: (M+Na)⁺=563.

(14c) Using a procedure similar to reaction 10c, the product from reaction 14b (0.65 g, 1.2 mmol) was converted to the indane ester (0.44 g) as a cis/trans mixture contaminated with a small amount of de-iodinated starting material. MS Found: (M+Na)⁺=437.

(14d) To a CH₂Cl₂ (6 mL) solution of the indane tert-butyl ester from reaction 14c (0.44 g) was added TFA (2 mL). The mixture was stirred at room temperature for 2 h then concentrated and purified by reverse-phase preparative HPLC (80 to 100% solvent B gradient) to give the indane acid (0.17 g, 44% for 2 steps) as a 3:1 trans/cis mixture. MS Found: (M−H)⁻=357.

(14e) Using a procedure similar to Example 2, the mixture of cis/trans acids from reaction 14d (16 mg, 0.045 mmol) was coupled with 2-aminothiazole (5.4 mg, 1.2 eq). Purification by reverse-phase HPLC (80 to 100% solvent B gradient) gave the cis isomer as Example 14 (2.7 mg, 14%) and the trans isomer (11.1 mg, 56%). MS Found: (M+H)⁺=441.

Example 15

2-(1,3-dioxo-2-phenyl-2,3-dihydro-1H-inden-2-yl)-N-(4-(4-fluoro-1-naphthalenyl)-1,3-thiazol-2-yl)acetamide

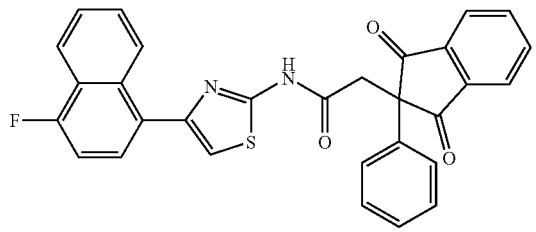

Using a procedure similar to the synthesis of Example 2, the acid from reaction 1b (26.5 mg, 1.5 eq) was reacted with 2-amino-4-(4-fluoronaphthalen-1-yl)thiazole (15.4 mg, 0.063 mmol) to give Example 15 (7.6 mg, 24%). MS Found: (M+H)⁺=507.

Examples 16 and 17 rac-(1R,2S)-1-(4-hydroxyphenyl)-1-methyl-N-1,3-thiazol-2-yl-2,3-dihydro-1H-indene-2-carboxamide and rac-(1R,2R)-1-(4-hydroxyphenyl)-1-methyl-N-1,3-thiazol-2-yl-2,3-dihydro-1H-indene-2-carboxamide, respectively

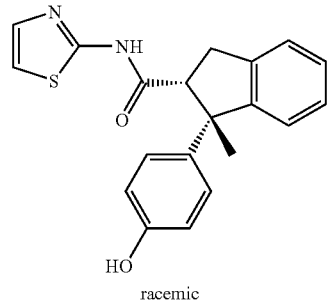

racemic

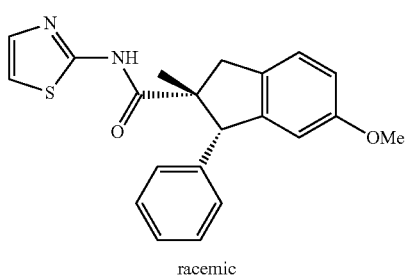

racemic (16a) To a solution of the acid mixture from reaction 14d (52.5 mg, 0.146 mmol) in MeOH (16 mL) was added palladium on carbon (18 mg). The mixture was hydrogenated at 50 psi for 21 h, filtered and concentrated to give a mixture of cis/trans phenol acids (45.5 mg). MS Found: $(M+Na)^+=291$.

(16b) Using a procedure similar to Example 2, the phenol acid mixture from reaction 16a (45.5 mg) was coupled with 2-aminothiazole (121 mg, 8 eq). Purification by reverse-phase HPLC (60 to 100% solvent B gradient) gave the cis isomer as Example 16 (4.1 mg, 8% for 2 steps) and the trans isomer as Example 17 (17.8 mg, 35% for 2 steps). MS Found: $(M+H)^+=351$.

Example 18 rac-(1R,2R)-2-methyl-1-phenyl-N-1,3-thiazol-2-yl-2,3-dihydro-1H-indene-2-carboxamide

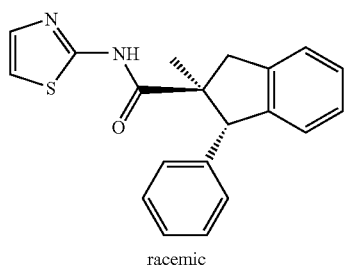

racemic (18a) A 2 M solution of LDA (21 mL, 1.05 eq, from Aldrich) was added dropwise to 3-phenyl-1-indanone (8.33 g, 40.0 mmol) in THF (300 mL) at −78° C. After 1 h at this temperature, iodomethane (3.00 mL, 1.2 eq) was added. The mixture was stirred at −78° C. for 2 h, at 0° C. for 30 min and quenched with sat NH$_4$Cl (100 mL). After evaporation of THF in vacuo, the aqueous residue was extracted with EtOAc (3×100 mL). The combined extracts were washed with brine (20 mL), dried (MgSO$_4$) and concentrated. Silica gel chromatography (EtOAc-Hex, 5:95 then 7:93 then 10:90) gave the 2-methylindanone (1.93 g, 22%). MS Found: $(M+H)^+=223$.

(18b) A 2 M solution of LDA (8.69 mL, 2 eq) was added dropwise to the 2-methylindanone from reaction 18a (1.93 g, 8.69 mmol) in THF (100 mL) at −78° C. After 2 h at this temperature, HMPA (3.02 mL, 2 eq) was added. After 30 min at −78° C., methyl cyanoformate (1.38 mL, 2 eq) was added. The mixture was stirred at −78° C. for 1 h, at 0° C. for 30 min, and quenched with sat NH$_4$Cl (100 mL). After evaporation of THF in vacuo, the aqueous residue was extracted with EtOAc (3×100 mL). The combined extracts were dried (MgSO$_4$) and concentrated. Silica gel chromatography (EtOAc-Hex, 8:92 then 10:90) provided the desired keto-ester (1.84 g, 76%). MS Found: $(M+Na)^+=303$.

(18c) A mixture of the keto-ester from reaction 18b (1.52 g, 5.43 mmol), triethylsilane (20 mL), trifluoroacetic acid (20 mL) and CH$_2$Cl$_2$ (40 mL) was stirred at room temperature for 2 days and concentrated. Purification by silica gel chromatography (EtOAc-Hex, 3:97 then 5:95) gave the desired ester (1.05 g, 73%). MS Found: $(M+Na)^+=289$.

(18d) Using a procedure similar to reaction 8d, the ester from reaction 18c was reacted with 2-aminothiazole to give Example 18 (27.5 mg, 41%). MS Found: $(M+H)^+=335$.

Example 19

N-(4-(4-fluoro-1-naphthalenyl)-1,3-thiazol-2-yl)-2-(2-phenyl-2,3-dihydro-1H-inden-2-yl)acetamide

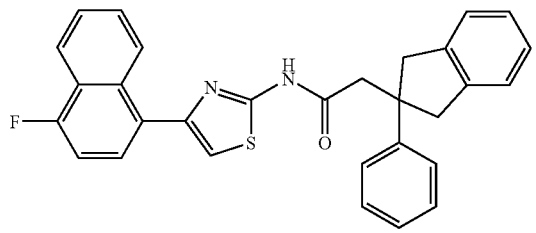

Using a procedure similar to the synthesis of Example 2, the acid from reaction 1c (30.7 mg, 2 eq) was reacted with 2-amino-4-(4-fluoronaphthalen-1-yl)thiazole (15.0 mg, 0.061 mmol) to give Example 19 (5.5 mg, 19%). MS Found: $(M+H)^+=479$.

Example 20 rac-(1R,2S)-2-methyl-6-(methyloxy)-1-phenyl-N-1,3-thiazol-2-yl-2,3-dihydro-1H-indene-2-carboxamide racemic (20a) A solution of ethyl 4-methoxybenzoylacetate (10.77 g, 48.46 mmol), benzaldehyde (5.2 g, 1 eq), acetic acid (1.39 mL, 0.5 eq) and piperidine (0.48 mL, 0.1 eq) in benzene (400 mL) was heated to reflux for 5 h with azeotropic removal of water using a Dean-Stark trap. The mixture was concentrated to give the crude product as a yellow powder (15.54 g). MS Found: $(M+Na)=333$.

(20b) A solution of the mixture from reaction 20a (15.54 g, 0.048 mol) and aluminum chloride (8.3 g, 1.2 eq) in nitroethane (350 mL) was heated to 90° C. for 6 h. After cooling, the mixture was quenched by adding aqueous HCl (2 N, 500 mL) and extracted with dichloromethane (400 mL). The dichloromethane phase was washed with aqueous HCl (2 N, 250 mL), water (250 mL) and brine (50 mL), dried (MgSO$_4$), and concentrated to give the crude indanone (15.65 g) as an orange gum. MS Found: (M+Na)⁺=333.

(20c) A mixture of the indanone from reaction 20b (5.54 g, 16.1 mmol), iodomethane (2.5 mL, 2.5 eq) and $K_2CO_3$ (11.13 g, 5 eq) in DMSO (70 mL) was stirred at room temperature overnight, quenched with water (500 mL) and extracted with ether (400 mL). The ether phase was washed with water (200 mL) and brine (20 mL), dried ($MgSO_4$) and concentrated to give a yellow oil (5.37 g). The crude material was crystallized in 5% EtOAc-hexanes to give the desired product as a white crystalline solid (2.96 g, 57%). The mother liquor was purified by silica gel chromatography (EtOAc-hexanes, 5%, 7%, 10%, 15% then 20%) to give additional product (1.29 g, 25%). MS Found: (M+Na)⁺=347.

(20d) A $CH_2Cl_2$ (90 mL) solution of the product from reaction 20c (4.25 g, 13.1 mmol), triethylsilane (90 mL, 43 eq) and boron trifluoride etherate (90 mL, 54 eq) was stirred at room temperature for 65 h. The mixture was concentrated in vacuo. The residue was triturated with hexanes-ether (200 mL, 1:1) and filtered. The solid (borate salt) was discarded. The filtrate was washed with saturated $NaHCO_3$ until no more bubble formed, then with water (50 mL) and brine (20 mL), dried ($MgSO_4$) and concentrated to ~20 mL volume. A white needle crystal was obtained as the pure product (3.35 g, 82%). MS Found: (M+Na)⁺=333.

(20e) The ester from reaction 20d (2.90 g, 9.34 mmol) was dissolved in a mixture of MeOH (50 mL), DMSO (50 mL) and aqueous NaOH (1N, 50 mL) and heated at reflux for 24 h. After removal of MeOH in vacuo, the aqueous residue was acidified with 2 N aqueous HCl (30 mL) and extracted with chloroform (250 mL). The chloroform phase was washed with water (200 mL) and brine (50 mL), dried ($MgSO_4$) and concentrated. Crystallization from 10% EtOAc-hexanes gave the desired acid (2.55 g, 97%) as white needles. MS Found: (M+Na)=305.

(20f) Using a procedure similar to Example 2, the acid from reaction 20e (127 mg, 0.45 mmol) was reacted with 2-aminothiazole to give Example 20 (125 mg, 76%). MS Found: (M+H)⁺=365.

Examples 21 to 23 rac-(1R,2S)-2-methyl-1-phenyl-N-1,3-thiazol-2-yl-2,3-dihydro-1H-indene-2-carboxamide; (1R,2S)-2-methyl-1-phenyl-N-1,3-thiazol-2-yl-2,3-dihydro-1H-indene-2-carboxamide; and (1S,2R)-2-methyl-1-phenyl-N-1,3-thiazol-2-yl-2,3-dihydro-1H-indene-2-carboxamide respectively

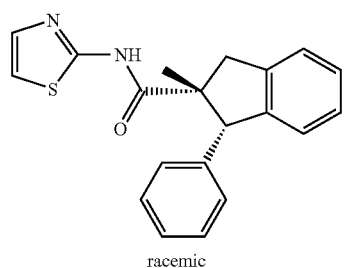

racemic

-continued

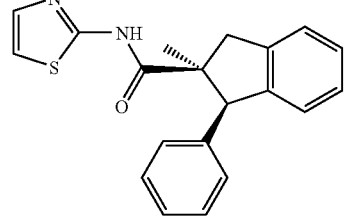

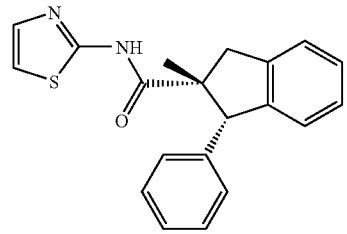

(21a-f) Using conditions similar to reactions 2a-f, ethyl benzoylacetate and benzaldehyde were reacted to give Example 21 as a racemate. MS Found: (M+H)⁺=335.

(21b) Example 21 (43.7 mg) was separated on preparative Chiralcel-OJ HPLC column (30×250 mm, 5µ packing particle size, 7.5% MeOH—7.5% EtOH-85% Heptane, 20 mL/min) to give the fast eluting enantiomer as Example 22 (14.5 mg) and the slow eluting enantiomer as Example 23 (14 mg). MS Found: (M+H)⁺=335.

Example 24 rac-(1R,2S)-1,2-dimethyl-N-1,3-thiazol-2-yl-2,3-dihydro-1H-indene-2-carboxamide

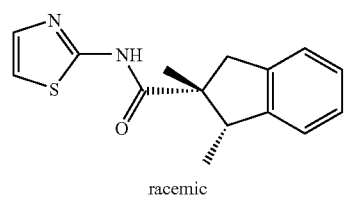

racemic (24a) $K_2CO_3$ (5.40 g, 5 eq) and iodomethane (2.44 mL, 5 eq) were added to 3-methyl-1H-indene-2-carboxylic acid (1.363 g, 7.82 mmol) in DMSO (20 mL). After 1.5 h at room temperature, the mixture was quenched with saturated $NH_4Cl$ (200 mL) and extracted with EtOAc (3×100 mL). The combined extracts were washed with water (10 mL), brine (10 mL), dried ($MgSO_4$) and concentrated. The residue was filtered through a silica gel pad and the pad washed with EtOAc-Hex (20:80). The filtrate was concentrated to give the desired ester (1.421 g, 97%). MS Found: (M+H)⁺=189.

(24b) A mixture of the ester from reaction 24a (268 mg, 1.43 mmol) and Pd/C (268 mg, 10% by weight) in MeOH (20 mL) was hydrogenated under 50 psi $H_2$ for 24 h using a Parr Shaker. The catalyst was removed by filtration. The filtrate was concentrated to give the indane ester (271 mg, 100%). MS Found: (M+Na)⁺=213.

(24c-d) Using conditions similar to reactions (20e) and Example 2, the indane ester from reaction 24b was hydrolyzed and reacted with 2-aminothiazole to give Example 24 (34.3 mg). MS Found: (M+H)⁺=273.

Example 25 rac-(1R,2S)-2-methyl-1-(3-(methyloxy)phenyl)-N-1,3-thiazol-2-yl-2,3-dihydro-1H-indene-2-carboxamide;

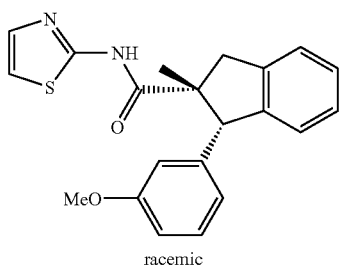

racemic

Using conditions similar to reactions 20a-f, ethyl benzoylacetate and 3-methoxybenzaldehyde were reacted to give Example 25 as a racemate. MS Found: (M+H)⁺=365.

Examples 26 and 27

(1S,2R)-2-methyl-1-(3-(methyloxy)phenyl)-N-1,3-thiazol-2-yl-2,3-dihydro-1H-indene-2-carboxamide; and (1R,2S)-2-methyl-1-(3-(methyloxy)phenyl)-N-1,3-thiazol-2-yl-2,3-dihydro-1H-indene-2-carboxamide

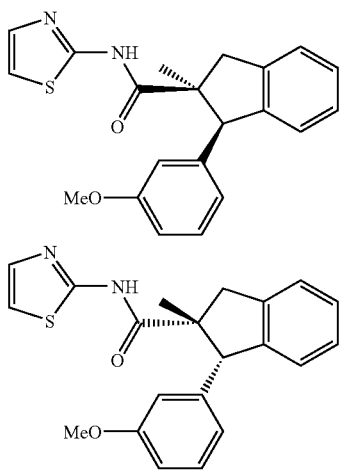

Example 25 (110 mg) was separated on preparative Chiralcel-AD HPLC column (30×250 mm, 5μ packing particle size, 10% MeOH—10% EtOH-80% Heptane, 20 mL/min) to give the fast eluting enantiomer as Example 26 (51 mg) and the slow eluting enantiomer as Example 27 (51 mg). MS Found: (M+H)⁺=335.

Example 28 rac-(1R,2S)-1-(3-hydroxyphenyl)-2-methyl-N-1,3-thiazol-2-yl-2,3-dihydro-1H-indene-2-carboxamide

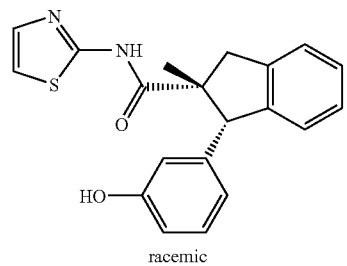

racemic

Using a procedure similar to Example 5, Example 25 (20.3 mg, 0.0558 mmol) was converted to Example 28 (12.7 mg, 65%). MS Found: (M+H)⁺=351.

Example 29 rac-(1R,2S)-1-(4-bromophenyl)-2-methyl-N-1,3-thiazol-2-yl-2,3-dihydro-1H-indene-2-carboxamide

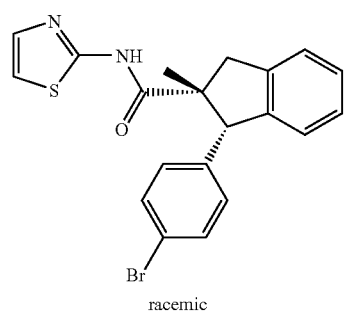

racemic (29a-b) Using conditions similar to reactions 20a and 20b, ethyl benzoylacetate and 4-bromobenzaldehyde were reacted to give the corresponding indanone. MS Found: (M+Na)⁺=381, 383.

(29c) A mixture of the indanone from reaction 29b (941 mg, 2.62. mmol), triethylsilane (7.5 mL), trifluoroacetic acid (7.5 mL) and CH₂Cl₂ (15 mL) was stirred at room temperature for 3 days. After evaporation of solvent in vacuo, the residue was purified by silica gel chromatography (EtOAc-Hex, 2:98 then 3:97 then 4:96) to give the desired indane (712 mg, 77%). MS Found: (M+Na)⁺=367, 369.

(29d) A 2 M solution of LDA (1.52 mL, 1.5 eq) was added dropwise to a solution of the indane from reaction 29c (697.9 mg, 2.02 mmol) in THF (50 mL) at −78° C. After 90 min at this temperature, HMPA (0.656 mL, 2 eq) was added. The mixture was stirred at −78° C. for 30 min, then treated with iodomethane (0.504 mL, 4 eq). After 2 h at −78° C., the dry ice-acetone bath was replaced with an ice-water bath and the mixture stirred overnight while warming to room temperature. Following addition of saturated NH₄Cl (80 mL), THF was evaporated in vacuo. The aqueous residue was extracted with Et₂O-Hex (1:1, 3×50 mL). The combined extracts were washed with brine, dried (MgSO₄) and concentrated. Silica gel chromatography (EtOAc-Hex, 2:98 then 3:97 then 4:96) provided the 2-methylated indane (687.7 mg, 95%). MS Found: (M+Na)⁺=381, 383.

(29e-f) Using conditions similar to reactions 20e-f, the indane from reaction 29d was converted to Example 29. MS Found: (M+H)⁺=413, 415.

Example 30 rac-(1R,2S)-2-methyl-1-(4-(methyloxy)phenyl)-N-1,3-thiazol-2-yl-2,3-dihydro-1H-indene-2-carboxamide

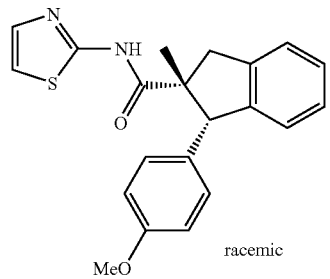

Using conditions similar to reactions 2a-f, ethyl benzoylacetate and 4-methoxybenzaldehyde were reacted to give Example 30. MS Found: (M+H)$^+$=365.

Example 31 rac-(1R,2S)-1-(4-hydroxyphenyl)-2-methyl-N-1,3-thiazol-2-yl-2,3-dihydro-1H-indene-2-carboxamide

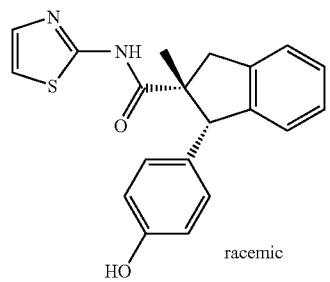

Using conditions similar to the synthesis of Example 5, Example 30 (77.2 mg, 0.212 mmol) was converted to Example 31 (51.1 mg, 69%). MS Found: (M+H)$^+$=351.

Example 32 methyl 4-((1R,2S)-2-methyl-2-((1,3-thiazol-2-ylamino)carbonyl)-2,3-dihydro-1H-inden-1-yl)phenyl rac-carbonate

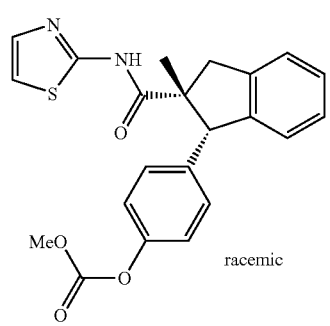

To a CH$_2$Cl$_2$ (2 mL) solution of the phenol from Example 31 (10.5 mg, 0.03 mmol) was added triethylamine (21 μL, 5 eq), DMAP (0.5 M dichloromethane solution, 6 μL, 0.1 eq) and methyl chloroformate (4.6 μL, 2 eq). The mixture was stirred at room temperature for 1.5 h, concentrated and purified by reverse-phase HPLC (70 to 100% solvent B) to give Example 32 (12 mg, 99%). MS Found: (M+H)$^+$=409.

Example 33

4-((1R,2S)-2-methyl-2-((1,3-thiazol-2-ylamino)carbonyl)-2,3-dihydro-1H-inden-1-yl)phenyl rac-methylcarbamate

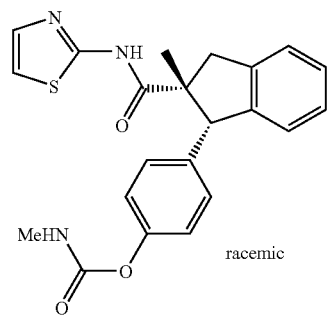

Using a procedure similar to the synthesis of Example 32, the phenol from Example 31 (10.5 mg, 0.03 mmol) was reacted with methyl isocyanate (4 μL, 2.2 eq) to give Example 33 (10.6 mg, 87%). MS Found: (M+H)$^+$=408.

Example 34

4-((1R,2S)-2-methyl-2-((1,3-thiazol-2-ylamino)carbonyl)-2,3-dihydro-1H-inden-1-yl)phenyl rac-dimethylcarbamate

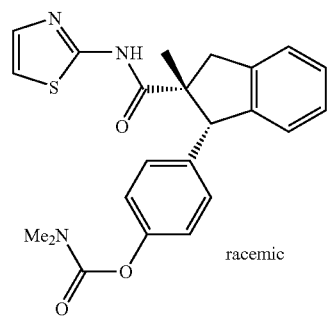

Using a procedure similar to the synthesis of Example 32, the phenol from Example 31 (10.4 mg, 0.03 mmol) was reacted with dimethylcarbamyl chloride (13.8 μL, 5 eq) to give Example 34 (8.6 mg, 69%). MS Found: (M+H)$^+$=422.

Example 35 rac-(1R,2S)-2-methyl-5-(methyloxy)-1-phenyl-N-1,3-thiazol-2-yl-2,3-dihydro-1H-indene-2-carboxamide

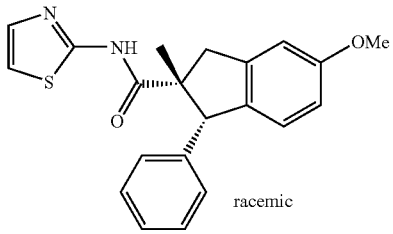

Using conditions similar to reactions 20a-f, ethyl 3-methoxybenzoylacetate and benzaldehyde were converted to Example 35. MS Found: (M+H)$^+$=365.

Example 36 rac-(1R,2S)-5-hydroxy-2-methyl-1-phenyl-N-1,3-thiazol-2-yl-2,3-dihydro-1H-indene-2-carboxamide

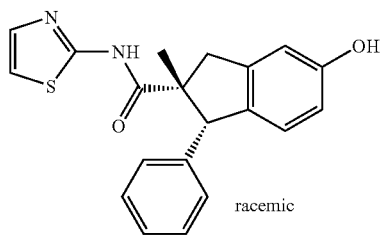
racemic

Using conditions similar to the synthesis of Example 5, the compound from Example 35 (100 mg, 0.274 mmol) was converted to Example 36 (89 mg, 93%). MS Found (M+H)$^+$= 351.

Example 37 methyl (1R,2S)-2-methyl-1-phenyl-2-((1,3-thiazol-2-ylamino)carbonyl)-2,3-dihydro-1H-inden-5-yl rac-carbonate

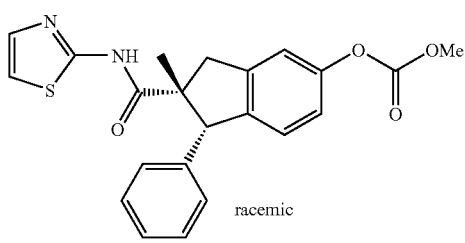
racemic

Using a procedure similar to the synthesis of Example 32, the phenol from Example 36 (9.9 mg, 0.028 mmol) was reacted with methyl chloroformate (4.4 μL, 2 eq) to give Example 37 (8.5 mg, 74%). MS Found: (M+H)$^+$=409.

Example 38

(1R,2S)-2-methyl-1-phenyl-2-((1,3-thiazol-2-ylamino carbonyl)-2,3-dihydro-1H-inden-5-yl rac-methylcarbamate

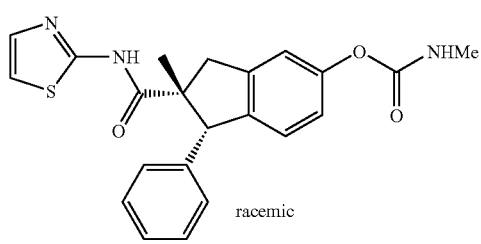
racemic

Using a procedure similar to the synthesis of Example 32, the phenol from Example 36 (10.7 mg, 0.03 mmol) was reacted with methyl isocyanate (4.4 μL, 2.4 eq) to give Example 38 (5.9 mg, 48%). MS Found: (M+H)$^+$=408.

Example 39

(1R,2S)-2-methyl-1-phenyl-2-((1,3-thiazol-2-ylamino carbonyl)-2,3-dihydro-1H-inden-5-yl rac-dimethylcarbamate

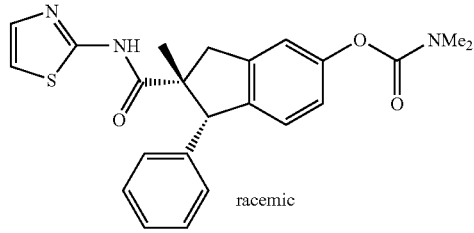
racemic

Using a procedure similar to the synthesis of Example 32, the phenol from Example 36 (10.4 mg, 0.03 mmol) was reacted with dimethylcarbamyl chloride (13.8 μL, 5 eq) to give Example 39 (8.6 mg, 69%). MS Found: (M+H)$^+$=422.

Example 40 rac-(1R,2S)-2-ethyl-1-phenyl-N-1,3-thiazol-2-yl-2,3-dihydro-1H-indene-2-carboxamide

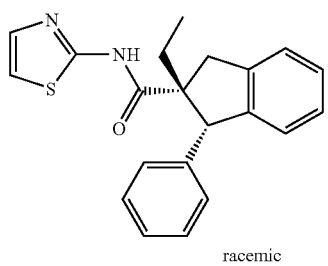
racemic

Using conditions similar to reactions 20a-f except iodoethane was used in 20c, ethyl benzoylacetate and benzaldehyde were converted to Example 40. MS Found: (M+H)$^+$=349.

Example 41 rac-(1R,2S)-6-hydroxy-2-methyl-1-phenyl-N-1,3-thiazol-2-yl-2,3-dihydro-1H-indene-2-carboxamide

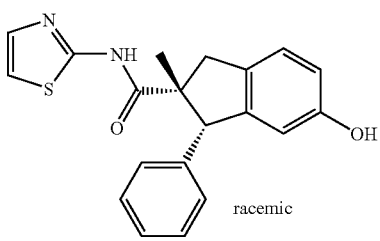
racemic

Using a procedure similar to the synthesis of Example 5, the compound from Example 20 (28 mg, 0.077 mmol) was converted to Example 41 (15.5 mg, 58%). MS Found (M+H)$^+$=351.

Example 42

(2R,3S)-2-methyl-3-phenyl-2-((1,3-thiazol-2-ylamino carbonyl)-2,3-dihydro-1H-inden-5-yl rac-acetate

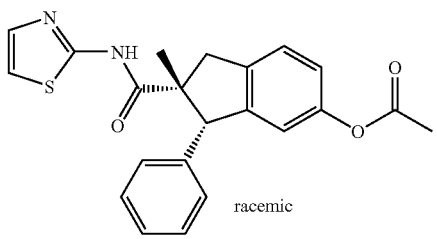

Using a procedure similar to the synthesis of Example 32, the phenol from Example 41 (7.5 mg, 0.021 mmol) was reacted with acetyl chloride (6 µL, 4 eq) to give Example 42 (7.8 mg, 93%). MS Found: (M+H)$^+$=393.

Example 43 methyl (2R,3S)-2-methyl-3-phenyl-2-((1,3-thiazol-2-ylamino)carbonyl)-2,3-dihydro-1H-inden-5-yl rac-carbonate

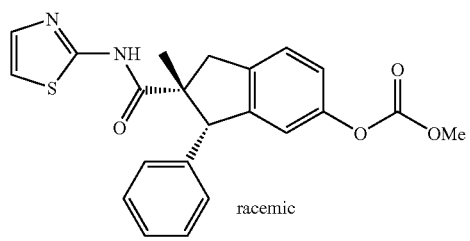

Using a procedure similar to the synthesis of Example 32, the phenol from Example 41 (7 mg, 0.02 mmol) was reacted with methyl chloroformate (3.2 µL, 2 eq) to give Example 43 (5.8 mg, 71%). MS Found: (M+H)$^+$=409.

Example 44

(2R,3S)-2-methyl-3-phenyl-2-((1,3-thiazol-2-ylamino)carbonyl)-2,3-dihydro-1H-inden-5-yl rac-methylcarbamate

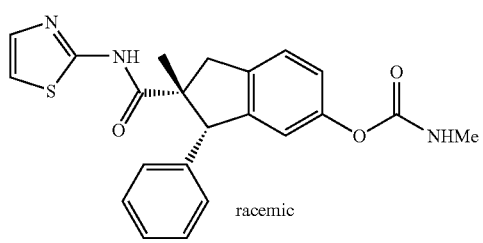

Using a procedure similar to the synthesis of Example 32, the phenol from Example 41 (6.6 mg, 0.019 mmol) was reacted with methyl isocyanate (2.3 µL, 2 eq) to give Example 44 (7.3 mg, 95%). MS Found: (M+H)$^+$=408.

Example 45 rac-(1R,2S)-2-methyl-6-(methyloxy)-N-(4-methyl-1,3-thiazol-2-yl)-1-phenyl-2,3-dihydro-1H-indene-2-carboxamide

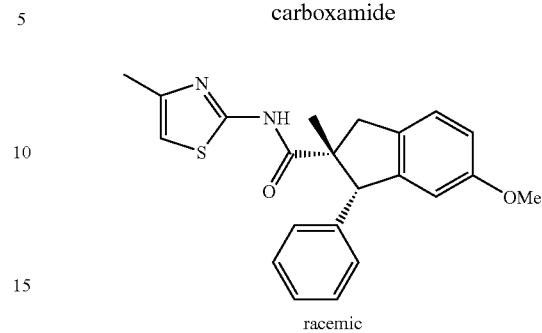

Using a procedure similar to the synthesis of Example 2, the acid from 20e (35.3 mg, 0.125 mmol) was reacted with 2-amino-4-methylthiazole (30.8 mg, 2.2 eq) to give Example 45 (33.2 mg, 70%). MS Found: (M+H)$^+$=379.

Example 46 rac-(1R,2S)-6-hydroxy-2-methyl-N-(4-methyl-1,3-thiazol-2-yl)-1-phenyl-2,3-dihydro-1H-indene-2-carboxamide

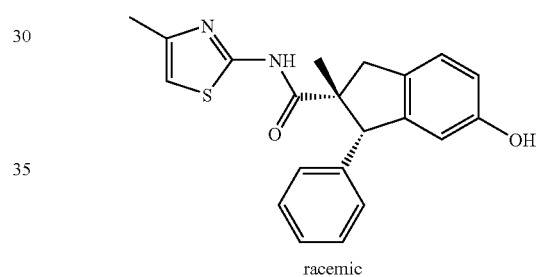

Using a procedure similar to the synthesis of Example 5, the compound from Example 45 (25.4 mg, 0.067 mmol) was converted to Example 46 (18.2 mg, 75%). MS Found: (M+H)$^+$=365.

Example 47 rac-(1R,2S)-2-methyl-6-(methyloxy)-N-(5-methyl-1,3-thiazol-2-yl)-1-phenyl-2,3-dihydro-1H-indene-2-carboxamide

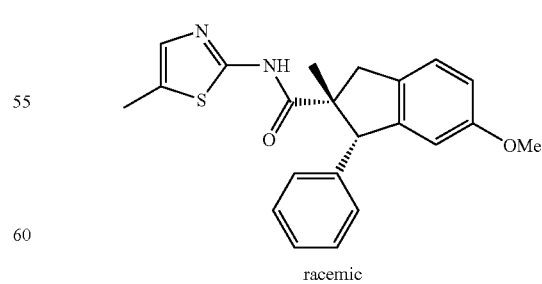

Using a procedure similar to the synthesis of Example 2, the acid from 20e (35 mg, 0.124 mmol) was reacted with 2-amino-5-methylthiazole (29.7 mg, 2.1 eq) to give Example 47 (39.3 mg, 84%). MS Found: (M+H)$^+$=379.

Example 48 rac-(1R,2S)-6-hydroxy-2-methyl-N-(5-methyl-1,3-thiazol-2-yl)-1-phenyl-2,3-dihydro-1H-indene-2-carboxamide

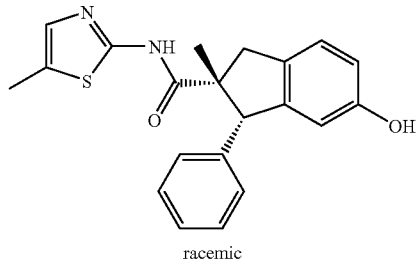

racemic

Using a procedure similar to the synthesis of Example 5, the compound from Example 47 (30.2 mg, 0.08 mmol) was converted to Example 48 (21 mg, 72%). MS Found (M+H)$^+$= 365.

Example 49 rac-(1R,2S)—N-(4,5-dimethyl-1,3-thiazol-2-yl)-2-methyl-6-(methyloxy)-1-phenyl-2,3-dihydro-1H-indene-2-carboxamide

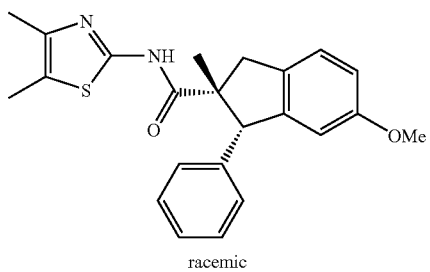

racemic

Using a procedure similar to the synthesis of Example 2, the acid from reaction 20e (35 mg, 0.124 mmol) was reacted with 2-amino-4,5-dimethylthiazole (36 mg, 2.3 eq) to give Example 49 (41 mg, 84%). MS Found: (M+H)$^+$=393.

Example 50 rac-(1R,2S)—N-(4,5-dimethyl-1,3-thiazol-2-yl)-6-hydroxy-2-methyl-1-phenyl-2,3-dihydro-1H-indene-2-carboxamide

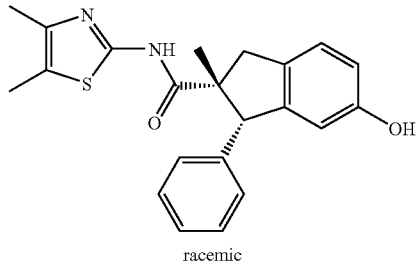

racemic

Using a procedure similar to the synthesis of Example 5, the compound from Example 49 (31.7 mg, 0.08 mmol) was converted to Example 50 (20.3 mg, 66%). MS Found (M+H)$^+$=379.

Example 51 rac-(1R,2S)—N-1H-imidazol-2-yl-2-methyl-6-(methyloxy)-1-phenyl-2,3-dihydro-1H-indene-2-carboxamide

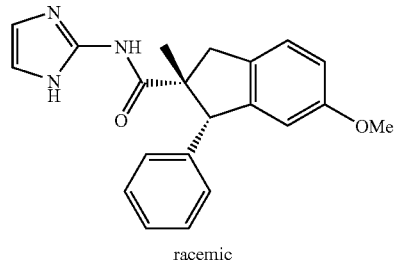

racemic

Using a procedure similar to the synthesis of Example 2, the acid from reaction 20e (35 mg, 0.124 mmol) was reacted with 2-aminoimidazole ½H$_2$SO$_4$ salt (34 mg, 2.1 eq) to give Example 51 (27 mg, 47%). MS Found: (M+H)$^+$=348.

Example 52 rac-(1R,2S)-6-hydroxy-N-1H-imidazol-2-yl-2-methyl-1-phenyl-2,3-dihydro-1H-indene-2-carboxamide

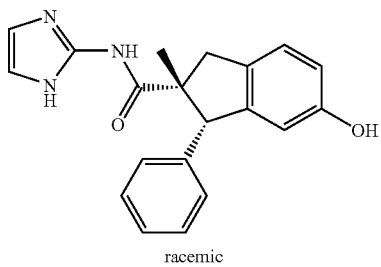

racemic

Using a procedure similar to the synthesis of Example 5, the compound from Example 51 (20 mg, 0.043 mmol) was converted to Example 52 (11 mg, 58%). MS Found (M+H)$^+$= 334.

Example 53 rac-(1R,2S)—N-1,3-benzothiazol-2-yl-2-methyl-6-(methyloxy)-1-phenyl-2,3-dihydro-1H-indene-2-carboxamide

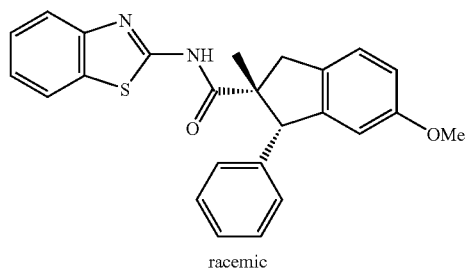

racemic

Using a procedure similar to the synthesis of Example 2, the acid from reaction 20e (34 mg, 0.112 mmol) was reacted with 2-aminobenzothiazole (36 mg, 2 eq) to give Example 53 (35 mg, 70%). MS Found: (M+H)$^+$=415.

Example 54 rac-(1R,2S)—N-1,3-benzothiazol-2-yl-6-hydroxy-2-methyl-1-phenyl-2,3-dihydro-1H-indene-2-carboxamide

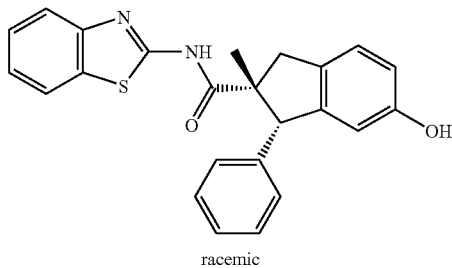

racemic

Using a procedure similar to the synthesis of Example 5, the compound from Example 53 (27 mg, 0.065 mmol) was converted to Example 54 (18.5 mg, 72%). MS Found (M+H)$^+$=401.

Example 55 rac-(1R,2S)-2-methyl-6-(methyloxy)-1-phenyl-N-1,3,4-thiadiazol-2-yl-2,3-dihydro-1H-indene-2-carboxamide

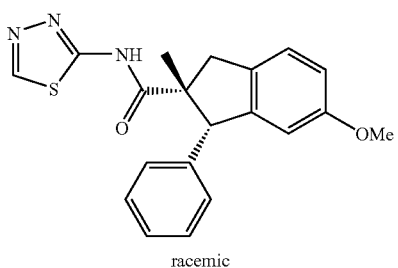

racemic

Using a procedure similar to the synthesis of Example 2, the acid from reaction 20e (45.6 mg, 0.162 mmol) was reacted with 2-amino-1,3,4-thiadiazole (21.5 mg, 1.3 eq) to give Example 55 (32.6 mg, 55%). MS Found: (M+H)$^+$=366.

Example 56 rac-(1R,2S)-6-hydroxy-2-methyl-1-phenyl-N-1,3,4-thiadiazol-2-yl-2,3-dihydro-1H-indene-2-carboxamide

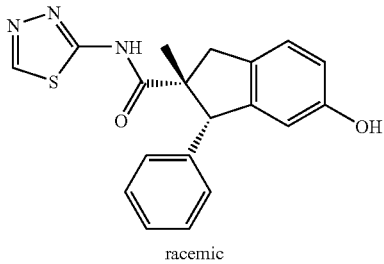

racemic

Using a procedure similar to the synthesis of Example 5, the compound from Example 55 (19 mg, 0.053 mmol) was converted to Example 56 (10 mg, 54%). MS Found (M+H)$^+$=352.

Example 57

N-(4-((4-(methyloxy)phenyl)methyl)-1,3-thiazol-2-yl)-2-(2-phenyl-2,3-dihydro-1H-inden-2-yl)acetamide

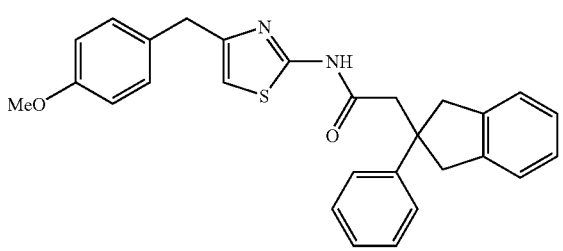

Using a procedure similar to the synthesis of Example 2, the acid from reaction 1c (34.7 mg, 2 eq) was reacted with 2-amino-4-(4-methoxybenzyl)thiazole (15.0 mg, 0.068 mmol, for synthesis, see WO2004009017) to give Example 57 (9.8 mg, 32%). MS Found: (M+H)$^+$=455.

Example 58 rac-2-(((1R,2S)-6-hydroxy-2-methyl-1-phenyl-2,3-dihydro-1H-inden-2-yl)carbonyl)hydrazinecarboxamide

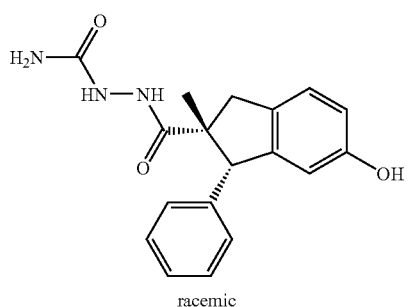

racemic (58a) Semicarbazide (14.4 mg, 1.6 eq), HOBt (12.8 mg, 1.2 eq), EDCI (38.8 mg, 2.5 eq) and Hunig base (0.14 mL, 10 eq) were added to the acid from reaction 20e (22.6 mg, 0.08 mmol) in acetonitrile (1.5 mL) at room temperature. The mixture was stirred at room temperature overnight and concentrated. The residue was purified by reverse phase HPLC (50-80% solvent B gradient) to give the desired product (17.8 mg, 65%). MS Found: (M+H)$^+$=340.

(58b) Using a procedure similar to the synthesis of Example 5, the compound from reaction 58a (16 mg, 0.047 mmol) was converted to Example 58 (3.6 mg, 25%). MS Found: (M+Na)$^+$=348.

Example 59 rac-5-((1R,2S)-2-methyl-6-(methyloxy)-1-phenyl-2,3-dihydro-1H-inden-2-yl)-2,4-dihydro-3H-1,2,4-triazol-3-one

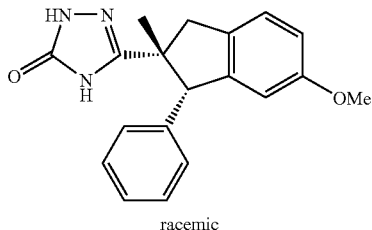

racemic

The compound from reaction 58a (16.6 mg, 0.049 mmol) in 2 N aqueous solution of NaOH (3 mL) was heated at 100° C. for 6 h. After cooling, the solution was acidified with 6 N HCl (1 mL) and extracted with EtOAc (3×5 mL). The organic phase was concentrated and purified by reverse-phase HPLC (60 to 90% solvent B gradient) to give Example 59 (0.8 mg, 5%). MS Found: $(M+H)^+=322$.

Example 60 rac-(1R,2R)-6-(methyloxy)-1-phenyl-N-1,3-thiazol-2-yl-2,3-dihydro-1H-indene-2-carboxamide

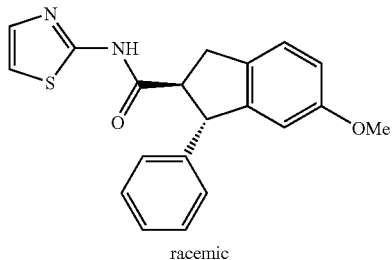

racemic (60a) A CH$_2$Cl$_2$ (10 mL) solution of the indanone from reaction 20b (0.95 g, 3.1 mmol), triethylsilane (15 mL, 31 eq) and trifluoroacetic acid (15 mL) was stirred at room temperature for 52 h. The mixture was concentrated in vacuo and purified by silica gel chromatography (3 to 5% ethyl acetate-hexanes) to give the indane ester (0.75 g, 82%). MS Found: $(M+Na)^+=319$.

(60b-c) Using conditions similar to 20e and Example 2, the indane ester from reaction 60a was hydrolyzed and coupled with 2-aminothiazole to give Example 60. MS Found: $(M+H)^+=351$.

Example 61

(1S,2R)-5-formyl-2-methyl-6-(methyloxy)-1-phenyl-N-1,3-thiazol-2-yl-2,3-dihydro-1H-indene-2-carboxamide

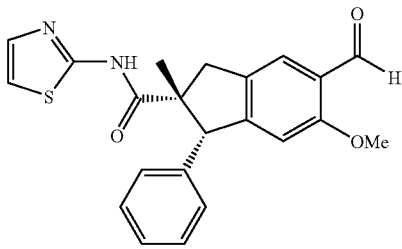

(61a) The racemate acid from 20e (26.6 g) was separated by SFC Chiralcel OJ column (30×500 mm, 5μ packing particle size, 5% MeOH—95% CO$_2$, 60 mL/min) to give a fast eluting enantiomer (12.4 g) and a slow eluting enantiomer (11.8 g).

(61b) A TFA (20 mL) solution of the slow eluting enantiomer from 61a (0.47 g, 1.68 mmol) and hexamethylenetetramine (0.24 g, 1 eq) was heated to reflux for 1 h. The mixture was concentrated and purified by silica gel chromatography (15, 20, 30 and 40% EtOAc-hexanes) to give the desired aldehyde acid (0.31 g, 59%).

(61c) Using a procedure similar to Example 2, the acid from reaction 61b (107.5 mg, 0.35 mmol) was reacted with 2-aminothiazole (87 mg, 2.5 eq) to give Example 61 (74.7 mg, 55%). MS Found: $(M+H)^+=393$.

Example 62

(1S,2R)-5-formyl-6-hydroxy-2-methyl-1-phenyl-N-1,3-thiazol-2-yl-2,3-dihydro-1H-indene-2-carboxamide

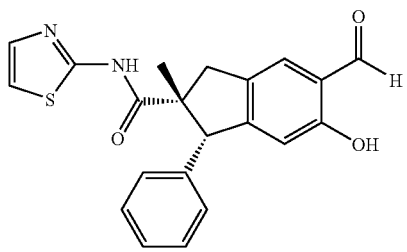

Using a procedure similar to the synthesis of Example 5, the compound from Example 61 (65 mg, 0.166 mmol) was converted to Example 62 (44 mg, contaminated with 10% Example 61, inseparable by reverse-phase HPLC, 63%). MS Found: $(M+H)^+=379$.

Example 63 rac-(1R,2S)-2-methyl-6-(methyloxy)-1-(3-(methyloxy)phenyl)-N-1,3-thiazol-2-yl-2,3-dihydro-1H-indene-2-carboxamide

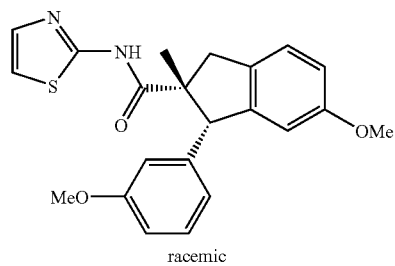

racemic

Using conditions similar to reactions 20a-f, ethyl (4-methoxybenzoyl)acetate and 3-methoxybenzaldehyde were converted to Example 63. MS Found: $(M+H)^+=395$.

Examples 64 and 65 rac-(1R,2S)-1-(3-hydroxyphenyl)-2-methyl-6-(methyloxy)-N-1,3-thiazol-2-yl-2,3-dihydro-1H-indene-2-carboxamide; and rac-(1R,2S)-6-hydroxy-1-(3-hydroxyphenyl)-2-methyl-N-1,3-thiazol-2-yl-2,3-dihydro-1H-indene-2-carboxamide, respectively

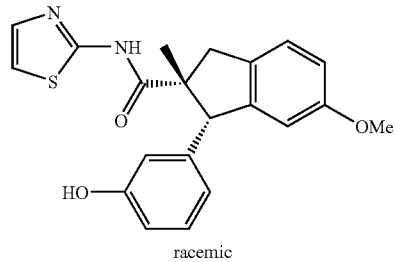

racemic

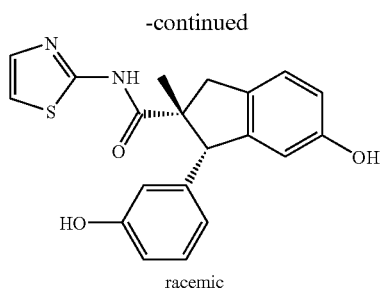

racemic

BBr$_3$ (0.032 mL, 1.5 eq) was added to the product from Example 63 (87.8 mg, 0.223 mmol) in CH$_2$Cl$_2$ (10 mL) at 0° C. After 45 min at this temperature, additional BBr$_3$ (0.032 mL) was added. After another 40 min, the mixture was quenched with saturated NaHCO$_3$ (25 mL) and extracted with EtOAc (3×25 mL). The combined extracts were washed with brine (10 mL), dried (MgSO$_4$) and concentrated. Purification by reverse phase HPLC (60-90% solvent B gradient) provided the mono-phenol Example 64 (24.5 mg, 29%) and bis-phenol Example 65 (42.5 mg, 48%). MS Found: Example 64 (M+H)$^+$=381, Example 65 (M+H)$^+$=367.

Example 66 rac-(1R,2S)-2-methyl-6-(methyloxy)-1-(3-(methyloxy)phenyl)-N-1,3,4-thiadiazol-2-yl-2,3-dihydro-1H-indene-2-carboxamide

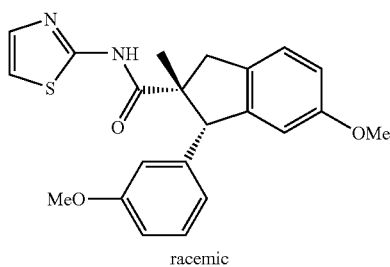

racemic

Using a procedure similar to Example 2, the acid from reaction 63e (306 mg, 0.980 mmol) was reacted with 2-amino-1,3,4-thiadiazole to give Example 66 (131.6 mg, 24%). MS Found: (M+H)$^+$=396.

Example 67 rac-(1R,2S)-6-hydroxy-1-(3-hydroxyphenyl)-2-methyl-N-1,3,4-thiadiazol-2-yl-2,3-dihydro-1H-indene-2-carboxamide

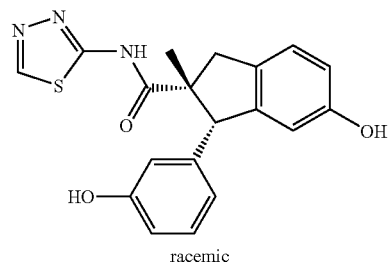

racemic

Using a procedure similar to the synthesis of Example 5, the compound from Example 66 was converted to Example 67. MS Found: (M+H)$^+$=368.

Example 68 rac-(1R,2S)-2-methyl-5,6-bis(methyloxy)-1-phenyl-N-1,3-thiazol-2-yl-2,3-dihydro-1H-indene-2-carboxamide

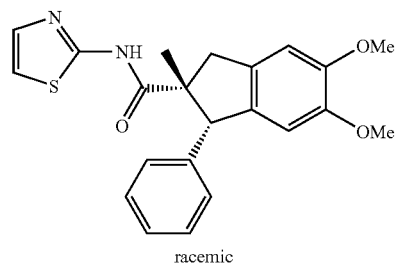

racemic

Using a procedure similar to reactions 0a-f ethyl (3,4-dimethoxybenzoyl)acetate and benzaldehyde were reacted to give Example 68. MS Found: (M+H)$^+$=395.

Example 69 rac-(1R,2S)-5,6-dihydroxy-2-methyl-1-phenyl-N-1,3-thiazol-2-yl-2,3-dihydro-1H-indene-2-carboxamide

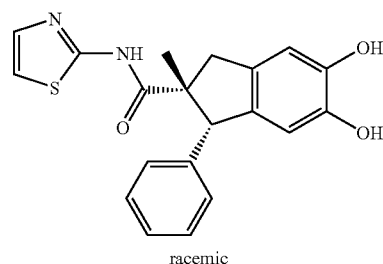

racemic

Using procedure similar to the synthesis of Example 5, the compound from Example 68 was converted to Example 69. MS Found: (M+H)$^+$=367.

Example 70 rac-(5R,6S)-6-methyl-5-phenyl-N-1,3-thiazol-2-yl-6,7-dihydro-5H-indeno[5,6-d][1,3]dioxole-6-carboxamide

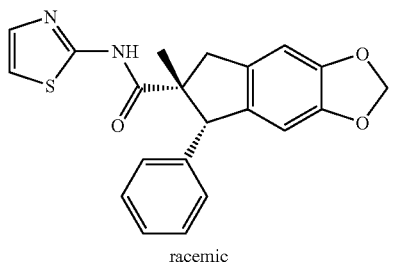

racemic

Bromochloromethane (19.4 mg, 1.5 eq) and cesium carbonate (48.9 mg, 1.5 eq) were added to the compound from Example 69 (36.6 mg, 0.100 mmol) in DMF (2 mL). The mixture was heated to 110° C. for 2 h, then quenched with 1 N HCl (1 mL) and saturated NH₄Cl (10 mL). The mixture was extracted with EtOAc (3×10 mL). The combined extracts were washed with brine, dried (MgSO₄) and concentrated. Purification by reverse phase HPLC (80-100% solvent B gradient) provided Example 70 (2.4 mg). MS Found: (M+H)$^+$=379.

Example 71 rac-(1R,2S)-6-iodo-2-methyl-1-phenyl-N-1,3-thiazol-2-yl-2,3-dihydro-1H-indene-2-carboxamide

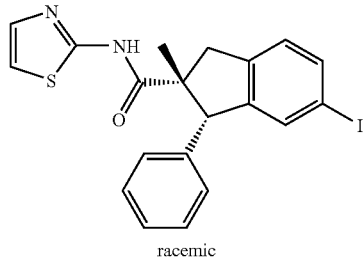

racemic

Using conditions similar to reactions 20a-b 29c-d and 20e-f, ethyl (4-iodobenzoyl)acetate and benzaldehyde were reacted to give Example 71. MS Found: (M+H)$^+$=461.

Example 72 rac-(1R,2R)-6-iodo-1-phenyl-N-1,3-thiazol-2-yl-2,3-dihydro-1H-indene-2-carboxamide

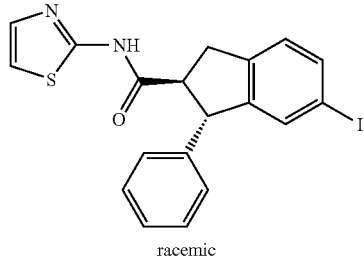

racemic

Using procedure similar to reactions 20a-b, 29c, and 20e-, ethyl (4-iodobenzoyl)acetate and benzaldehyde were reacted to give Example 72. MS Found: (M+H)$^+$=447.

Example 73 rac-(1R,2S)-6-bromo-2-methyl-1-phenyl-N-1,3-thiazol-2-yl-2,3-dihydro-1H-indene-2-carboxamide

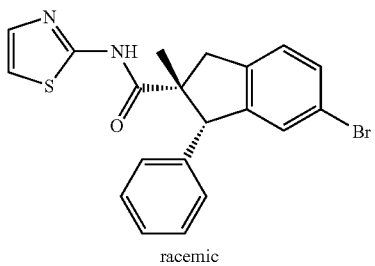

racemic (73a) Triethylamine (83.6 mL, 2 eq) and MgCl₂ (71.42 g, 2.5 eq) were added to a stirred mixture of potassium methyl malonate (96.1 g, 2.05 eq) in CH₃CN (800 mL) at 10-15° C. (cooled with a cold water bath). The mixture was stirred at ambient temperature for 2.5 h (internal temperature reached 30° C. then back to 25° C.). The mixture was cooled with an ice-water bath. A solution of 4-bromobenzoyl chloride (65.84 g, 300 mmol) in CH₃CN (100 mL) was added over 1 h. Additional Et₃N (0.2 eq) was added. The resultant mixture was stirred at room temperature overnight, concentrated in vacuo and pumped to dryness under high vacuum. The mixture was diluted with toluene (500 mL), cooled with an ice-water bath, quenched with 12% HCl (500 mL), and stirred until all solid dissolved. After separation of the two layers, the aqueous phase was extracted with toluene (2×250 mL). The organic extracts were combined with the original toluene phase and washed with 12% HCl (2×100 mL), brine (100 mL), dried (MgSO₄) and concentrated to give a waxy solid. $^1$H NMR indicated a mixture of keto and enol tautomers. The crude material was taken to the next step without purification. MS Found: (M+Na)$^+$=279, 281.

(73b) Acetic acid (8.59 mL, 0.5 eq) and piperidine (2.96 mL, 0.1 eq) were added to a mixture of the crude ketoester from reaction 73a (maximum 300 mmol) and benzaldehyde (32.47 g, 1.02 eq) in benzene (800 mL) at room temperature. The resultant mixture was heated to reflux for 3 h, with azeotropic removal of water using a Dean-Stark trap. After evaporation of solvent in vacuo, the residue was dissolved in EtOAc-hexane (1:1) and filtered through a pad of silica gel. The silica gel pad was rinsed with EtOAc-hexane (1:1) until free of the product. The filtrate was concentrated to give the crude product as a brown solid. MS Found: (M+Na)$^+$=367, 369.

(73c) A solution of AlCl₃ (48.0 g, 1.2 eq) in nitroethane (50 mL) was added over 20 min to a suspension of crude material from reaction 73b (maximum 300 mmol) in nitroethane (400 mL). The mixture was heated to 90° C. for 2 h, cooled to room temperature, quenched with 1 N HCl (1 L) and extracted with chloroform (3×400 mL). The combined extracts were dried (MgSO₄) and filtered through a silica gel pad. The pad was rinsed with EtOAc-Hex (1:1) until free of product. The filtrate was concentrated to approximately 300 mL. The precipitate was collected by filtration and washed with EtOAc-Hex (1:9) twice to give the desired indanone as a beige solid (66.75 g, 65% for three steps). MS Found: (M+Na)$^+$=367, 369.

(73d) K₂CO₃ (39.74 g, 192 mmol) was added in several batches to a suspension of the indanone from reaction 73c (66.24 g, 192 mmol) in DMSO (300 mL) cooled with a room temperature water bath. After 30 min, iodomethane (18.0 mL, 1.5 eq) was added. The mixture was stirred for 15 h, quenched with 1 N HCl (400 mL) and water (500 mL), and extracted with EtOAc-Hex (1:1, 3×400 mL). The combined extracts were washed with water (100 mL), brine (100 mL), dried (MgSO₄) and concentrated to approximately 200 mL. Hexane (200 mL) was added. Upon sitting at room temperature, light brown crystals were formed. The crystals were collected by filtration and washed with hexane (2×100 mL) to give the desired indanone (46.24 g, 67%). MS Found: (M+Na)$^+$=381, 383.

(73e) A mixture of the indanone from reaction 73d (32.06 g, 89.25 mmol), triethylsilane (250 mL), boron trifluoride etherate (250 mL) and CH₂Cl₂ (250 mL) was stirred at room temperature for 1 week, then concentrated. Silica gel chromatography (0-30% EtOAc-Hex gradient) gave the desired indane (20.01 g, 65%). MS Found: (M+Na)$^+$=367, 369.

(73f) Following a procedure similar to reaction 20e, the indane ester from reaction 73e (9.32 g, 27.0 mmol) was hydrolyzed to the corresponding acid (8.07 g, 90%). MS Found: (M+Na)=367, 369.

(73g) Following a procedure similar Example 2, the acid from reaction 73f (331 mg, 1.00 mmol) was reacted with 2-aminothiazole to give Example 73 (390 mg, 94%). MS Found: (M+H)+=413, 415.

Example 74 rac-(1R,2S)-6-bromo-2-methyl-1-phenyl-N-1,3,4-thiadiazol-2-yl-2,3-dihydro-1H-indene-2-carboxamide

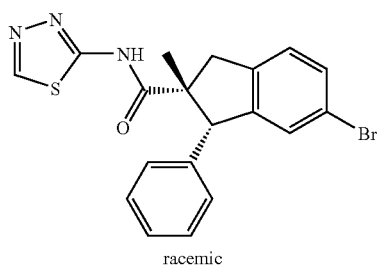

racemic

Using a procedure similar to Example 2, the acid from reaction 73f (33.5 mg, 0.101 mmol) was reacted with 2-amino-1,3,4-thiadiazole (15.3 mg, 1.5 eq) to give Example 74 (21.4 mg, 51%). MS Found: (M+H)+=414, 416.

Example 75 rac-((1R,2S)-6-bromo-2-methyl-1-phenyl-2,3-dihydro-1H-inden-2-yl)methanol

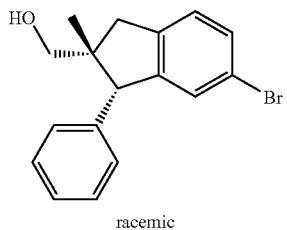

racemic

A 1 M toluene solution of DIBAL (8.1 mL, 2.5 eq) was added to a solution of the indane from reaction 73e (1.12 g, 3.24 mmol) in $CH_2Cl_2$ (30 mL) at −78° C. After 1 h at −78° C., the cold bath was removed. The mixture was quenched with 1 N HCl (100 mL) and extracted with EtOAc-Hex (1:1, 3×70 mL). The combined extracts were washed with brine, dried ($MgSO_4$) and filtered through a pad of silica gel. The silica gel pad was rinsed with EtOAc-hexane (1:1) until free of the product. The filtrate was concentrated to give Example 75 as a white solid (1.014 g, 99%).

Example 76 rac-(1R,2S,3S)-5-bromo-1-hydroxy-2-methyl-3-phenyl-N-1,3-thiazol-2-yl-2,3-dihydro-1H-indene-2-carboxamide

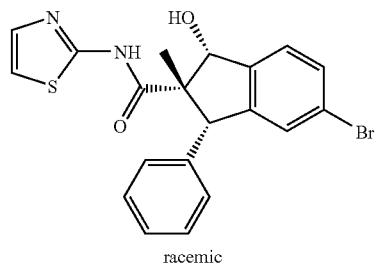

racemic (76a) $NaBH_4$ (63 mg, 5 eq) was added to a solution of the indanone from reaction 73d (119.7 mg, 0.333 mmol) in MeOH (8 mL) and $CH_2Cl_2$ (4 mL). After 1 h at room temperature, saturated $NH_4Cl$ (10 mL) was added. The volatile organic solvent was removed in vacuo. The aqueous residue was extracted with EtOAc (50 mL). The extract was washed with brine (5 mL), dried (MgSO4), concentrated and filtered through a pad of silica gel. The silica gel pad was rinsed with EtOAc-hexane (1:1) until free of product. The filtrate was concentrated to give the desired alcohol as a white solid (118.4 mg, 98%). MS Found: (M+Na)+=383, 385.

(76b-c) Following conditions similar to reactions 20e and Example 2, the alcohol from reaction 76a was hydrolyzed and reacted with 2-aminothiazole to give Example 76. MS Found: (M+H)+=429, 431.

Example 77 rac-(1R,2S)-2-methyl-1-phenyl-6-(1H-pyrazol-4-yl)-N-1,3-thiazol-2-yl-2,3-dihydro-1H-indene-2-carboxamide

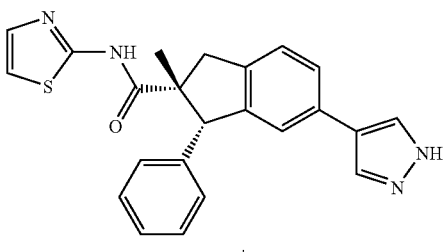

racemic

To an argon purged DMF (1 mL) solution of the iodide from Example 71 (11.6 mg, 0.025 mmol) and 4,4,5,5-tetramethyl-2-(1H-pyrazole-4-yl)-1,3,2-dioxaborolane (19.2 mg, 3.9 eq) was added a 2 M aqueous solution of $K_3PO_4$ (63 μL, 5 eq) and Pd(PPh$_3$)$_4$ (13 mg, 0.45 eq) at room temperature. The mixture was purged with argon for 10 min then sealed and microwaved (300 W) at 150° C. for 1 h. Purification by reverse-phase HPLC (50 to 90% solvent B gradient) gave Example 77 (3 mg, 30%). MS Found: (M+H)+=401.

Example 78 rac-(1R,2S)-6-azido-2-methyl-1-phenyl-N-1,3-thia-zol-2-yl-2,3-dihydro-1H-indene-2-carboxamide

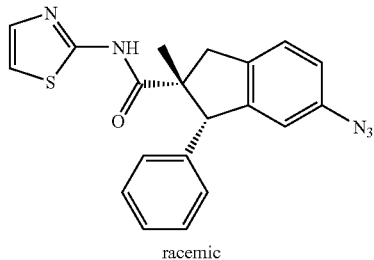
racemic

D-Proline (5.4 mg, 1 eq), NaN₃ (12.2 mg, 4 eq), 1 N solution of NaOH (0.047 mL, 1 eq) and CuI (4.5 mg, 0.5 eq) were added sequentially to the compound from Example 71 (21.7 mg, 0.047 mmol) in DMSO (1 mL) at room temperature. The resulting mixture was stirred in a 55° C. bath for 2 h. Additional CuI (10 mg) was added. After 5 h at 55° C., the mixture was quenched with saturated NH₄Cl (10 mL) and extracted with dichloromethane (2×10 mL). The combined extracts were dried (MgSO₄) and concentrated. Purification by reverse phase HPLC (80-100% solvent B gradient) provided Example 78 (5.5 mg, 31%). MS Found: $(M+H)^+=376$.

Example 79 rac-(1R,2S)-6-amino-2-methyl-1-phenyl-N-1,3-thia-zol-2-yl-2,3-dihydro-1H-indene-2-carboxamide

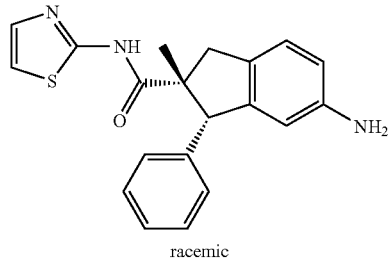
racemic

Palladium on carbon (35.7 mg) was added to a solution of the azide from Example 78 (67.3 mg, 0.179 mmol) in MeOH (4 mL) and EtOAc (4 mL). The mixture was hydrogenated under 20 psi H₂ for 4 h and filtered. The filtrate was concentrated to give Example 79 (64.5 mg, 100%). MS Found: $(M+H)^+=350$.

Example 80 rac-(1R,2S)-6-(acetylamino)-2-methyl-1-phenyl-N-1,3-thiazol-2-yl-2,3-dihydro-1H-indene-2-carboxamide

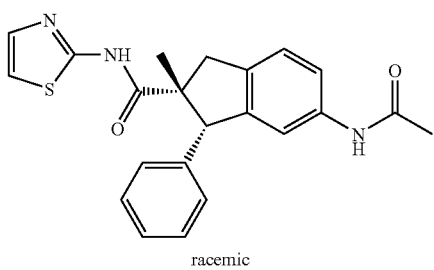
racemic

Triethylamine (24 μL, 10 eq) and acetyl chloride (4.9 μL, 4 eq) were added to a solution of the amine from Example 79 (6 mg, 0.017 mmol) in CH₂Cl₂ (1 mL). After 2 h at room temperature, the mixture was concentrated and purified by reverse-phase HPLC (70 to 100% solvent B gradient) to give Example 80 (4.4 mg, 66%). MS Found: $(M+H)^+=392$.

Examples 81 and 82 rac-(1R,2S)-2-methyl-6-((methylsulfonyl)amino)-1-phenyl-N-1,3-thiazol-2-yl-2,3-dihydro-1H-indene-2-carboxamide, and rac-(1R,2S)-6-(bis(methylsulfonyl)amino)-2-methyl-1-phenyl-N-1,3-thiazol-2-yl-2,3-dihydro-1H-indene-2-carboxamide, respectively

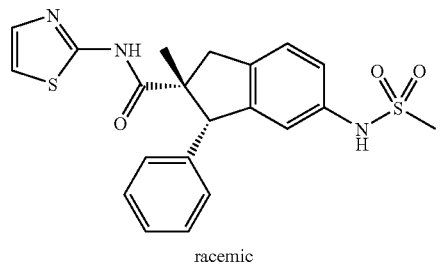
racemic

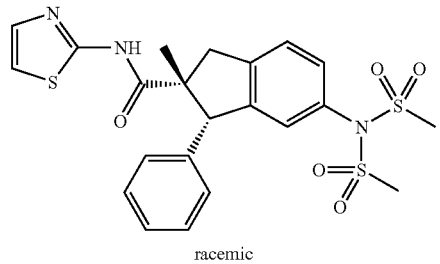
racemic

Using a procedure similar to Example 80, the amine from Example 79 was reacted with methanesulfonyl chloride to give sulfonamide Example 81 and sulfonamide Example 82. MS Found: Example 81 $(M+H)^+=428$; Example 82 $(M+H)^+=506$.

Example 83 methyl rac-((2R,3S)-2-methyl-3-phenyl-2-((1,3-thia-zol-2-ylamino)carbonyl)-2,3-dihydro-1H-inden-5-yl)carbamate

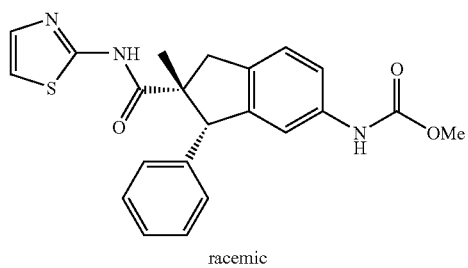
racemic

Using a procedure similar to Example 80, the amine from Example 79 (6.9 mg, 0.02 mmol) was reacted with methyl chloroformate (6 μL, 4 eq) to give Example 83 (2.7 mg, 33%). MS Found: $(M+H)^+=408$.

Example 84 rac-(1R,2S)-6-acetyl-2-methyl-1-phenyl-N-1,3-thiazol-2-yl-2,3-dihydro-1H-indene-2-carboxamide

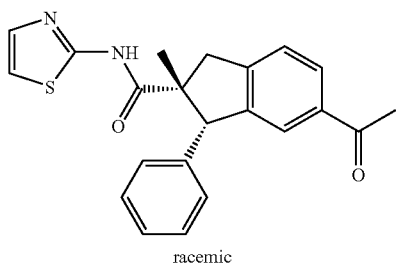

racemic (84a) A solution of the iodide from Example 71 (12.6 mg, 0.027 mmol), tributyl(1-ethoxyvinyl)tin (33.4 mg, 3.4 eq) and Pd(PPh$_3$)$_4$ (4.3 mg, 0.14 eq) in dry toluene (3 mL) was heated to reflux for 2 h under N$_2$ atmosphere. After removal of toluene in vacuo, the residue was diluted with EtOAc (15 mL) and 15% aqueous KF solution (5 mL). The organic phase was separated, dried (MgSO$_4$) and concentrated to give the crude vinyl ether (42 mg) which was contaminated with tributyltin derivatives and triphenylphosphine oxide.

(84b) A 2 N solution of HCl (0.5 mL) was added to a solution of the crude ether from reaction 84a in CH$_2$Cl$_2$ (1 mL) and MeOH (2 mL). After stirring at room temperature overnight, the mixture was concentrated and purified by reverse-phase HPLC (70-100% solvent B gradient) followed by silica gel chromatography (10%, 30% and 40% EtOAc-hexanes) to give Example 84 (1.6 mg, 16% for 2 steps). MS Found: (M+H)$^+$=377.

Example 85 rac-(1R,2S)-6-cyano-2-methyl-1-phenyl-N-1,3-thiazol-2-yl-2,3-dihydro-1H-indene-2-carboxamide

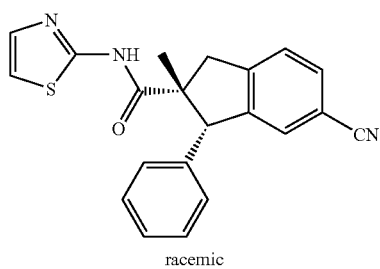

racemic

CuCN (551.8 mg, 3.9 eq) was added to a solution of the bromide from Example 73 (654.5 mg, 1.58 mmol) in DMF (10 mL). The mixture was purged with argon for 10 min then microwaved (300 W) at 220° C. for 1 h. EtOAc (100 mL), saturated NH$_4$Cl (45 mL) and ammonia (5 mL) were added. The mixture was stirred overnight at room temperature while air was bubbled through the solution. Saturated. NH$_4$Cl (50 mL) was added. The two phases were separated and aqueous phase was extracted with EtOAc (2×50 mL). The combined EtOAc extracts were washed with NH$_4$Cl (10 mL), brine (10 mL), dried (MgSO$_4$) and concentrated. Purification by reverse-phase HPLC (70-93% solvent B gradient) gave Example 85 (569.2 mg, 76%). MS Found: (M+H)$^+$=360.

Examples 86 and 87

(1R,2S)-6-cyano-2-methyl-1-phenyl-N-1,3-thiazol-2-yl-2,3-dihydro-1H-indene-2-carboxamide, and
(1S,2R)-6-cyano-2-methyl-1-phenyl-N-1,3-thiazol-2-yl-2,3-dihydro-1H-indene-2-carboxamide

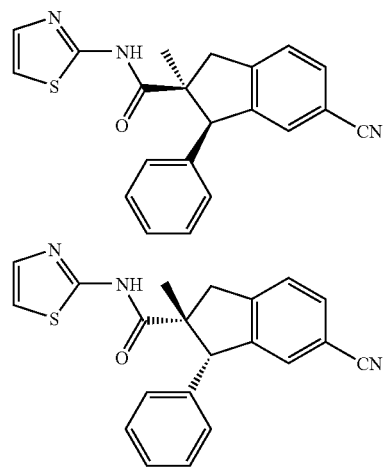

The racemic Example 85 (16.6 mg) was resolved using Chiralcel-OD HPLC column (20×500 mm, 5µ packing particle size, 2.5% MeOH—2.5% EtOH-95% Heptane, 18 mL/min) to give the fast eluting enantiomer Example 86 (3.2 mg) and the slow eluting enantiomer Example 87 (3.2 mg). MS Found: (M+H)$^+$=360.

Example 88 rac-(1R,2R)-6-cyano-2-methyl-1-phenyl-N-1,3-thiazol-2-yl-2,3-dihydro-1H-indene-2-carboxamide

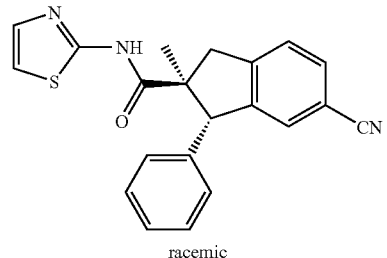

racemic

From the synthesis of Example 85, a small amount of trans-isomer Example 88 was obtained. MS Found: (M+H)$^+$=360.

Example 89 rac-(1R,2S)-6-cyano-2-methyl-1-phenyl-N-1,3,4-thiadiazol-2-yl-2,3-dihydro-1H-indene-2-carboxamide

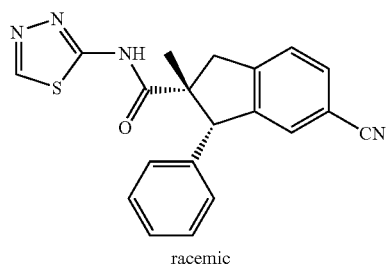

racemic (89a) Using a procedure similar to Example 85, the bromo acid from reaction 73f (193.7 mg, 0.585 mmol) was reacted with CuCN (514.4 mg, 9.8 eq) to give cyano acid (102.1 mg, 63%). MS Found: (M+H)$^+$=278.

(89b) Using a procedure similar to Example 2, the acid from reaction 89a (17 mg, 0.06 mmol) was reacted with 2-amino-1,3,4-thiadiazole to give Example 89 (16 mg, 74%). MS Found: (M+H)$^+$=361.

Example 90

(1S,2R)-6-cyano-2-methyl-1-phenyl-N-1,3,4-thiadiazol-2-yl-2,3-dihydro-1H-indene-2-carboxamide

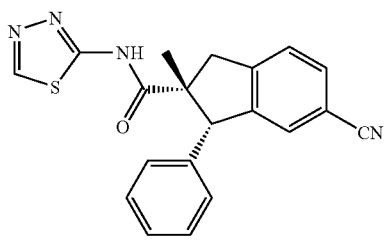

(90a) The bromo acid from reaction 73f (3.00 g) was resolved on chiral SFC-HPLC (5% MeOH—95% CO$_2$, 60 mL/min, Chiralcel OJ column, 30×500 mm) to give a fast eluting enantiomer (1.10 g) and a slow eluting enantiomer (1.37 g).

(90b) Using a procedure similar to Example 85, the slow eluting enantiomer from 90a (230.5 mg, 0.696 mmol) was reacted with CuCN (353 mg, 5.6 eq) to give the desired cyano acid (122.9 mg, 64%).

(90c) Using a procedure similar to Example 2, the acid from reaction 90b (17 mg, 0.06 mmol) was reacted with 2-amino-1,3,4-thiadiazole to give Example 90 (16 mg, 74%). MS Found: (M+H)$^+$=361.

Example 91 rac-(1R,2S)-6-cyano-2-methyl-1-phenyl-N-(5-(trifluoromethyl)-1,3,4-thiadiazol-2-yl)-2,3-dihydro-1H-indene-2-carboxamide

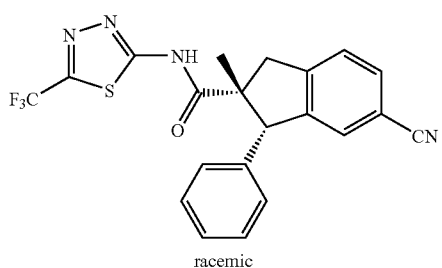

racemic

Using a procedure similar to Example 2, the acid from reaction 89a (14 mg, 0.0505 mmol) was reacted with 2-amino-5-trifluoromethyl-1,3,4-thiadiazole to give Example 91 (11.5 mg, 53%). MS Found: (M+H)$^+$=429.

Example 92 rac-(1R,2S)-6-cyano-2-methyl-N-(5-methyl-1,3,4-thiadiazol-2-yl)-1-phenyl-2,3-dihydro-1H-indene-2-carboxamide

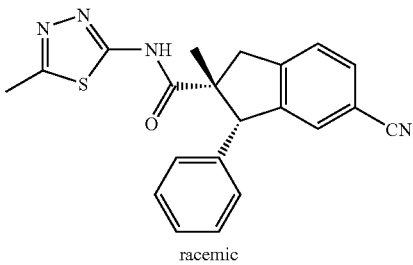

racemic

Using a procedure similar to Example 2, the acid from reaction 89a (14 mg, 0.0505 mmol) was reacted with 2-amino-5-methyl-1,3,4-thiadiazole to give Example 92 (16.2 mg, 86%). MS Found: (M+H)$^+$=375.

Example 93 rac-(1R,2S)-6-cyano-2-methyl-1-phenyl-N-1,2,4-thiadiazol-5-yl-2,3-dihydro-1H-indene-2-carboxamide

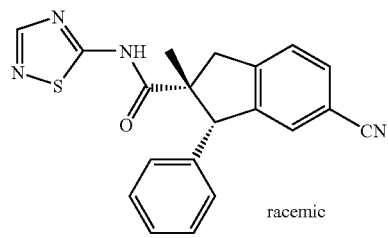

racemic

Using a procedure similar to Example 2, the acid from reaction 89a (18 mg, 0.0649 mmol) was reacted with 5-amino-1,2,4-thiadiazole to give Example 93 (16.2 mg, 74%). MS Found: (M+H)$^+$=361.

Example 94 rac-(1R,2S)-6-cyano-2-methyl-N-(3-methyl-1,2,4-thiadiazol-5-yl)-1-phenyl-2,3-dihydro-1H-indene-2-carboxamide

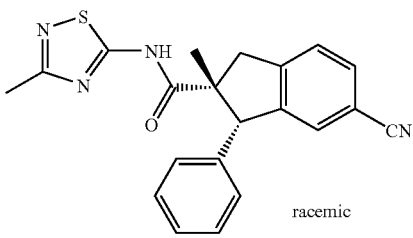

racemic

Using a procedure similar to Example 2, the acid from reaction 89a (14 mg, 0.0505 mmol) was reacted with 5-amino-3-methyl-1,2,4-thiadiazole to give Example 94 (12.2 mg, 65%). MS Found: (M+H)$^+$=375.

Example 95 rac-(1R,2S)-6-cyano-2-methyl-N-(methylsulfonyl)-1-phenyl-2,3-dihydro-1H-indene-2-carboxamide

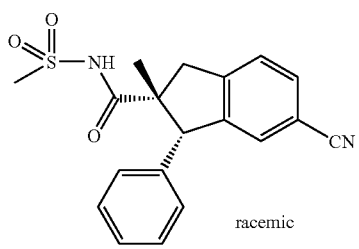

racemic

Using a procedure similar to Example 2, the acid from reaction 89a (16.2 mg, 0.058 mmol) was reacted with methanesulfonamide to give Example 95 (8.1 mg, 39%). MS Found: (M+H)$^+$=355.

Example 96 rac-(1R,2S)-6-cyano-2-methyl-1-phenyl-N-(phenylsulfonyl)-2,3-dihydro-1H-indene-2-carboxamide

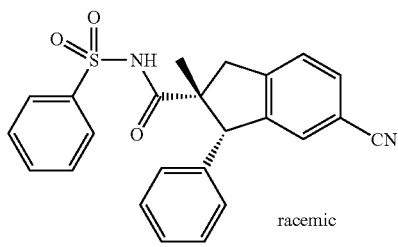

racemic

Using a procedure similar to Example 2, the acid from reaction 89a (13.1 mg, 0.047 mmol) was reacted with benzenesulfonamide to give Example 96 (7.2 mg, 37%). MS Found: (M+H)$^+$=417.

Example 97 rac-(1R,2S)-2-methyl-1-phenyl-6-(1H-tetrazol-5-yl)-N-1,3-thiazol-2-yl-2,3-dihydro-1H-indene-2-carboxamide

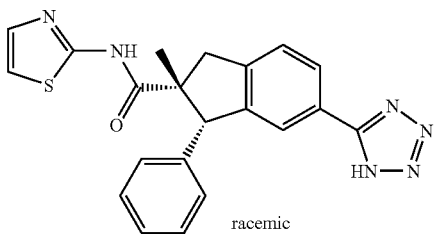

racemic

Trimethyltin azide (63.4 mg, 6 eq) was added to a solution of the compound from Example 88 (23.5 mg, 0.050 mmol) in xylene (10 mL). The mixture was heated to reflux for 18 h, concentrated and purified by reverse phase HPLC (70-100% solvent B gradient) to give Example 91 as a white solid (17.2 mg, 86%). MS Found: (M+H)$^+$=403.

Examples 98 and 99 rac-(2R,3S)-2-methyl-3-phenyl-N~2~-1,3-thiazol-2-yl-2,3-dihydro-1H-indene-2,5-dicarboxamide, and rac-(2R,3S)-2-methyl-3-phenyl-2-((1,3-thiazol-2-ylamino)carbonyl)-2,3-dihydro-1H-indene-5-carboxylic acid, respectively

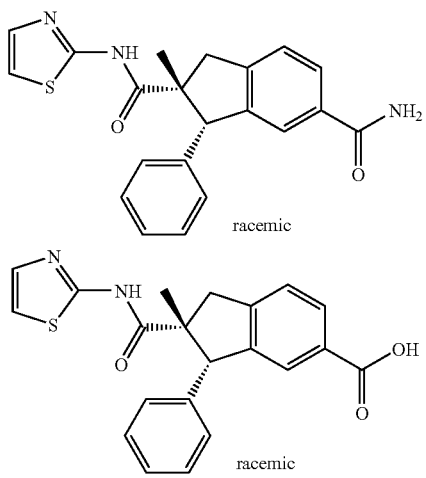

racemic racemic

A 2 N solution of KOH (2 mL) was added to a solution of the compound from Example 88 (194 mg, 0.410 mmol) in ethanol (2 mL). The mixture was microwaved at 140° C. for 10 min, quenched with 1 N HCl (10 mL) and diluted with EtOAc (30 mL). The solid was collected by filtration, washed with water, MeOH, and dichloromethane to give the amide, Example 98 (63.6 mg, 41%). MS Found: (M+H)$^+$=378.

The biphasic filtrate was separated. The organic layer was concentrated and purified by reverse phase HPLC (70-100% solvent B gradient) to give the acid, Example 99, as a white solid (14.6 mg, 9%). MS Found: (M+H)$^+$=379.

Example 100 rac-(2R,3S)—N~5~,N~5~,2-trimethyl-3-phenyl-N~2~-1,3-thiazol-2-yl-2,3-dihydro-1H-indene-2,5-dicarboxamide

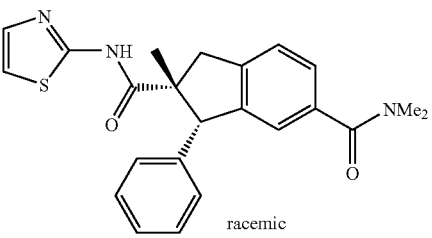

racemic

Using a procedure similar to Example 2, the material from Example 99 (10.8 mg, 0.0285 mmol) was reacted with dimethylamine to give Example 100 (10.1 mg, 87%). MS Found: (M+H)+=406.

Example 101

((1R,2S)-6-cyano-2-methyl-1-phenyl-2,3-dihydro-1H-inden-2-yl)methyl rac-phenylcarbamate

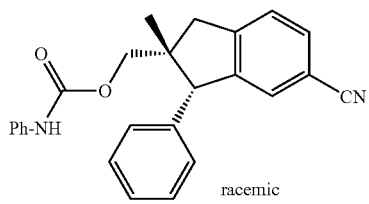

racemic (10a) Lithium aluminum hydride (1.22 g, 2.3 eq) was added to a solution of the ester from reaction 20d (4.39 g, 14.14 mmol) in THF (150 mL) at room temperature. The mixture was heated at reflux for 30 min, cooled to room temperature, quenched with 0.4 N NaOH (50 mL) and water (250 mL). The suspension was filtered through celite. The filter bed was washed with EtOAc (100 mL). The biphasic filtrate was separated. The aqueous layer was extracted with EtOAc (200 mL). The combined organic phase was dried (MgSO4) and concentrated to give the desired alcohol as a white solid (3.73 g, 98%). MS Found: (M+Na)+=291.

(10f b) Using a procedure similar to the synthesis of Example 5, the product from reaction 101a (3.73 g, 13.9 mmol) was converted to the phenol (3.53 g, 97%). MS Found: (M+Na)+=277.

(101c) Triethylamine (15 mL, 7.8 eq) was added to a suspension of 2-[N,N-bis(trifluoromethylsulfonyl)amino]pyridine (14.95 g, 3 eq) and the phenol from reaction 101b (3.53 g, 13.88 mmol) in CH2Cl2 (50 mL). After stirring at room temperature for 2 h, the mixture was concentrated and redissolved in EtOAc (200 mL), washed with 1 N HCl (2×100 mL), brine (20 mL), dried (MgSO4) and concentrated. Silica gel chromatography (30% EtOAc-hexanes) gave the desired triflate (3.97 g, 74%).

(101d) A solution of the triflate from 101c (3.97 g, 10.27 mmol), zinc cyanide (3.61 g, 3 eq), Pd2(bda)3 (0.538 g, 5.7 mol %), dppf (0.667 g, 11.7 mol %) and zinc powder (41 mg, 6 mol %) in N,N-dimethylacetamide (50 mL) was degassed and sealed in a pressure flask. The mixture was heated at 80° C. for 2 h. After cooling, the mixture was diluted with EtOAc (150 mL) and saturated NH4Cl (100 mL). The aqueous phase was extracted with EtOAc (50 mL). The combined organic phase was washed with brine (20 mL), dried (MgSO4) and concentrated. Silica gel chromatography (30% EtOAc-hexanes) gave the cyano alcohol (1.67 g, 62%). MS Found: (M+H)+=264.

(101e) Using a procedure similar to the synthesis of Example 32, the cyano alcohol from 101d (8.9 mg, 0.03 mmol) was reacted with phenyl isocyanate (20 μL, 6 eq) to give Example 101 (9.8 mg, 83%). MS Found: (M+Na)=405.

Examples 102 and 103 rac-(2R,3S)-2-((R)-hydroxy(2-thienyl)methyl)-2-methyl-3-phenyl-2,3-dihydro-1H-indene-5-carbonitrile; and (2R,3S)-2-((S)-hydroxy(2-thienyl)methyl)-2-methyl-3-phenyl-2,3-dihydro-1H-indene-5-carbonitrile

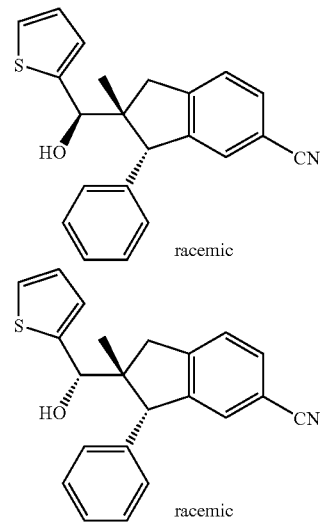

racemic racemic (102a) Dess-Martin periodinane (5.03 g, 2.2 eq) was added to a solution of the cyano alcohol from 101d (1.42 g, 5.39 mmol) in CH2Cl2 (20 mL). After stirring at room temperature for 1.5 h, the mixture was concentrated and purified by silica gel chromatography (30% EtOAc-hexanes) to give the desired aldehyde (0.49 g, 38%) as a yellow oil. MS Found: (M+H)+=262.

(102b) A 1 M THF solution of thiophen-2-ylmagnesium bromide (0.1 mL, 1.5 eq) was added to a solution of the aldehyde from 102a (17 mg, 0.065 mmol) in THF (2 mL) at 0° C. After stirring at 0° C. for 1 h, the mixture was concentrated and purified by reverse-phase HPLC (80-100% solvent B gradient) to give the fast eluting diastereomer as Example 102 (9.3 mg, 31%) and a 24:76 mixture of fast and slow eluting diastereomers as Example 103 (4.7 mg, 16%). MS Found: (M+H)+=346.

Example 104 rac-(2R,3S)-2-methyl-3-phenyl-2-(2-thienylcarbonyl)-2,3-dihydro-1H-indene-5-carbonitrile

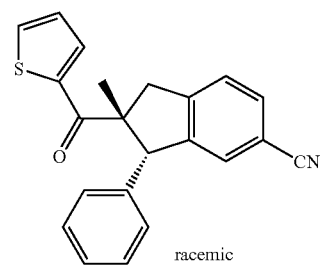

racemic

Using a procedure similar to reaction 102a, a mixture of Examples 102 and 103 (8.7 mg, 0.019 mmol) was oxidized to give Example 104 (4.6 mg, 53%). MS Found: (M+Na)+=366.

Examples 105 and 106 rac-(2R,3S)-2-((R)-hydroxy(3-thienyl)methyl)-2-methyl-3-phenyl-2,3-dihydro-1H-indene-5-carbonitrile; and (2R,3S)-2-((S)-hydroxy(3-thienyl)methyl)-2-methyl-3-phenyl-2,3-dihydro-1H-indene-5-carbonitrile

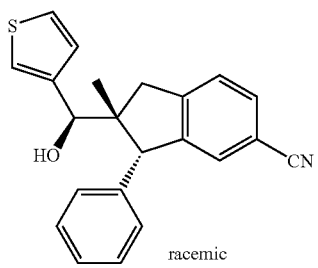

racemic

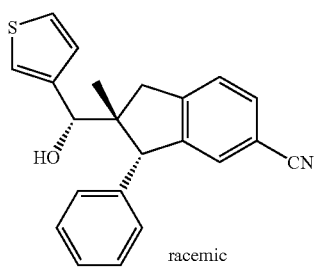

racemic

Using a procedure similar to reaction 102b, the aldehyde from 102a (17.9 mg, 0.069 mmol) was reacted with a 0.5 M THF solution of thiophen-3-ylmagnesium iodide (0.21 mL, 1.5 eq) to give the fast eluting diastereomer as Example 105 (7.6 mg, 24%) and a 29:71 mixture of fast and slow eluting diastereomers as Example 106 (5 mg, 16%). MS Found: (M+H)$^+$=346.

Example 107 rac-(2R,3S)-2-methyl-3-phenyl-2-(3-thienylcarbonyl)-2,3-dihydro-1H-indene-5-carbonitrile

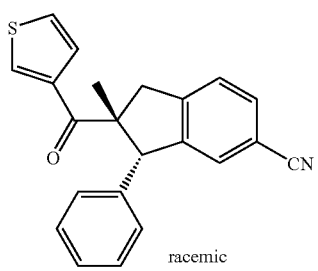

racemic

Using a procedure similar to reaction 102a, a mixture of Examples 105 and 106 (5.7 mg, 0.012 mmol) was oxidized to give the Example 107 (3.3 mg, 58%). MS Found: (M+Na)$^+$=366.

Examples 108 and 109 rac-(2R,3S)-2-((R)-hydroxy(1,3-thiazol-2-yl)methyl)-2-methyl-3-phenyl-2,3-dihydro-1H-indene-5-carbonitrile; and (2R,3S)-2-((R)-hydroxy(1,3-thiazol-2-yl)methyl)-2-methyl-3-phenyl-2,3-dihydro-1H-indene-5-carbonitrile

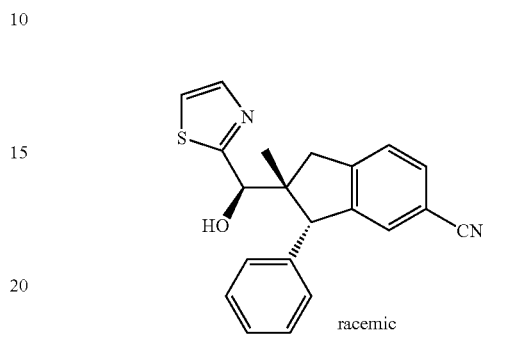

racemic

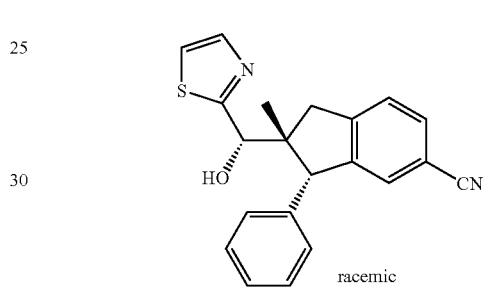

racemic

The aldehyde from 102a (22.2 mg, 0.085 mmol) was mixed with 2-trimethylsilylthiazole (140 µL, 10 eq) and a 1 M THF solution of tetrabutylammonium fluoride (0.5 mL, 5.9 eq). After stirring at room temperature for 3 h, the mixture was concentrated and purified by reverse-phase HPLC (70-100% solvent B gradient) to give the fast eluting diastereomer as Example 108 (2.7 mg, 6.9%) and a 1:9 mixture of fast and slow eluting diastereomers as Example 109 (1.4 mg, 3.6%). MS Found: (M+H)$^+$=347.

Example 110

2-(2-phenyl-2,3-dihydro-1H-inden-2-yl)-N-(4-((4-(4-pyridinyl)phenyl)methyl)-1,3-thiazol-2-yl)acetamide

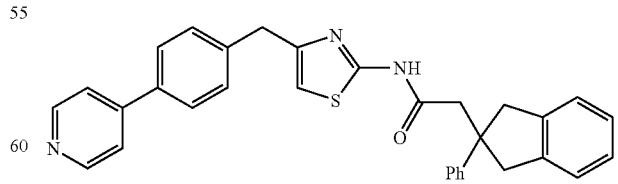

Using a procedure similar to the synthesis of Example 2, the acid from reaction Ic (12.6 mg, 0.050 mmol) was reacted with 2-amino-4-(4-(pyridin-4-yl)benzyl)thiazole to give Example 110 (9.5 mg, 31%). MS Found: (M+H)$^+$=502.

Examples 111 and 112 rac-(2R,3S)-2-((4R)-2,5-dioxo-4-imidazolidinyl)-2-methyl-3-phenyl-2,3-dihydro-1H-indene-5-carbonitrile; and (2R,3S)-2-((4S)-2,5-dioxo-4-imidazolidinyl)-2-methyl-3-phenyl-2,3-dihydro-1H-indene-5-carbonitrile

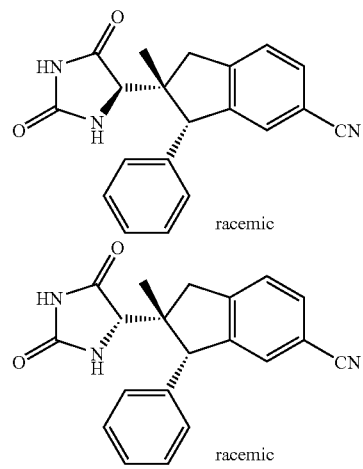

racemic racemic

A solution of the aldehyde from 102a (17.8 mg, 0.068 mmol), KCN (8 mg, 1.8 eq) and (H$_4$)$_2$CO$_3$ (80 mg, 12 eq) in ethanol (1 mL) and water (1 mL) was heated at 80° C. in a sealed tube for 6 h. Purification by reverse-phase HPLC (65-95% solvent B gradient) gave the fast diastereomer as Example 111 (3.7 mg, 12%) and the slow diastereomer as Example 112 (15.3 mg, 50%). MS Found: (M+H)$^+$=332.

Example 113 rac-(2R,3S)-2-methyl-3-phenyl-2-(1H-pyrazol-5-yl)-2,3-dihydro-1H-indene-5-carbonitrile

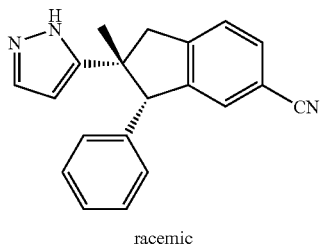

racemic (113a) A solution of diethylphosphorylacetalaldehyde diethylacetal (11.30 mL, 1.05 eq) and p-toluenesulfonyl hydrazide (8.27 g, 44.4 mmol) in 0.1 N aqueous HCl (20 mL) was heated at 75° C. for 2 h then cooled to room temperature. A crystalline solid was formed and collected by filtration. The solid was washed with cold water and ether to give the desired hydrazone intermediate (12.58 g, 81%).

(113b) The hydrazone from reaction 113a (55.6 mg, 2 eq) in THF (4 mL) was added to a suspension of NaH (60% mixture with mineral oil, 12 mg, 3.8 eq) in THF (4 mL) at 0° C. After stirring for 45 min at 0° C., the aldehyde from 102a (20.8 mg, 0.08 mmol) in THF (2 mL) was added. After 1 h at 0° C. and 2.5 h at reflux, the mixture was concentrated and purified by reverse-phase HPLC (70-100% solvent B gradient) to give Example 113 as a 1:1 mixture of tautomers (6.4 mg, 19%). MS Found: (M+H)$^+$=300.

Example 114 rac-(2R,3S)-2-(3-aminoimidazo[1,2-a]pyridin-2-yl)-2-methyl-3-phenyl-2,3-dihydro-1H-indene-5-carbonitrile

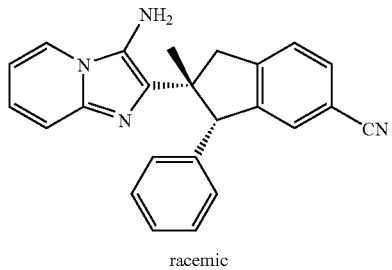

racemic

A solution of 2-aminopyridine (9 mg, 1 eq), scandium triflate (3.1 mg, 0.04 eq), 1,1,3,3-tetramethylbutylisonitrile (20 μL, 1.1 eq) and the aldehyde from 102a (24.5 mg, 0.094 mmol) in MeOH (1 mL) was microwaved at 160° C. for 20 min. The mixture was diluted with MeOH (10 mL) and filtered. The filtrate was concentrated, re-dissolved in dichloromethane (1 mL), and treated with TFA (0.4 mL). After 1 h at room temperature, the mixture was concentrated and purified by reverse-phase HPLC (50-80% solvent B gradient) to give Example 114 (11.5 mg, 21%). MS Found: (M+H)$^+$=365.

Example 115 methyl rac-(2E)-3-((1R,2R)-6-cyano-2-methyl-1-phenyl-2,3-dihydro-1H-inden-2-yl)-2-propenoate

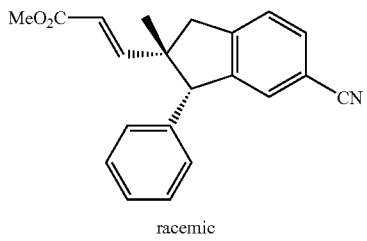

racemic

A mixture of the aldehyde from 102a (16.0 mg, 0.061 mmol) and methyl (triphenylphosphoranylidene)acetate (30.6 mg, 1.5 eq) in toluene (8 mL) was heated to reflux for 3 h and concentrated. Reverse phase HPLC (80-100% solvent B gradient) gave Example 115 (4.4 mg, 23%).

Example 116 rac-N-((1R,2S)-6-cyano-2-methyl-1-phenyl-2,3-dihydro-1H-inden-2-yl)-1,3-thiazole-2-carboxamide

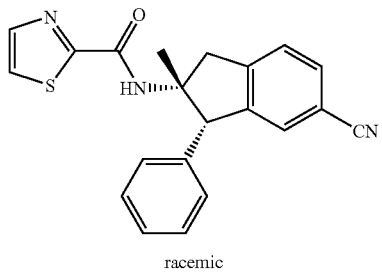

racemic (116a) Diphenylphosphoryl azide (127 µL, 1.2 eq) was added to a solution of the cyano acid from 89a (132.3 mg, 0.477 mmol) and triethylamine (200 µL, 3 eq) in toluene (5 mL). After stirring at room temperature overnight, benzyl alcohol (100 µL, 2 eq) was added. The mixture was heated at 120° C. for 16 h, concentrated and purified by silica gel chromatography (0-50% EtOAc-hexanes gradient) to give the Cbz-protected amine as a white solid (133.3 mg, 73%). MS Found: (M+Na)$^+$=405.

(116b) Palladium on carbon (10 wt %, 36 mg) was added to a solution of the CBz-protected amine from 116a (133 mg, 0.348 mmol) in MeOH (6 mL) and EtOAc (6 mL) under nitrogen atmosphere. The mixture was purged with hydrogen and stirred under balloon pressure hydrogen for 30 h. The catalyst was removed by filtration. The filtrate was concentrated and purified by reverse-phase HPLC (40-70% solvent B gradient) to give the desired amine as a TFA salt (140 mg, 90%). MS Found: (M+H)$^+$=249.

(116c) A 2 N aqueous solution of KOH (3.5 mL, 5 eq) was added to ethyl thiazole-2-carboxylate (213 mg, 1.355 mmol) in ethanol (3 mL). After 2 h at room temperature, the mixture was acidified with 2 N HCl (3.5 mL). Upon sitting overnight, a needle crystal was formed, which was collected by filtration to give thiazole-2-carboxylic acid (43.3 mg, 25%).

(116d) Using a procedure similar to Example 2, the amine from 116b (14.1 mg, 0.039 mmol) was reacted with thiazole-2-carboxylic acid from 116c (7.5 mg, 1.5 eq) to give Example 116 (8.7 mg, 47%). MS Found: (M+H)$^+$=360.

Example 117 rac-1-((1R,2S)-6-cyano-2-methyl-1-phenyl-2,3-dihydro-1H-inden-2-yl)-3-(1,3-thiazol-2-yl)urea

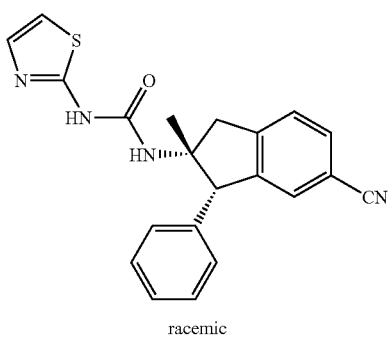

racemic

Diphenylphosphoryl azide (11 µL, 2 eq) was added to the cyano acid from 89a (10.2 mg, 0.026 mmol) and triethylamine (20 µL, 5.5 eq) in toluene (1.5 mL). After stirring at room temperature overnight, 2-aminothiazole (110.3 mg, 4 eq) was added. The mixture was heated at 100° C. for 3 h, concentrated and purified by reverse-phase HPLC (65-100% solvent B gradient) to give Example 117 (7 mg, 72%). MS Found: (M+H)$^+$=375.

Example 118

Nrac-N-((1R,2S)-6-cyano-2-methyl-1-phenyl-2,3-dihydro-1H-inden-2-yl)-2-thiophenecarboxamide

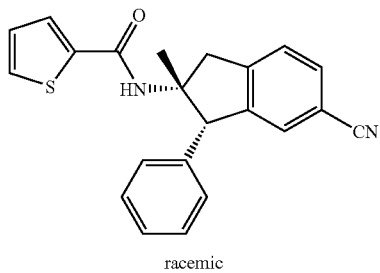

racemic

Using a procedure similar to Example 2, the amine from 116b (6.5 mg, 0.018 mmol) was reacted with 2-thiophenecarboxylic acid (10 mg, 4.3 eq) to give Example 118 (4.3 mg, 67%). MS Found: (M+H)$^+$=359.

Example 119 rac-N-((1R,2S)-6-cyano-2-methyl-1-phenyl-2,3-dihydro-1H-inden-2-yl)-2-(2-thienyl)acetamide

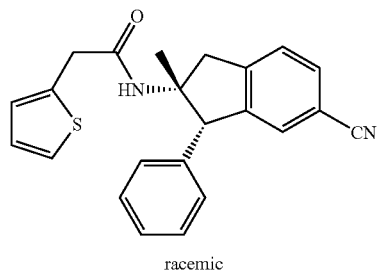

racemic

Using a procedure similar to Example 2, the amine from 116b (9.4 mg, 0.026 mmol) was reacted with 2-thiopheneacetic acid (5.7 mg, 1.5 eq) to give Example 119 (6.2 mg, 64%). MS Found: (M+H)$^+$=373.

Example 120 rac-1-((1R,2S)-6-cyano-2-methyl-1-phenyl-2,3-dihydro-1H-inden-2-yl)-3-phenylurea

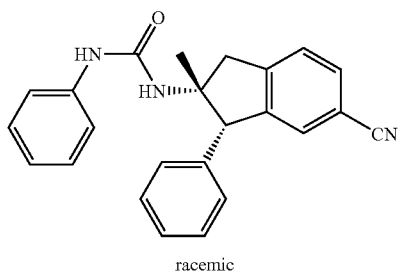

racemic

Using a procedure similar to Example 80, the amine from 116b (7.7 mg, 0.021 mmol) was reacted with phenyl isocyanate (4.6 µL, 2 eq) to give Example 120 (6 mg, 77%). MS Found: (M+H)$^+$=368.

Example 121 rac-N-(((1R,2S)-6-cyano-2-methyl-1-phenyl-2,3-dihydro-1H-inden-2-yl)methyl)acetamide

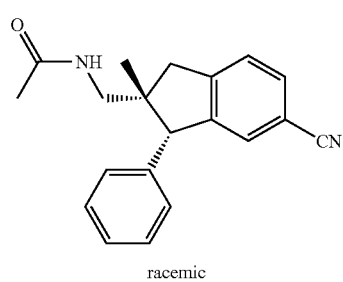

racemic (121a) A solution of the cyano alcohol from 101d (114.6 mg, 0.40 mmol), methanesulfonyl chloride (62 µL, 2 eq) and triethylamine (223 µL, 4 eq) in $CH_2Cl_2$ (3 mL) was stirred at room temperature for 16 h. The mixture was concentrated and purified by silica gel chromatography (0-50% EtOAc-hexanes gradient) to give the mesylate (155.4 mg) contaminated with trace of EtOAc.

(121b) A solution of the mesylate from 121a (155.4 mg, 0.40 mmol maximum) and sodium azide (124.5 mg, 4.8 eq) in DMSO (2 mL) was heated at 80° C. for 21 h. The mixture was quenched with water (5 mL) and extracted with EtOAc (100 mL). The organic phase was dried ($MgSO_4$), concentrated and purified by silica gel chromatography (0-30% EtOAc-hexanes gradient) to give the azide (94.3 mg, 82% for two steps). MS Found: $(M+H)^+=289$.

(121c) Using a procedure similar to reaction 116b, the azide from 121b (94.3 mg, 0.327 mmol) was hydrogenated to give the amine (40.4 mg, 47%). MS Found: $(M+H)^+=263$.

(121d) Using a procedure similar to Example 80, the amine from 121c (6.2 mg, 0.024 mmol) was reacted with acetyl chloride to give Example 121 (2.9 mg, 40%). MS Found: $(M+H)^+=305$.

Example 122 rac-N-(((1R,2S)-6-cyano-2-methyl-1-phenyl-2,3-dihydro-1H-inden-2-yl)methyl)-2,2,2-trifluoroacetamide

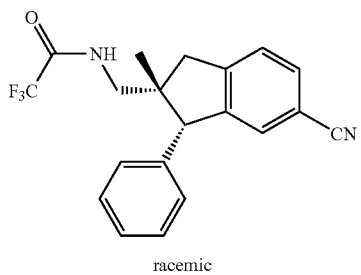

racemic

Using a procedure similar to Example 80, the amine from 121c (7.6 mg, 0.029 mmol) was reacted with trifluoroacetic anhydride to give Example 122 (3.1 mg, 30%). MS Found: $(M+H)^+=359$.

Example 123 rac-N-(((1R,2S)-6-cyano-2-methyl-1-phenyl-2,3-dihydro-1H-inden-2-yl)methyl)-1,3-thiazole-2-carboxamide

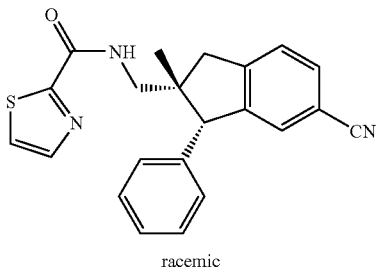

racemic

Using a procedure similar to Example 2, the amine from 121c (6 mg, 0.023 mmol) was reacted with thiazole-2-carboxylic acid from 116c (7.2 mg, 2.4 eq) to give Example 123 (4.6 mg, 54%). MS Found: $(M+H)^+=374$.

Example 124

N-(4-(3-(((3-chloro-4-(methyloxy)phenyl)amino)carbonyl)phenyl)-1,3-thiazol-2-yl)-2,3-dihydro-1H-indene-1-carboxamide

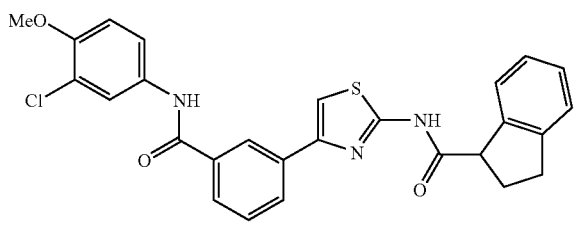

(124a) A MeOH (1 mL) solution of 3-oxo-indancarboxylic acid (85.5 mg, 0.485 mmol) was mixed with Pd/C (16.5 mg) and hydrogenated at room temperature under 55 psi $H_2$ pressure for 18 h. The crude mixture was filtered and concentrated to give 1-indanecarboxylic acid (74.4 mg, 95%). MS Found: $(M-H)^-=161$.

(124b) Using a procedure similar to the synthesis of Example 2, the acid from reaction 124a (17 mg, 0.1 mmol) was reacted with 3-(2-aminothiazol-4-yl)-N-(3-chloro-4-methoxyphenyl)benzamide to give Example 124. MS Found: $(M+H)^+=504$.

Example 125 rac-N-((1R,2S)-6-cyano-2-methyl-1-phenyl-2,3-dihydro-1H-inden-2-yl)methanesulfonamide

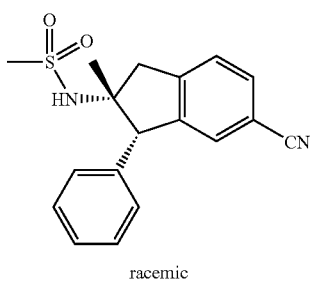

racemic

Using a procedure similar to Example 80, the amine from 116b (10 mg, 0.028 mmol) was reacted with methanesulfonyl chloride (4.2 µL, 2 eq) to give Example 125 (2.4 mg, 26%). MS Found: $(M+Na)^+=349$.

Example 126 rac-N-((1R,2S)-6-cyano-2-methyl-1-phenyl-2,3-dihydro-1H-inden-2-yl)-2,2,2-trifluoroacetamide

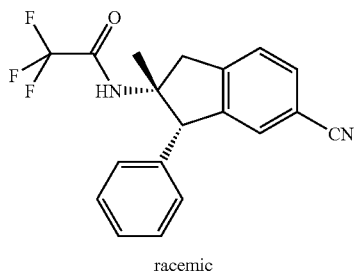

racemic

Using a procedure similar to Example 80, the amine from 116b (10 mg, 0.028 mmol) was reacted with trifluoroacetic anhydride (7.8 μL, 2 eq) to give Example 126 (1.5 mg, 16%). MS Found: $(M+Na)^+=367$.

Example 127

(1S,2R)-6-cyano-N-ethyl-2-methyl-1-phenyl-2,3-dihydro-1H-indene-2-carboxamide

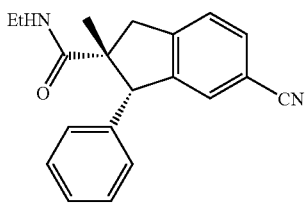

To a solution of BOP (38 mg, 2 eq), HOBt (8.2 mg, 1.5 eq) and the chiral acid from reaction 90b (11.5 mg, 0.04 mmol) in DMF (1 mL) was bubbled in ethylamine for 5 min. The reaction vial was sealed and heated at 60° C. for 2 h. The crude mixture was purified by reverse-phase HPLC (70-100% solvent B gradient) followed by silica gel chromatography (0-80% EtOAc-Hexanes gradient) to give Example 127 (9.3 mg, 74%). MS Found: $(M+H)^+=305$.

Example 128

(1S,2R)-6-cyano-N,N,2-trimethyl-1-phenyl-2,3-dihydro-1H-indene-2-carboxamide

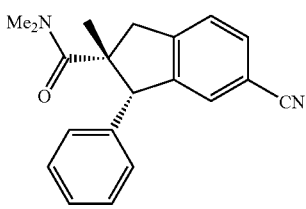

Using a procedure similar to Example 127, the chiral acid from 90b (11.5 mg, 0.04 mmol) was reacted with a 2 M THF solution of dimethylamine (0.41 mL, 20 eq) to give Example 128 (9.2 mg, 73%). MS Found: $(M+H)^+=305$.

Example 129 rac-N-((1R,2S)-6-cyano-2-methyl-1-phenyl-2,3-dihydro-1H-inden-2-yl)-2,2,3,3,3-pentafluoropropanamide

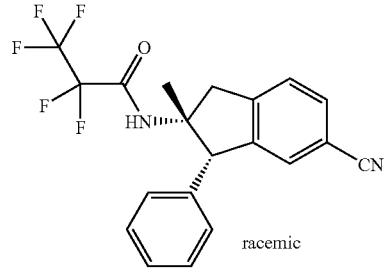

racemic

Using a procedure similar to Example 80, the amine from 116b (5.4 mg, 0.015 mmol) was reacted with pentafluoropropionic anhydride (4.7 μL, 1.6 eq) to give Example 129 (1.1 mg, 18%). MS Found: $(M-NHCOCF_2CF_3)^+=232$.

Example 130 rac-2-((1R,2S)-6-bromo-2-methyl-1-phenyl-2,3-dihydro-1H-inden-2-yl)-1,3-benzothiazole

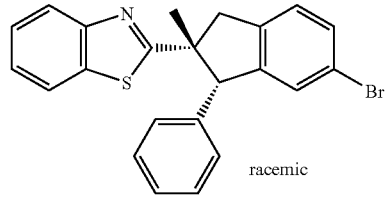

racemic (130a) DMF (120 μL) was added dropwise to a solution of the bromo acid from 73f (66 mg, 0.2 mmol) and oxalyl chloride (2 M in $CH_2Cl_2$, 200 μL) in $CH_2Cl_2$ (3 mL) at room temperature. The mixture was stirred overnight and concentrated to give the crude acyl chloride.

(130b) A toluene (1 mL) solution of the crude acyl chloride from reaction 130a (maximum 0.05 mmol) and 2-aminothiophenol (6.42 μL, 1.2 eq) was heated at 150° C. for 2 h in a sealed tube. The mixture was concentrated and purified by reverse-phase HPLC (90-100% solvent B gradient) to give Example 130 (11.9 mg, 57%). MS Found: $(M+H)^+=420, 422$.

Example 131 rac-2-((1R,2S)-6-bromo-2-methyl-1-phenyl-2,3-dihydro-1H-inden-2-yl)-1H-benzimidazole

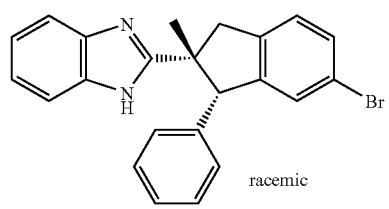

racemic

Following a procedure similar to reaction 130b, the crude acyl chloride from 130a (maximum 0.05 mmol) was reacted with 1,2-phenylenediamine to give Example 131 (2.9 mg, 14%). MS Found: $(M+H)^+=403, 405$.

Example 132 rac-2-((1R,2S)-6-bromo-2-methyl-1-phenyl-2,3-dihydro-1H-inden-2-yl)-3H-imidazo[4,5-b]pyridine

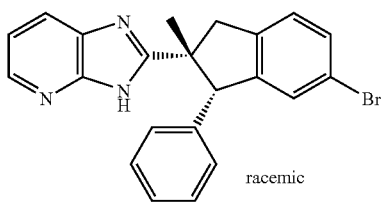
racemic

The crude acyl chloride from reaction 130a (maximum 0.04 mmol) and 2,3-diaminopyridine (4 mg, 1 eq) in 1-methyl-2-pyrrolidinone (1 mL) was microwaved at 230° C. for 20 min. The mixture was concentrated and purified by reverse-phase HPLC (70-100% solvent B gradient) to give Example 132 (3.9 mg, 26%). MS Found: (M+H)$^+$=404, 406.

Example 133 rac-(1R,2S)-2,6-dimethyl-1-phenyl-N-1,3-thiazol-2-yl-2,3-dihydro-1H-indene-2-carboxamide

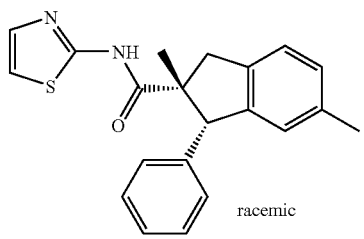
racemic

A solution of trimethylboroxine (40 µL, 4.8 eq), K$_2$CO$_3$ (38 mg, 4.7 eq), Pd(PPh$_3$)$_4$ (18 mg, 0.26 eq) and Example 73 (24.5 mg, 0.06 mmol) in dioxane (1 mL) was purged with argon for 10 min. The reaction vial was sealed and microwaved at 170° C. for 10 min. The mixture was purified by reverse-phase HPLC (90-100% solvent B gradient) to give Example 133 (7.4 mg, 36%). MS Found: (M+H)$^+$=349.

Example 134 rac-(1R,2S)-2,6-dimethyl-1-phenyl-N-1,3,4-thiadiazol-2-yl-2,3-dihydro-1H-indene-2-carboxamide

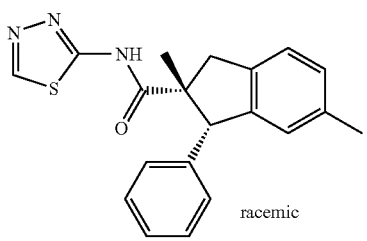
racemic (134a) Using a procedure similar to Example 133, the bromoindane ester from 73e (97.6 mg, 0.283 mmol) was reacted with trimethylboroxine (110 µL, 2.8 eq) to give methylindane ester (36 mg, 46%). MS Found: (M-CO$_2$Me)$^+$=221.

(134b) Following a procedure similar to reaction 20e, the methylindane ester from reaction 134a (36 mg, 0.128 mmol) was hydrolyzed to the corresponding acid (34 mg, 99%). MS Found: (M–H)$^-$=265.

(134c) Following a procedure similar to Example 2, the acid from reaction 134b (20 mg, 0.075 mmol) was reacted with 2-amino-1,3,4-thiadiazole to give Example 134 (16.9 mg, 65%). MS Found: (M+H)$^+$=350.

Example 135 rac-(1R,2S)-2-methyl-1,6-diphenyl-N-1,3-thiazol-2-yl-2,3-dihydro-1H-indene-2-carboxamide

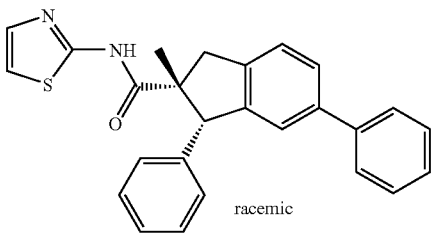
racemic

A solution of Example 73 (30 mg, 0.073 mmol), phenylboronic acid (25.2 mg, 2.8 eq), Pd(PPh$_3$)$_4$ (12.8 mg, 0.15 eq) and 2 M aqueous K$_3$PO$_4$ (0.363 mL, 10 eq) in DMF (1 mL) was purged with nitrogen. The reaction vial was sealed and microwaved at 220° C. for 10 min. The mixture was purified by reverse-phase HPLC (80-100% solvent B gradient) to give Example 135 (14.6 mg, 49%). MS Found: (M+H)$^+$=411.

Example 136 rac-(1R,2S)-2-methyl-6-(1-methyl-1H-pyrazol-4-yl)-1-phenyl-N-1,3-thiazol-2-yl-2,3-dihydro-1H-indene-2-carboxamide

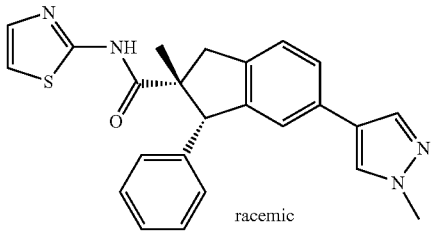
racemic

A solution of Example 73 (19 mg, 0.046 mmol), 1-methyl-4-(4,4,5,5-tetramethyl-1,3,2-dioxaborolan-2-yl)-1H-pyrazole (62 mg, 6.5 eq), Pd(OAc)$_2$ (9.8 mg, 1 eq), tri-tert-butylphosphine (46 µL, 4.5 eq) and 2 M aqueous K$_3$PO$_4$ (0.23 mL, 10 eq) in DMF (0.5 mL) was purged with argon for 10 min. The reaction vial was sealed and microwaved at 220° C. for 10 min. The crude mixture was purified by reverse-phase HPLC (75-100% solvent B gradient) followed by preparative TLC (80% EtOAc-Hexanes) to give Example 136 (8.8 mg, 46%). MS Found: (M+H)$^+$=415.

Example 137 rac-(1R,2S)-2-methyl-1-phenyl-6-(4-pyridinyl)-N-1,3-thiazol-2-yl-2,3-dihydro-1H-indene-2-carboxamide

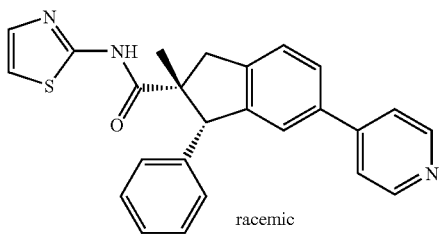

Following a procedure similar to Example 136, Example 73 (15 mg, 0.036 mmol) was reacted with pyridine-4-boronic acid (28.6 mg, 6.4 eq) to give Example 137 (8 mg, 42%). MS Found: (M+H)$^+$=412.

Example 138 rac-(1R,2S)-6-ethenyl-2-methyl-1-phenyl-N-1,3-thiazol-2-yl-2,3-dihydro-1H-indene-2-carboxamide

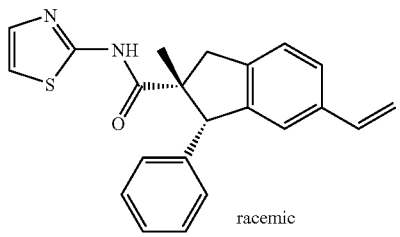

Following a procedure similar to Example 133, Example 73 (24 mg, 0.059 mmol) was reacted with 2,4,6-trivinylcyclotriboroxane pyridine complex (101.8 mg, 7.2 eq) to give Example 138 (5 mg, 24%). MS Found: (M+H)$^+$=361.

Example 139 rac-(1R,2S)-6-ethyl-2-methyl-1-phenyl-N-1,3-thiazol-2-yl-2,3-dihydro-1H-indene-2-carboxamide

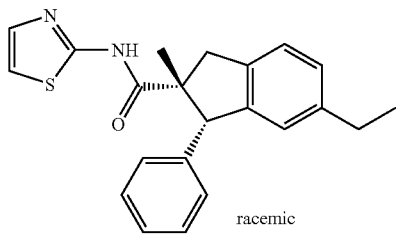

(139a) A solution of the bromoindane ester from 73e (88.5 mg, 0.256 mmol), 2,4,6-trivinylcyclotriboroxane pyridine complex (61.7 mg, 1 eq), K$_2$CO$_3$ (40 mg, 1.1 eq) and Pd(PPh$_3$)$_4$ (27.9 mg, 0.094 eq) in 1,2-dimethoxyethane (6 mL) and water (2 mL) was degassed with nitrogen. The mixture was heated at 90° C. for 3 h and concentrated. The aqueous residue was extracted with ether. The ether phase was dried (MgSO$_4$), concentrated and purified by silica gel chromatography (0-10% EtOAc-Hexanes gradient) to give the desired vinylindane ester (53 mg, 71%). MS Found: (M+Na)$^+$=315.

(139b) A MeOH (6 mL) solution of the vinylindane ester from 139a (53 mg, 0.18 mmol) was hydrogenated under 25 psi H$_2$ for 1 h to give the ethylindane ester (50 mg, 94%). MS Found: (M+Na)=317.

(139c) Following a procedure similar to reaction 20e, the ethylindane ester from reaction 139b (50 mg, 0.17 mmol) was hydrolyzed to the corresponding acid. MS Found: (M−H)$^-$=279.

(139d) Following a procedure similar to Example 2, the acid from reaction 139c (12.8 mg, 0.046 mmol) was reacted with 2-aminothiazole to give Example 139 (12.3 mg, 75%). MS Found: (M+H)$^+$=363.

Example 140 rac-(1R,2S)-6-ethenyl-2-methyl-1-phenyl-N-1,3,4-thiadiazol-2-yl-2,3-dihydro-1H-indene-2-carboxamide

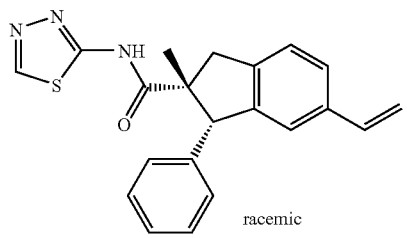

(140a) Following a procedure similar to reaction 20e, the vinylindane ester from reaction 139a (656.5 mg, 2.25 mmol) was hydrolyzed to the corresponding acid.

(140b) Following a procedure similar to Example 2, the acid from reaction 140a (9 mg, 0.032 mmol) was reacted with 2-amino-1,3,4-thiadiazole to give Example 140 (1.3 mg, 11%). MS Found: (M+H)$^+$=362.

Example 141 rac-(1R,2S)-6-ethyl-2-methyl-1-phenyl-N-1,3,4-thiadiazol-2-yl-2,3-dihydro-1H-indene-2-carboxamide

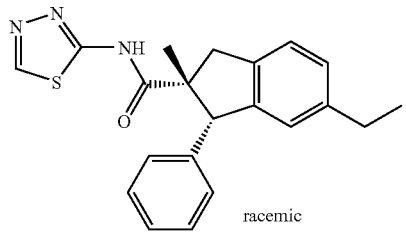

Following a procedure similar to Example 2, the acid from reaction 139c (17.5 mg, 0.062 mmol) was reacted with 2-amino-1,3,4-thiadiazole to give Example 141 (2.3 mg, 10%). MS Found: (M+H)$^+$=364.

Example 142 rac-(1R,2S)-6-cyclopropyl-2-methyl-1-phenyl-N-1,3-thiazol-2-yl-2,3-dihydro-1H-indene-2-carboxamide

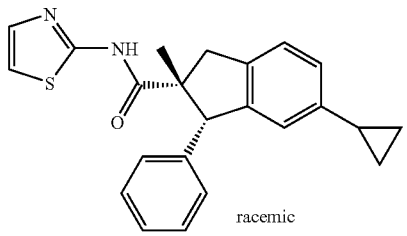

racemic (142a) A 15 wt % toluene solution of diethylzinc (1.83 mL, 2 eq) was added to 2,4,6-trichlorophenol (398 mg, 2 eq) in CH$_2$Cl$_2$ (20 mL) at −40° C. The resulting white cloudy solution was stirred at −40° C. for 15 min. Diiodomethane (162 µL, 2 eq) was added and the mixture was stirred at −40° C. for 15 min. The vinylindane ester from reaction 139a (294 mg, 1 mmol) in CH$_2$Cl$_2$ (5 mL) was added. The cold bath was allowed to slowly warm to room temperature overnight. The reaction mixture was quenched with 1 N HCl (4 mL) and extracted with EtOAc (100 mL). The organic phase was washed with saturated NaHCO$_3$ (10 mL), brine (5 mL), dried (MgSO$_4$) and concentrated. Silica gel chromatography (0-10% EtOAc-Hexanes gradient) followed by reverse-phase HPLC (90-100% solvent B gradient) gave the cyclopropyl-indane ester (61.9 mg, 20%). MS Found: (M+Na)$^+$=329.

(142b) Following a procedure similar to reaction 20e, the cyclopropyl-indane ester from reaction 142a (48.6 mg, 0.159 mmol) was hydrolyzed to the corresponding acid. MS Found: (M−CO$_2$H)$^+$=247.

(142c) Following a procedure similar to Example 2, the acid from reaction 142b (0.039 mmol) was reacted with 2-aminothiazole to give Example 142 (11.6 mg, 78%). MS Found: (M+H)$^+$=375.

Example 143 rac-(1R,2S)-6-cyclopropyl-2-methyl-1-phenyl-N-1,3,4-thiadiazol-2-yl-2,3-dihydro-1H-indene-2-carboxamide

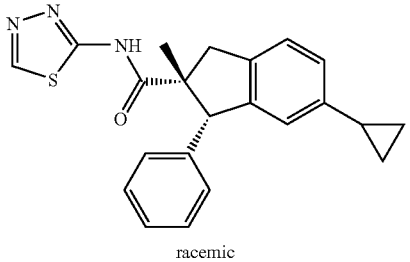

racemic

Following a procedure similar to Example 2, the acid from reaction 142b (0.018 mmol) was reacted with 2-amino-1,3,4-thiadiazole to give Example 143 (2.2 mg, 33%). MS Found: (M+H)$^+$=376.

Example 144 rac-(1R,2S)-2-methyl-1-phenyl-6-((1E)-1-propen-1-yl)-N-1,3-thiazol-2-yl-2,3-dihydro-1H-indene-2-carboxamide

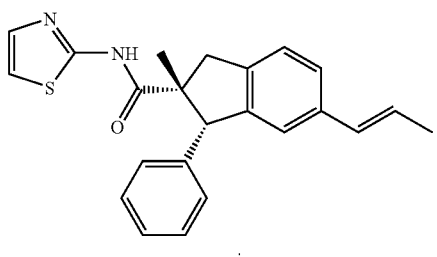

racemic (144a) Following a procedure similar to reaction 139a, the bromoindane ester from 73e (107 mg, 0.31 mmol) was coupled with trans-propenylboronic acid to give the trans-propenylindane ester (20.5 mg, 21%). MS Found: (M+Na)$^+$=329.

(144b) Following a procedure similar to reaction 20e, the trans-propenylindane ester from reaction 144a was hydrolyzed to the corresponding acid. MS Found: (M+Na)$^+$=315.

(144c) Following a procedure similar to Example 2, the acid from reaction 144b (7 mg, 0.024 mmol) was reacted with 2-aminothiazole to give Example 144 (2.2 mg, 24%). MS Found: (M+H)$^+$=375.

Example 145 rac-(1R,2S)-2-methyl-1-phenyl-6-propyl-N-1,3-thiazol-2-yl-2,3-dihydro-1H-indene-2-carboxamide

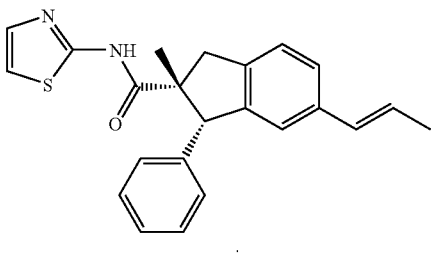

racemic (145a) A MeOH (6 mL) solution of the trans-propenylindane acid from 144b (11.8 mg, 0.18 mmol) was hydrogenated under 50 psi H$_2$ for 1 h to give propylindane acid. MS Found: (M+Na)=317.

(145b) Following a procedure similar to Example 2, the acid from reaction 145a (6 mg, 0.02 mmol) was reacted with 2-aminothiazole to give Example 145 (4.2 mg, 55%). MS Found: (M+H)$^+$=377.

Example 146 rac-(1R,2S)-2-methyl-1-phenyl-6-(2-propen-1-yl)-N-1,3-thiazol-2-yl-2,3-dihydro-1H-indene-2-carboxamide

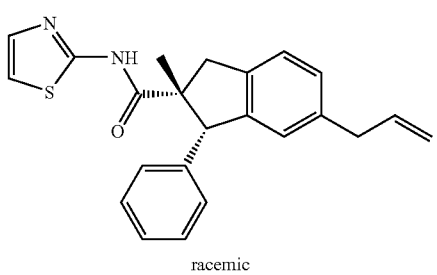

racemic (146a) Following a procedure similar to reaction 139a, the bromoindane ester from 73e (159 mg, 0.46 mmol) was coupled with allylboronic acid pinacol cyclic ester (85 mg, 1 eq) to give the allylindane ester.

(146b) Following a procedure similar to reaction 20e, the allylindane ester from reaction 146a was hydrolyzed to the corresponding acid (13.7 mg, 23% for 2 steps). MS Found: (M−H)+=291.

(146c) Following a procedure similar to Example 2, the acid from reaction 146b (6.9 mg, 0.024 mmol) was reacted with 2-amino-thiazole to give Example 146 (7 mg, 81%). MS Found: (M+H)+=375.

Example 147 rac-(1R,2S)-2-methyl-1-phenyl-6-((E)-2-phenylethenyl)-N-1,3-thiazol-2-yl-2,3-dihydro-1H-indene-2-carboxamide

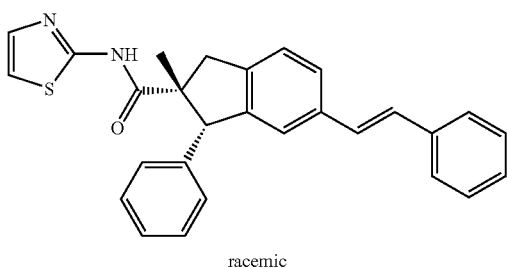

racemic (147a) Following a procedure similar to reaction 139a, the bromoindane ester from 73e (117 mg, 0.34 mmol) was coupled with trans-phenylvinylboronic acid (57 mg, 1 eq) to give the trans-phenylvinylindane ester (95.5 mg, 76%). MS Found: (M+Na)+=391.

(147b) Following a procedure similar to reaction 20e, the trans-phenylvinylindane ester from reaction 147a (95.5 mg, 0.26 mmol) was hydrolyzed to the corresponding acid (91.7 mg, 99%).

(147c) Following a procedure similar to Example 2, the acid from reaction 147b (10.9 mg, 0.031 mmol) was reacted with 2-amino-thiazole to give Example 147 (4.6 mg, 34%). MS Found: (M+H)+=437.

Example 148 rac-(1R,2S)-2-methyl-1-phenyl-6-(2-phenylethyl)-N-1,3-thiazol-2-yl-2,3-dihydro-1H-indene-2-carboxamide

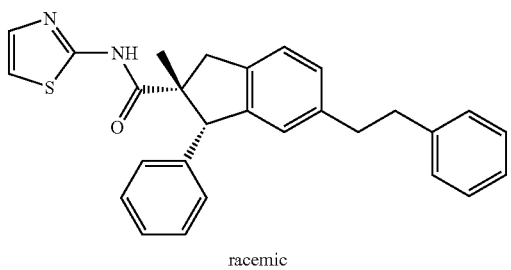

racemic (148a) Following a procedure similar to reaction 145a, the trans-phenylvinylindane acid from 147b (37 mg, 0.11 mmol) was hydrogenated to give the desired acid. MS Found: (M+Na)=379.

(148b) Following a procedure similar to Example 2, the acid from reaction 148a (7 mg, 0.02 mmol) was reacted with 2-aminothiazole to give Example 148 (2.6 mg, 29%). MS Found: (M+H)+=439.

Example 149 rac-(1R,2S)-2-methyl-1-phenyl-6-((E)-2-phenylethenyl)-N-1,3,4-thiadiazol-2-yl-2,3-dihydro-1H-indene-2-carboxamide

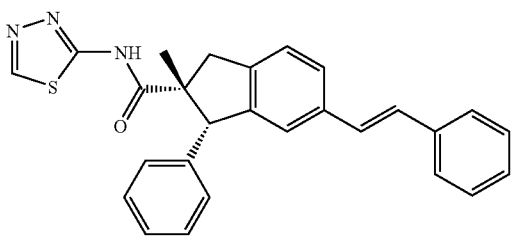

racemic

Following a procedure similar to Example 2, the acid from reaction 147b (10.8 mg, 0.03 mmol) was reacted with 2-amino-1,3,4-thiadiazole to give Example 149 (5.5 mg, 41%). MS Found: (M+H)+=438.

Example 150 rac-(1R,2S)-2-methyl-1-phenyl-N-1,3-thiazol-2-yl-6-((trimethylsilyl)ethynyl)-2,3-dihydro-1H-indene-2-carboxamide

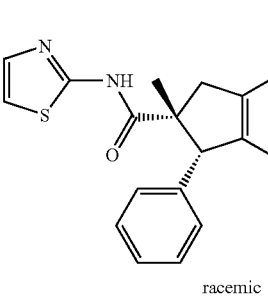

racemic

A toluene (1.5 mL) solution of the Example 73 (67 mg, 0.16 mmol), CuI (6.5 mg, 0.21 eq) and Pd(PPh$_3$)$_4$ (20.4 mg, 0.11 eq) was purged with nitrogen. Trimethylsilylacetylene (92 µL, 4 eq) and triethylamine (46 µL, 1.8 eq) were added. The sealed flask was heated at 80° C. for 21 h. Only 33% conversion was observed by HPLC. After cooling, the mixture was diluted with CH$_2$Cl$_2$ and filtered. The filtrate was concentrated and purified by reverse-phase HPLC (90-100% solvent B gradient) to give Example 150 (10.6 mg, 15%). MS Found: (M+H)$^+$=431.

Example 151 rac-(1R,2S)-6-ethynyl-2-methyl-1-phenyl-N-1,3-thiazol-2-yl-2,3-dihydro-1H-indene-2-carboxamide

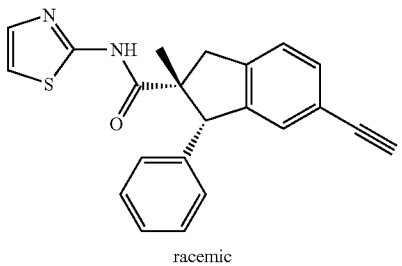

racemic

A 1 M THF solution of tetrabutylammonium fluoride (40 µL, 2 eq) was added to a solution of Example 150 (8.7 mg, 0.02 mmol) in CH$_2$Cl$_2$ (2 mL). The mixture was stirred at room temperature for 5 min, concentrated and purified by reverse-phase HPLC (85-100% solvent B gradient) to give Example 151 (6.5 mg, 90%). MS Found: (M+H)$^+$=359.

Example 152 rac-(1R,2S)-6-ethynyl-2-methyl-1-phenyl-N-1,3,4-thiadiazol-2-yl-2,3-dihydro-1H-indene-2-carboxamide

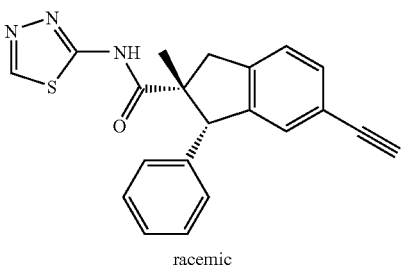

racemic (152a) Following a procedure similar to the preparation of Example 150, Example 74 (128 mg, 0.31 mmol) was coupled with trimethylsilylacetylene to give the coupled product (15 mg, 11%). MS Found: (M+Na)=432.

(152b) Following a procedure similar to the preparation of Example 151, the coupled product from reaction 152a (15 mg, 0.035 mmol) was desilylated to give Example 152 (5.4 mg, 43%). MS Found: (M+H)$^+$=360.

Example 153 rac-(1R,2S)-2-methyl-1-phenyl-6-(1-propyn-1-yl)-N-1,3-thiazol-2-yl-2,3-dihydro-1H-indene-2-carboxamide

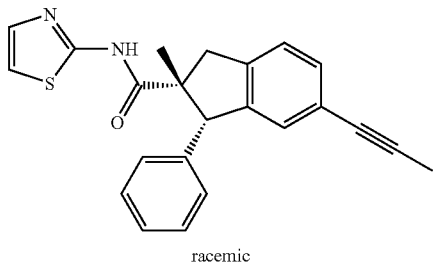

racemic

A solution of the Example 73 (43.7 mg, 0.106 mmol), tributyl-(1-propynyl)tin (104 µL, 3 eq) and Pd(PPh$_3$)$_4$ (18.5 mg, 0.15 eq) in DMF (0.5 mL) was purged with argon for 10 min. The mixture was microwaved at 120° C. for 10 min and purified by reverse-phase HPLC (90-100% solvent B gradient) followed by preparative TLC (40% EtOAc-Hexanes) to give Example 153 (6 mg, 15%). MS Found: (M+H)$^+$=373.

Example 154 rac-(1R,2S)-2-methyl-1-phenyl-6-(phenylethynyl)-N-1,3-thiazol-2-yl-2,3-dihydro-1H-indene-2-carboxamide

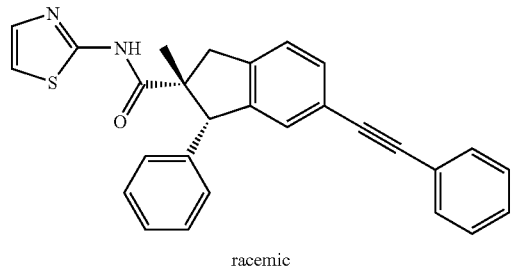

racemic (154a) A solution of the bromoindane ester from reaction 73e (114 mg, 0.33 mmol), CuI (17.8 mg, 0.28 eq) and PdCl$_2$(PPh$_3$)$_2$ (18.6 mg, 0.08 eq) in DMF (2 mL) was purged with nitrogen. Phenylacetylene (150 µL, 4 eq) and triethylamine (100 µL, 2.2 eq) were added. The sealed flask was heated at 90° C. for 21 h. Only 55% conversion was observed by HPLC. After cooling, the mixture was poured into a mixture of saturated NH$_4$Cl (20 mL), aqueous ammonia (2 mL) and EtOAc (40 mL). The EtOAc phase was separated and washed with saturated NH$_4$Cl (20 mL), brine (20 mL), dried (MgSO$_4$) and concentrated. Reverse-phase HPLC (95-100% solvent B gradient) gave the coupled product (50.5 mg, 42%). MS Found: (M+Na)$^+$=389.

(154b) Following a procedure similar to reaction 20e, the coupled product from reaction 154a (24.4 mg, 0.067 mmol) was hydrolyzed to the corresponding acid (20.4 mg). MS Found: (M+Na)$^+$=375.

(154c) Following a procedure similar to the preparation of Example 2, the acid from reaction 154b (5.9 mg, 0.017 mmol) was reacted with 2-aminothiazole to give Example 154 (1.9 mg, 26%). MS Found: (M+H)$^+$=435.

Example 155 rac-(1R,2S)-2-methyl-1-phenyl-5-(phenyloxy)-N-1,3-thiazol-2-yl-2,3-dihydro-1H-indene-2-carboxamide

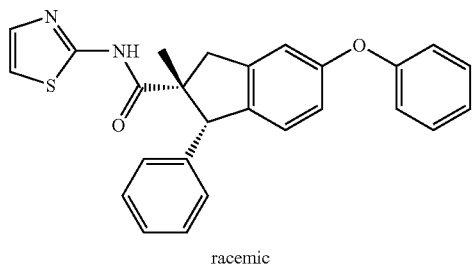

racemic

A mixture of Example 36 (11.3 mg, 0.032 mmol), Cu(OAc)$_2$ (8.9 mg, 1.5 eq), phenylboronic acid (11.3 mg, 2.9 mmol), triethylamine (22.6 µL, 5 eq) and powdered 4 Å molecular sieve (33.7 mg) in CH$_2$Cl$_2$ (2.5 mL) was stirred at room temperature for 16 h while open to the atmosphere. After filtration to remove the molecular sieve, the filtrate was concentrated and purified by reverse-phase HPLC (80-100% solvent B gradient) to give Example 155. (4.9 mg, 36%). MS Found: (M+H)$^+$=427.

Example 156 rac-(1R,2S)-2-methyl-1-phenyl-6-(phenyloxy)-N-1,3-thiazol-2-yl-2,3-dihydro-1H-indene-2-carboxamide

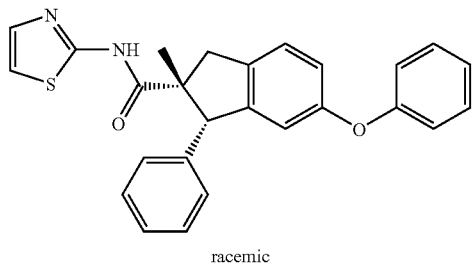

racemic

Following a procedure similar to the preparation of Example 155, Example 41 (38.5 mg, 0.11 mmol) was converted to Example 156 (11.1 mg, 24%). MS Found: (M+H)$^+$=427.

Example 157 rac-(1R,2S)-6-chloro-2-methyl-1-phenyl-N-1,3-thiazol-2-yl-2,3-dihydro-1H-indene-2-carboxamide

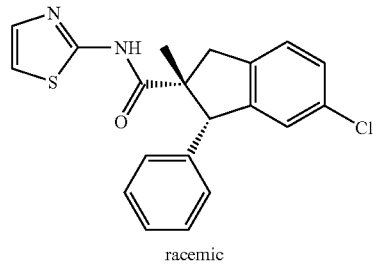

racemic

A solution of Example 73 (15.4 mg, 0.037 mmol) and CuCl (40.6 mg, 11 eq) in DMF (0.8 mL) was purged with nitrogen and microwaved at 220° C. for 1 h. The crude mixture was poured into a solution of saturated NH$_4$Cl (9 mL), aqueous ammonia (1 mL) and EtOAc (20 mL) and stirred at room temperature with air bubbling for 1 h. The EtOAc phase was separated, washed with saturated NH$_4$Cl (5 mL) and brine (5 mL), dried (MgSO$_4$), and concentrated. Reverse-phase HPLC (80-100% solvent B gradient) gave Example 157 (10.4 mg, 76%). MS Found: (M+H)$^+$=369.

Example 158 rac-(1R,2S)-6-chloro-2-methyl-1-phenyl-N-1,3,4-thiadiazol-2-yl-2,3-dihydro-1H-indene-2-carboxamide

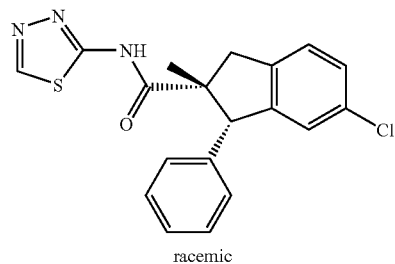

racemic (158a) Following a procedure similar to the preparation of Example 157, the bromo acid from reaction 73f (20 mg, 0.06 mmol) was converted to the chloro acid (7 mg, 41%). MS Found: (M–H)$^-$=285.

(158b) Following a procedure similar to the preparation of Example 2, the acid from reaction 158a (7 mg, 0.024 mmol) was reacted with 2-amino-1,3,4-thiadiazole to give Example 158 (5.6 mg, 62%). MS Found: (M+H)$^+$=370.

Example 159

(1S,2R)-6-chloro-2-methyl-1-phenyl-N-1,3,4-thiadiazol-2-yl-2,3-dihydro-1H-indene-2-carboxamide

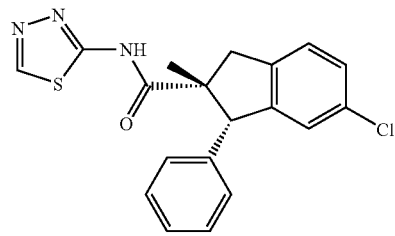

(159a) Following a procedure similar to the preparation of Example 157, the slow eluting enantiomer of the bromo acid from reaction 90a (64 mg, 0.19 mmol) was converted to the chloro acid (37 mg, 67%). MS Found: (M-CO$_2$H)$^+$=241.

(159b) Following a procedure similar to the preparation of Example 2, the acid from reaction 159a (37 mg, 0.13 mmol) was reacted with 2-amino-1,3,4-thiadiazole to give Example 159 (34 mg, 71%). MS Found: (M+H)$^+$=370.

Example 160

(1R,2S)-6-chloro-2-methyl-1-phenyl-N-1,3,4-thia-diazol-2-yl-2,3-dihydro-1H-indene-2-carboxamide

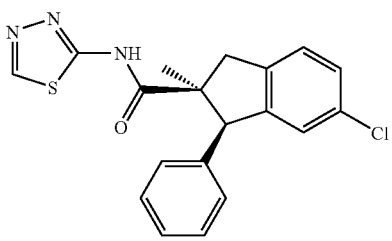

(160a) Following a procedure similar to the preparation of Example 157, the fast eluting enantiomer of the bromo acid from reaction 90a (88 mg, 0.27 mmol) was converted to the chloro acid (63 mg, 83%). MS Found: (M-CO$_2$H)$^+$=241.

(160b) Following a procedure similar to the preparation of Example 2, the acid from reaction 160a (22 mg, 0.08 mmol) was reacted with 2-amino-1,3,4-thiadiazole to give Example 159 (20 mg, 70%). MS Found: (M+H)$^+$=370.

Example 161

(1S,2R)-6-bromo-2-methyl-1-phenyl-N-1,3,4-thia-diazol-2-yl-2,3-dihydro-1H-indene-2-carboxamide

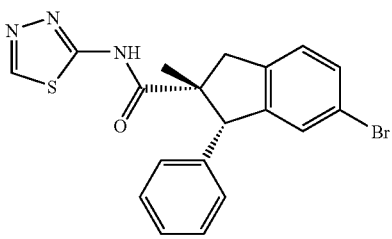

Following a procedure similar to the preparation of Example 2, the slow eluting enantiomer of the bromo acid from reaction 90a (31 mg, 0.09 mmol) was reacted with 2-amino-1,3,4-thiadiazole to give Example 161 (14 mg, 36%). MS Found: (M+H)$^+$=414, 416.

Example 162

(1R,2S)-6-bromo-2-methyl-1-phenyl-N-1,3,4-thia-diazol-2-yl-2,3-dihydro-1H-indene-2-carboxamide

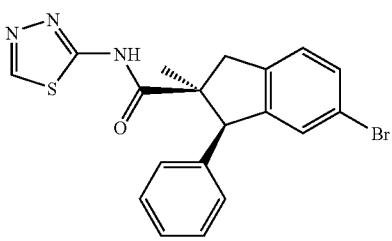

Following a procedure similar to the preparation of Example 2, the fast eluting enantiomer of the bromo acid from reaction 90a (47 mg, 0.14 mmol) was reacted with 2-amino-1,3,4-thiadiazole to give Example 162 (38 mg, 65%). MS Found: (M+H)$^+$=414, 416.

Example 163 rac-(1R,2S)-6-(1H-imidazol-1-yl)-2-methyl-1-phenyl-N-1,3-thiazol-2-yl-2,3-dihydro-1H-indene-2-carboxamide

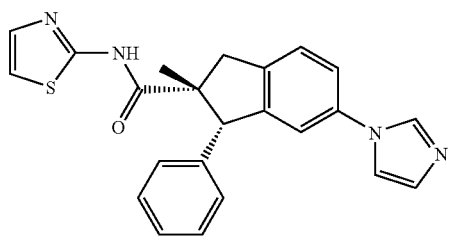

racemic

A DMF (1 mL) solution of Example 73 (13 mg, 0.032 mmol), imidazole (25.8 mg, 119 mmol), Cs$_2$CO$_3$ (15 mg, 1.5 eq) and CuI (7.6 mg, 1.2 eq) was purged with argon and microwaved at 220° C. for 20 min. The crude mixture was purified by reverse-phase HPLC (60-90% solvent B gradient) to give Example 163 (2 mg, 17%). MS Found: (M+H)$^+$=401.

Example 164 rac-(1R,2S)-2-methyl-6-(4-morpholinyl)-1-phenyl-N-1,3-thiazol-2-yl-2,3-dihydro-1H-indene-2-carboxamide

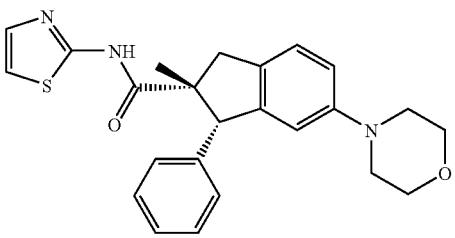

racemic

A toluene (1 mL) solution of Example 73 (23 mg, 0.057 mmol), KO$^t$Bu (19 mg, 3 eq), Pd(OAc)$_2$ (2.2 mg, 0.17 eq), tri-tert-butylphosphine (45 µL, 3 eq) and morpholine (10 µL, 1.9 eq) was purged with argon and heated in a sealed tube at 100° C. for 16 h and at 150° C. for 1.5 h. The crude mixture was concentrated and purified by reverse-phase HPLC (60-90% solvent B gradient) followed by preparative TLC (75% EtOAc-Hexanes) to give Example 164 (1.5 mg, 6%). MS Found: (M+H)$^+$=420.

Example 165 rac-(1R,2S)-2-methyl-1-phenyl-6-(1-piperidinyl)-N-1,3-thiazol-2-yl-2,3-dihydro-1H-indene-2-carboxamide

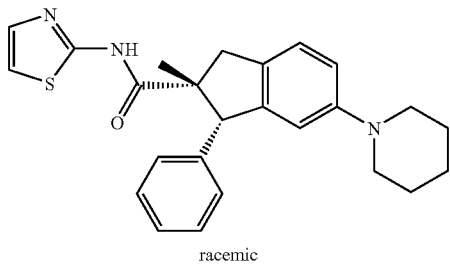

racemic

A toluene (0.5 mL) solution of Example 73 (27 mg, 0.065 mmol), KO$^t$Bu (26 mg, 3.5 eq), Pd(OAc)$_2$ (9.2 mg, 0.63 eq), tri-tert-butylphosphine (50 µL, 3 eq) and piperidine (100 µL, 16 eq) was microwaved at 120° C. for 45 min. The mixture was concentrated and purified by reverse-phase HPLC (50-80% solvent B gradient) followed by preparative TLC (75% EtOAc-Hexanes) to give Example 165 (1.5 mg, 6%). MS Found: (M+H)$^+$=418.

Example 166 rac-(1R,2S)-6-(dimethylamino)-2-methyl-1-phenyl-N-1,3-thiazol-2-yl-2,3-dihydro-1H-indene-2-carboxamide

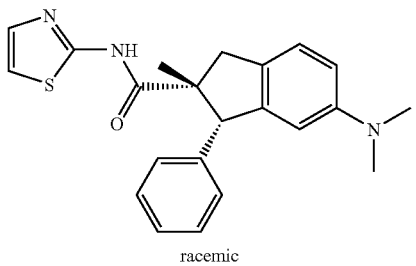

racemic

A toluene (1 mL) solution of Example 73 (27 mg, 0.065 mmol), dichlorobis(tri-o-tolylphosphine)palladium (II) (11.6 mg, 0.23 eq) and dimethylaminotri-n-butyltin (300 µL, 14 eq) was purged with argon and heated in a sealed tube at 100° C. for 18 h. The mixture was concentrated and purified by reverse-phase HPLC (50-80% solvent B gradient) to give Example 166 (2.6 mg, 11%). MS Found: (M+H)$^+$=378.

Example 167 rac-(1R,2S)-6-formyl-2-methyl-1-phenyl-N-1,3-thiazol-2-yl-2,3-dihydro-1H-indene-2-carboxamide

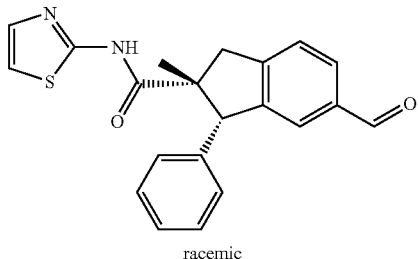

racemic (167a) To a CH$_2$Cl$_2$ (20 mL) solution of the vinylindane acid from reaction 140a (maximum 2 mmol) was bubbled in O3 at −78° C. until the solution color stayed blue. This blue solution was stirred at −78° C. for 30 min then purged with N$_2$ until the blue color disappeared. Polystyrene-linked triphenylphosphine (1.4-2.0 mmol/g loading, 3.42 g) was added. The mixture was allowed to slowly warm to room temperature overnight, filtered and concentrated to give the formylindane acid (0.37 g, 67%). MS Found: (M+H)$^+$=281.

(167b) Following a procedure similar to the preparation of Example 2, the acid from reaction 167a (140 mg, 0.5 mmol) was reacted with 2-aminothiazole to give Example 167 (73 mg, 40%). MS Found: (M+H)$^+$=363.

Example 168 rac-(1R,2S)-6-(hydroxymethyl)-2-methyl-1-phenyl-N-1,3-thiazol-2-yl-2,3-dihydro-1H-indene-2-carboxamide

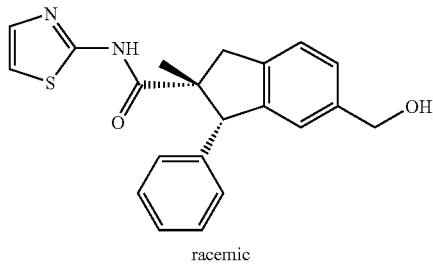

racemic

A 1,2-dichloroethane (1 mL) solution of Example 167 (7 mg, 0.02 mmol), sodium triacetoxyborohydride (63 mg, 16 eq) and acetic acid (10 drops) was stirred at room temperature for 19 h. The mixture was concentrated and purified by reverse-phase HPLC (60-75% solvent B gradient) to give Example 168 (5.4 mg, 77%). MS Found: (M+H)$^+$=365.

Example 169 rac-(1R,2S)-6-((dimethylamino)methyl)-2-methyl-1-phenyl-N-1,3-thiazol-2-yl-2,3-dihydro-1H-indene-2-carboxamide

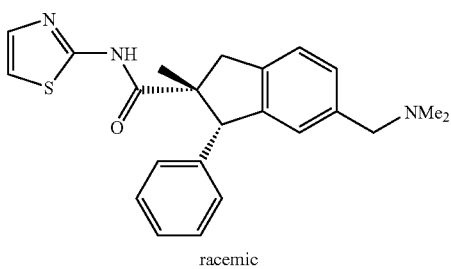

racemic

A 1,2-dichloroethane (1 mL) solution of Example 167 (7.8 mg, 0.022 mmol), sodium triacetoxyborohydride (18 mg, 3.9 eq) and a 2 M THF solution of dimethylamine (40 µL, 3.6 eq) was stirred at room temperature for 4 h. The mixture was concentrated and purified by reverse-phase HPLC (50-80% solvent B gradient) to give Example 169 (9.6 mg, 88%). MS Found: (M+H)$^+$=392.

Example 170

N-(3-methyl-N-(4-((4-(4-pyridinyl)phenyl)methyl)-1,3-thiazol-2-yl)-1H-indene-2-carboxamide

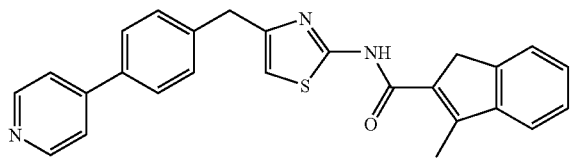

Using a procedure similar to the synthesis of Example 2, 3-methyl-1H-indene-2-carboxylic acid was reacted with 2-amino-4-(4-(pyridin-4-yl)benzyl)thiazole to give Example 170. MS Found: $(M+H)^+=424$.

Example 171 rac-(1R,2S)-2-methyl-6-(4-morpholinylmethyl)-1-phenyl-N-1,3-thiazol-2-yl-2,3-dihydro-1H-indene-2-carboxamide

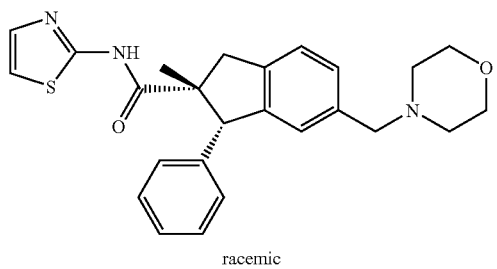

racemic

Following a procedure similar to the preparation of Example 169, Example 167 (7.6 mg, 0.021 mmol) was reacted with morpholine to give Example 171 (9 mg, 79%). MS Found: $(M+H)^+=434$.

Example 172 rac-(1R,2S)-2-methyl-6-((((4-(methyloxy)phenyl)methyl)amino)methyl)-1-phenyl-N-1,3-thiazol-2-yl-2,3-dihydro-1H-indene-2-carboxamide

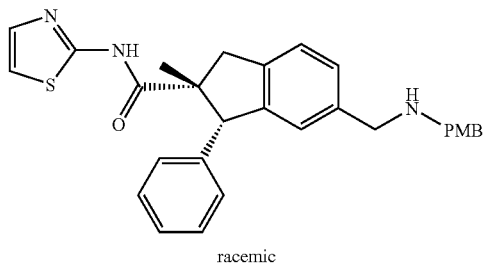

racemic

Following a procedure similar to the preparation of Example 169, Example 167 (10 mg, 0.028 mmol) was reacted with 4-methoxybenzylamine to give Example 172 (13 mg, 80%). MS Found: $(M+H)^+=484$.

Example 173 rac-(1R,2S)-6-formyl-2-methyl-1-phenyl-N-1,3,4-thiadiazol-2-yl-2,3-dihydro-1H-indene-2-carboxamide

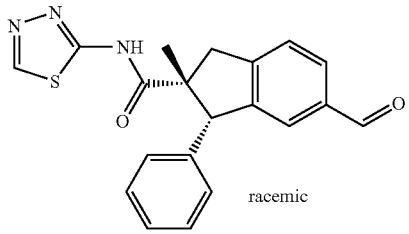

racemic

Following a procedure similar to the preparation of Example 2, the acid from reaction 167a (122 mg, 0.44 mmol) was reacted with 2-amino-1,3,4-thiadiazole to give Example 173 (83 mg, 53%). MS Found: $(M+H)^+=364$.

Example 174 rac-(1R,2S)-6-(hydroxymethyl)-2-methyl-1-phenyl-N-1,3,4-thiadiazol-2-yl-2,3-dihydro-1H-indene-2-carboxamide

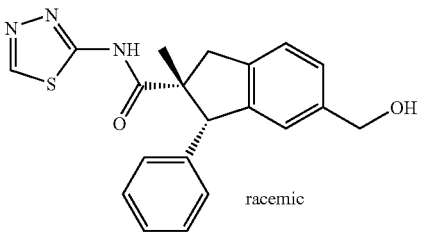

racemic

Following a procedure similar to the preparation of Example 168, Example 173 (10 mg, 0.028 mmol) was reduced to give Example 174 (4.3 mg, 43%). MS Found: $(M+H)^+=366$.

Example 175 rac-(1R,2S)-6-((1R,S)-1-hydroxyethyl)-2-methyl-1-phenyl-N-1,3,4-thiadiazol-2-yl-2,3-dihydro-1H-indene-2-carboxamide

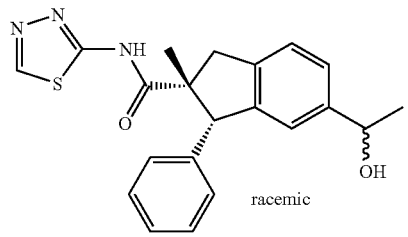

racemic

A 3 M ether solution of methylmagnesium bromide (50 μL, 5.5 eq) was added to Example 173 (10 mg, 0.028 mmol) in THF (1 mL) at room temperature. After stirring for 2 h, the mixture was quenched with saturated $NH_4Cl$ (1 mL), concentrated and purified by reverse-phase HPLC (50-70% solvent B gradient) to give Example 175 (6.7 mg, 64%). MS Found: $(M+H)^+=380$.

Example 176 rac-(1R,2S)-6-((R,S)-hydroxy(phenyl)methyl)-2-methyl-1-phenyl-N-1,3,4-thiadiazol-2-yl-2,3-dihydro-1H-indene-2-carboxamide

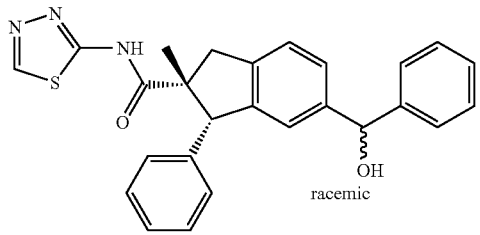
racemic

Following a procedure similar to the preparation of Example 175, Example 173 (11 mg, 0.03 mmol) was reacted with phenylmagnesium bromide to give Example 176 (7 mg, 54%). MS Found: (M+Na)$^+$=464.

Example 177 rac-(1R,2S)-6-cyano-2-ethyl-1-phenyl-N-1,3-thiazol-2-yl-2,3-dihydro-1H-indene-2-carboxamide

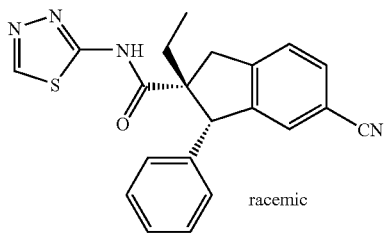
racemic (177a) Following a procedure similar to reaction 73d, the indanone from reaction 73c (443 mg, 1.28 mmol) was reacted with iodoethane to give the desired indanone (318 mg, 66%). MS Found: (M+H)$^+$=373, 375.

(177b) Following a procedure similar to reaction 73e, the indanone from reaction 177a (318 mg, 0.85 mmol) was reduced to the indane (195 mg, 64%). MS Found: (M+Na)=381, 383.

(177c) Following a procedure similar to reaction 20e, the indane from reaction 177b (195 mg, 0.54 mmol) was hydrolyzed to give the acid (161 mg, 86%). MS Found: (M+Na)$^+$=367, 369.

(177d) Following a procedure similar to the preparation of Example 85, the bromo acid from reaction 177c (86 mg, 0.25 mmol) was converted to the cyano acid (34 mg, 47%). MS Found: (M+H)$^+$=292.

(177e) Following a procedure similar to the preparation of Example 2, the acid from reaction 177d (8 mg, 0.027 mmol) was reacted with 2-aminothiazole to give Example 177 (4.6 mg, 45%). MS Found: (M+H)$^+$=374.

Example 178 rac-(1R,2S)-6-cyano-2-ethyl-1-phenyl-N-1,3,4-thiadiazol-2-yl-2,3-dihydro-1H-indene-2-carboxamide

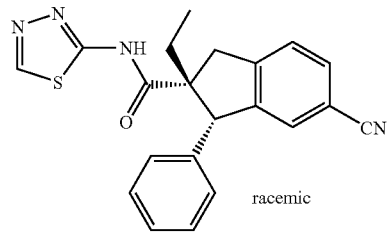
racemic

Following a procedure similar to the preparation of Example 2, the acid from reaction 177d (8.6 mg, 0.03 mmol) was reacted with 2-amino-1,3,4-thiadiazole to give Example 178 (3.6 mg, 32%). MS Found: (M+H)$^+$=375.

Examples 179 and 180 rac-(1R,2S)-2-methyl-6-(methyloxy)-1-propyl-N-1,3-thiazol-2-yl-2,3-dihydro-1H-indene-2-carboxamide; and rac-(1R,2R)-2-methyl-6-(methyloxy)-1-propyl-N-1,3-thiazol-2-yl-2,3-dihydro-1H-indene-2-carboxamide

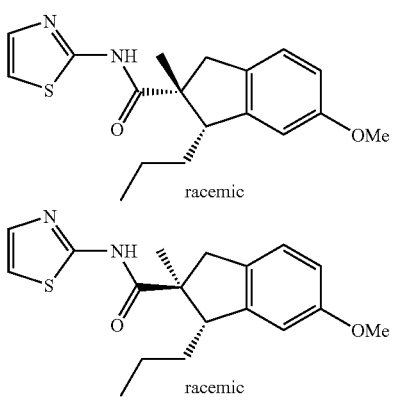

(179a) A solution of 6-methoxy-1-indanone (10.0 g, 61.7 mmol) in benzene (100 mL) was added over 1 h to a mixture of sodium hydride (60%, 7.40 g, 3 eq) and dimethyl carbonate (33.35 g, 6 eq) in benzene (200 mL) at 60° C. After 1 h at 60° C. and 2 h at 90° C., no reaction took place. After cooling to room temperature, DMF (20 mL) was added. The mixture was stirred at ambient temperature for 10 min and at 90° C. for 40 min, cooled to room temperature and quenched with 1 N HCl (300 mL). The two layers were separated. The aqueous phase was extracted with EtOAc-hexane (1:4, 2×100 mL). The combined organic phase was washed with water (25 mL), brine (25 mL), dried (MgSO$_4$) and concentrated. The residue was filtered through a silica gel pad and the pad rinsed with EtOAc-hexane (3:7). The filtrate was concentrated and triturated with hexane (100 mL) to give a brown solid. Filtration and washing with hexane (2×50 mL) gave the desired keto ester (11.21 g, 83%). MS Found: (M+H)$^+$=221.

(179b) K$_2$CO$_3$ (13.82 g, 2 eq) and iodomethane (6.24 mL, 2 eq) were added to the keto ester from reaction 179a (11.00 g, 50 mmol) in DMSO (50 mL). After 2 h at room temperature, 1 N HCl (200 mL) was added. The mixture was extracted with EtOAc-hexane (1:1, 3×100 mL). The combined extracts were washed with water (20 mL), brine (20 mL) and dried (MgSO$_4$). The mixture was filtered through a silica gel pad and the pad rinsed with EtOAc-hexane (1:1). The filtrate was concentrated to give the desired product as a brown solid (11.42 g, 98%). MS Found: (M+H)$^+$=235.

(179c) A 1 M ether solution of allylmagnesium bromide (6.41 mL, 1.5 eq) was added to the keto ester from reaction 179b (1.00 g, 4.27 mmol) in THF (50 mL). After 1 h at room temperature, additional allylmagnesium bromide (0.5 eq) was added. After 15 min, the mixture was quenched with saturated NH$_4$Cl (100 mL). The THF solvent was evaporated in vacuo. The aqueous residue was extracted with EtOAc (3×50 mL). The combined extracts were washed with brine (10 mL), dried (MgSO$_4$) and concentrated. Silica gel chromatography (10-25% EtOAc-hexane gradient) provided the desired alcohol as a slightly yellow oil (523 mg, 44%). MS Found: (M+Na)$^+$=299.

(179d) Triethylsilane (2 mL) and trifluoroacetic acid (2 mL) were added to the alcohol from reaction 179c (461.2 mg, 1.67 mmol) in CH$_2$Cl$_2$ (20 mL). After 30 min at room temperature, the mixture was concentrated. Silica gel chromatography (2-6% EtOAc-hexane gradient) provided a mixture of olefin product (303 mg).

(179e) The crude product from reaction 179d, palladium on carbon (10%, 500 mg) and methanol were hydrogenated under 50 psi for 16 h. After removal of catalyst by filtration, the filtrate was concentrated to give the 1-propylindane product as a 1:1 mixture of cis and trans isomers (288 mg, 66% for 2 steps). MS Found: (M+Na)$^+$=285.

(179f) A mixture of the 1-propylindane from reaction 179e (287.6 mg, 1.10 mmol), 1 N NaOH (8 mL), DMSO (8 mL) and methanol (8 mL) was heated at reflux for 3 h then cooled to room temperature. After evaporation of methanol in vacuo, the residue was acidified with 1 N HCl (10 mL), diluted with water (10 mL) and extracted with EtOAc (3×25 mL). The combined extracts were washed with brine (5 mL), dried (MgSO$_4$) and filtered through a silica gel pad. The pad was rinsed with EtOAc. The filtrate was concentrated to give the desired acid as a colorless oil (273 mg, 100%). MS Found: (M+Na)$^+$=271.

(179g) HOBt monohydrate (101 mg, 1.5 eq), EDC hydrochloride (173 mg, 1.8 eq), Hunig base (0.521 mL, 6 eq) and 2-aminothiazole (100 mg, 2 eq) were added to the acid from reaction 179f (124 mg, 0.500 mmol) in CH$_3$CN (2 mL). The mixture was stirred at 60° C. overnight, diluted with EtOAc (60 mL), washed with saturated NH$_4$Cl (3×5 mL), brine (5 mL), dried (MgSO$_4$) and concentrated. Reverse phase HPLC (60-85% solvent B gradient) gave fast eluting isomer Example 179 (64.1 mg, 39%) and slow eluting isomer Example 180 (60.5 mg, 37%). MS Found for both isomers: (M+H)$^+$=331.

Examples 181 and 182 rac-(1R,2S)-6-hydroxy-2-methyl-1-propyl-N-1,3-thiazol-2-yl-2,3-dihydro-1H-indene-2-carboxamide; and rac-(1R,2R)-6-hydroxy-2-methyl-1-propyl-N-1,3-thiazol-2-yl-2,3-dihydro-1H-indene-2-carboxamide

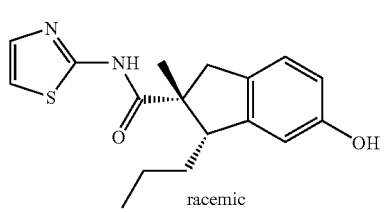

racemic

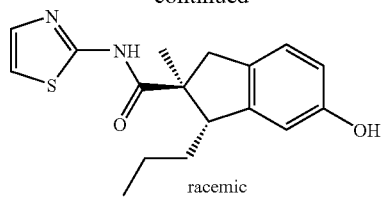

racemic

Using a procedure similar to the synthesis of Example 5, Examples 179 and 180 were converted to Examples 181 and 182 respectively. MS Found for both: (M+H)$^+$=317.

Examples 183 and 184 rac-(1R,2S)-2-methyl-6-(methyloxy)-1-(2-methylpropyl)-N-1,3-thiazol-2-yl-2,3-dihydro-1H-indene-2-carboxamide; and rac-(1R,2R)-2-methyl-6-(methyloxy)-1-(2-methylpropyl)-N-1,3-thiazol-2-yl-2,3-dihydro-1H-indene-2-carboxamide

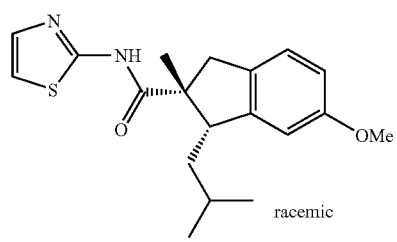

racemic

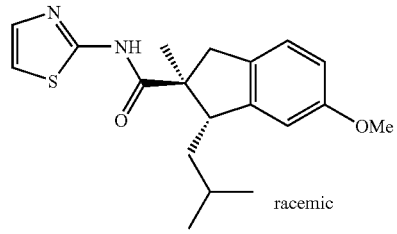

racemic

Using conditions similar to reactions 179c-g, the keto ester from reaction 179b was reacted with 2-methyl-1-propenylmagnesium bromide and converted to Examples 183 (fast eluting isomer) and 184 (slow eluting isomer). MS Found for both: (M+H)$^+$=345.

Examples 185 and 186 rac-(1R,2S)-6-hydroxy-2-methyl-1-(2-methylpropyl)-N-1,3-thiazol-2-yl-2,3-dihydro-1H-indene-2-carboxamide; and rac-(1R,2R)-6-hydroxy-2-methyl-1-(2-methylpropyl)-N-1,3-thiazol-2-yl-2,3-dihydro-1H-indene-2-carboxamide

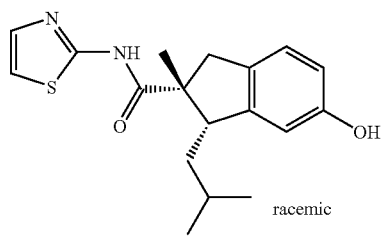

racemic

-continued

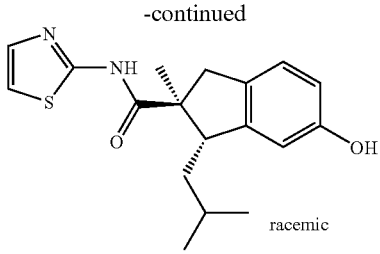

Using a procedure similar to the synthesis of Example 5, Examples 183 and 184 were converted to Examples 185 and 186 respectively. MS Found for both: (M+H)⁺=331.

Example 187 rac-(1R,2R)-2-methyl-6-(methyloxy)-1-(phenylmethyl)-N-1,3-thiazol-2-yl-2,3-dihydro-1H-indene-2-carboxamide

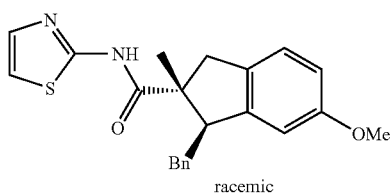

Using conditions similar reactions 179c-d and 17f-g, the keto ester from reaction 179b was reacted with benzylmagnesium bromide and converted to Examples 187 (slow eluting isomer) and a mixture of fast and slow eluting isomers. MS Found: (M+H)⁺=379.

Examples 188 and 189 rac-(1R,2R)-6-hydroxy-2-methyl-1-(phenylmethyl)-N-1,3-thiazol-2-yl-2,3-dihydro-1H-indene-2-carboxamide, and rac-(1R,2S)-6-hydroxy-2-methyl-1-(phenylmethyl)-N-1,3-thiazol-2-yl-2,3-dihydro-1H-indene-2-carboxamide, respectively

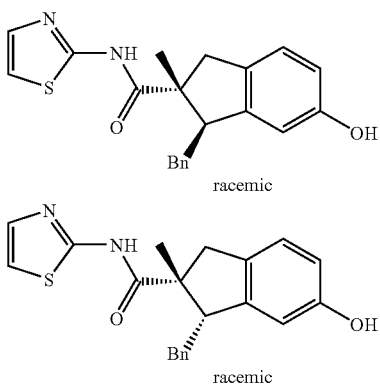

Using a procedure similar to the synthesis of Example 5, the mixture fractions from the synthesis of Example 187 was converted to Examples 188 (fast eluting isomer) and 189 (slow eluting isomer). MS Found for both: (M+H)⁺=365.

Examples 190 and 191 rac-(1R,2S)-2-methyl-6-(methyloxy)-1-(2-naphthalenyl)-N-1,3-thiazol-2-yl-2,3-dihydro-1H-indene-2-carboxamide; and rac-(1R,2R)-2-methyl-6-(methyloxy)-1-(2-naphthalenyl)-N-1,3-thiazol-2-yl-2,3-dihydro-1H-indene-2-carboxamide

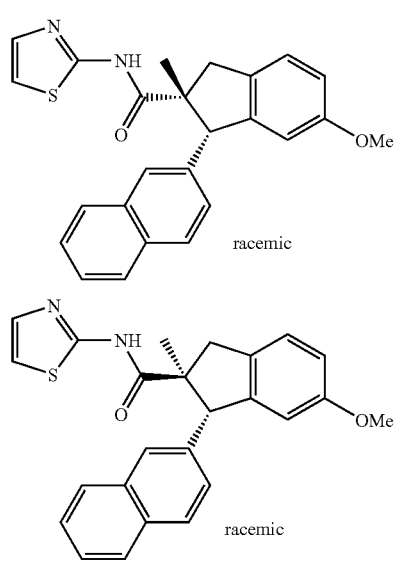

Using conditions similar to reactions 179c-d and 179f-z, the keto ester from reaction 179b was reacted with 2-naphthylmagnesium bromide and converted to Examples 190 (fast eluting isomer) and 191 (slow eluting isomer). MS Found for both: (M+H)⁺=415.

Examples 192 and 193 rac-(1R,2S)-6-hydroxy-2-methyl-1-(2-naphthalenyl)-N-1,3-thiazol-2-yl-2,3-dihydro-1H-indene-2-carboxamide; and rac-(1R,2R)-6-hydroxy-2-methyl-1-(2-naphthalenyl)-N-1,3-thiazol-2-yl-2,3-dihydro-1H-indene-2-carboxamide

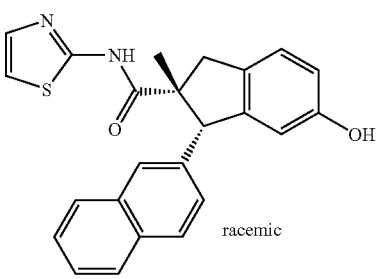

-continued

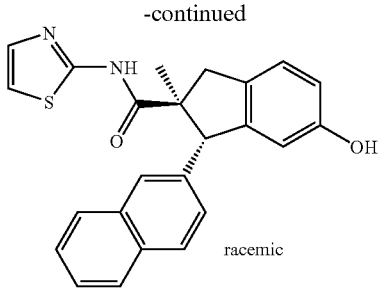

racemic

Using a procedure similar to the synthesis of Example 5, Examples 190 and 191 were converted to Examples 192 and 193 respectively. MS Found for both: (M+H)⁺=401.

Example 194 rac-(1R,2S)-6-cyano-2-methyl-1-(2-naphthalenyl)-N-1,3-thiazol-2-yl-2,3-dihydro-1H-indene-2-carboxamide

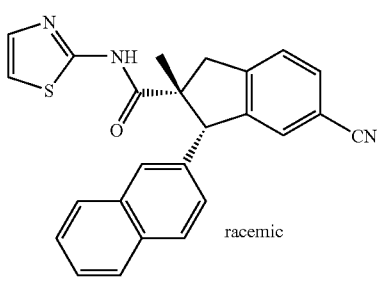

racemic (194a) Following a procedure similar to reaction 179a, the 6-bromoindanone (4.13 g, 19.6 mmol) was reacted with dimethylcarbonate to give the keto ester.

(194b) Following a procedure similar to reaction 179b, the keto ester from reaction 194a was reacted with iodomethane to give the methylated keto ester (3.7 g, 67% for 2 steps). MS Found: (M+H)⁺=283, 285.

(194c) Following a procedure similar to reaction 179c, the keto ester from reaction 194b (1.01 g, 3.57 mmol) was reacted with 2-naphthylmagnesium bromide to give the alcohol (1.37 mg, 93%). MS Found: (M+Na)⁺=433, 435.

(194d) Following a procedure similar to reaction 179d, the alcohol from reaction 194c (1.24 g, 3 mmol) was reduced to a mixture of cis and trans indane esters. MS Found: (M+Na)⁺=417, 419.

(194e) Following a procedure similar to reaction 179f, the esters from reaction 194d was hydrolyzed to give the bromo acids.

(194f) Following a procedure similar to the preparation of Example 85, the bromo acids from reaction 194e was converted to the cyano acids and separated by reverse-phase HPLC (70-90% solvent B gradient) to give the cis cyano acid (184 mg, 25% for 3 steps) and trans cyano acid (348 mg, 47% for 3 steps). MS Found for both: (M+H)⁺=328.

(194f) Following a procedure similar to the preparation of Example 2, the cis cyano acid from reaction 194f (11 mg, 0.034 mmol) was reacted with 2-aminothiazole to give Example 194 (11 mg, 79%). MS Found: (M+H)⁺=410.

Example 195 rac-(1R,2S)-6-cyano-2-methyl-1-(2-naphthalenyl)-N-1,3,4-thiadiazol-2-yl-2,3-dihydro-1H-indene-2-carboxamide

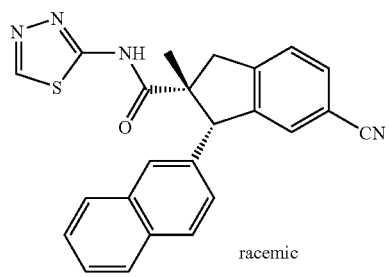

racemic

Following a procedure similar to the preparation of Example 2, the cis cyano acid from reaction 194 (28 mg, 0.085 mmol) was reacted with 2-amino-1,3,4-thiadiazole to give Example 195 (25 mg, 71%). MS Found: (M+H)⁺=411.

Example 196 rac-(1R,2R)-6-cyano-2-methyl-1-(1-naphthalenyl)-N-1,3-thiazol-2-yl-2,3-dihydro-1H-indene-2-carboxamide

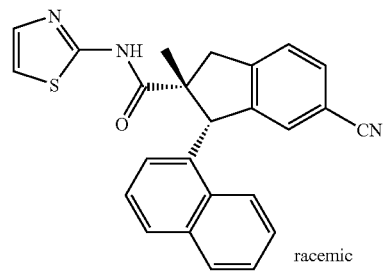

racemic

Using conditions similar to reactions 194c-g, the keto ester from reaction 194b was reacted with 1-naphthylmagnesium bromide and converted to Example 196. MS Found: (M+H)⁺=410.

Example 197 rac-(1R,2R)-6-cyano-2-methyl-1-(1-naphthalenyl)-N-1,3,4-thiadiazol-2-yl-2,3-dihydro-1H-indene-2-carboxamide

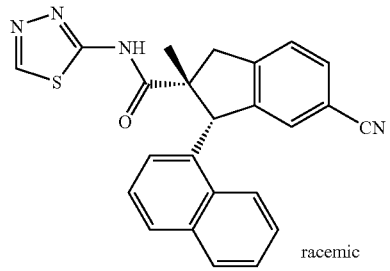

racemic

Using conditions similar to reactions 194c-g, the keto ester from reaction 194b was reacted with 1-naphthylmagnesium bromide and converted to Example 197. MS Found: (M+H)⁺=411.

Example 198 rac-(1R,2S)-1-(4-biphenylyl)-6-cyano-2-methyl-N-1,3-thiazol-2-yl-2,3-dihydro-1H-indene-2-carboxamide

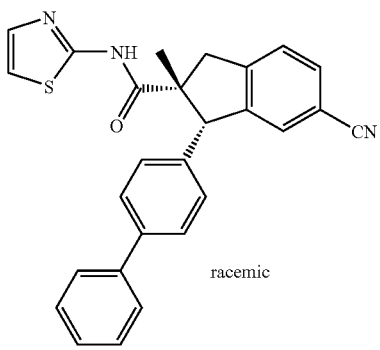

racemic

Using conditions similar to reactions 194c-g, the keto ester from reaction 194b was reacted with 4-biphenylmagnesium bromide and converted to Example 198. MS Found: (M+H)$^+$=436.

Example 199 rac-(1R,2S)-1-(4-biphenylyl)-6-cyano-2-methyl-N-1,3,4-thiadiazol-2-yl-2,3-dihydro-1H-indene-2-carboxamide

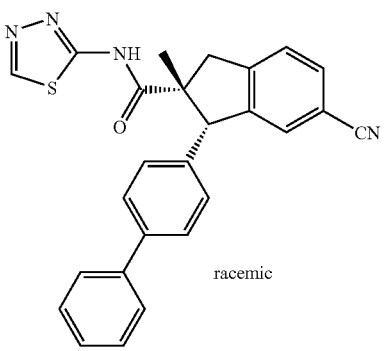

racemic

Using conditions similar to reactions 194c-g, the keto ester from reaction 194b was reacted with 4-biphenylmagnesium bromide and converted to Example 199. MS Found: (M+H)$^+$=437.

Examples 200 and 201 rac-(1R,2S)-2-methyl-6-(methyloxy)-N-1,3-thiazol-2-yl-1-(2-thienyl)-2,3-dihydro-1H-indene-2-carboxamide, and rac-(1R,2R)-2-methyl-6-(methyloxy)-N-1,3-thiazol-2-yl-1-(2-thienyl)-2,3-dihydro-1H-indene-2-carboxamide

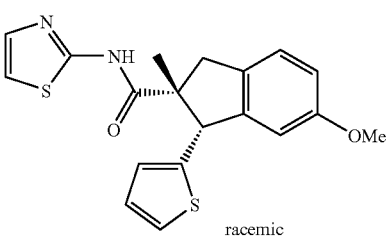

racemic

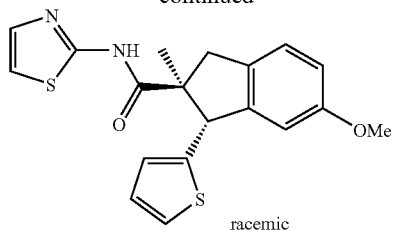

racemic

Using conditions similar reactions 179c-d and 179f-g, the keto ester from reaction 179b was reacted with thiophen-2-ylmagnesium bromide and converted to Examples 200 (fast eluting isomer) and 201 (slow eluting isomer). MS Found for both: (M+H)$^+$=371.

Examples 202 and 203 rac-(1R,2S)-6-hydroxy-2-methyl-N-1,3-thiazol-2-yl-1-(2-thienyl)-2,3-dihydro-1H-indene-2-carboxamide; and rac-(1R,2R)-6-hydroxy-2-methyl-N-1,3-thiazol-2-yl-1-(2-thienyl)-2,3-dihydro-1H-indene-2-carboxamide

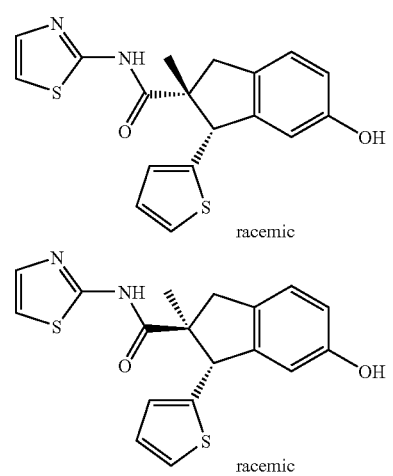

Using a procedure similar to the synthesis of Example 5, Examples 200 and 201 were converted to Examples 202 and 203 respectively. MS Found for both: (M+H)$^+$=357.

Example 204 rac-(1R,2S)-6-cyano-2-methyl-N-1,3-thiazol-2-yl-1-(2-thienyl)-2,3-dihydro-1H-indene-2-carboxamide

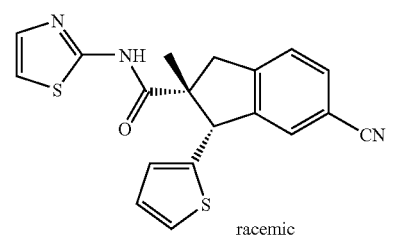

racemic

Using conditions similar to reactions 194c-g, the keto ester from reaction 194b was reacted with thiophene-2-ylmagnesium bromide and converted to Example 204. MS Found: (M+H)$^+$=366.

Example 205 rac-(1R,2R)-6-cyano-2-methyl-N-1,3-thiazol-2-yl-1-(2-thienyl)-2,3-dihydro-1H-indene-2-carboxamide

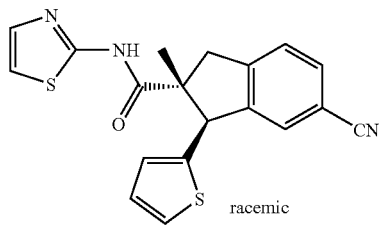

Using conditions similar to reactions 194c-g, the keto ester from reaction 194b was reacted with thiophen-2-ylmagnesium bromide and converted to Example 205. MS Found: (M+H)$^+$=366.

Example 206 rac-(1R,2S)-6-cyano-2-methyl-N-1,3,4-thiadiazol-2-yl-1-(2-thienyl)-2,3-dihydro-1H-indene-2-carboxamide

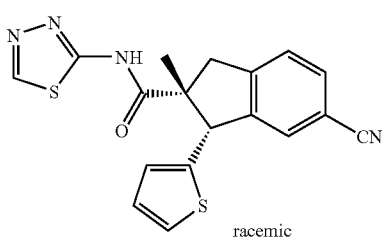

Using conditions similar to reactions 194c-g, the keto ester from reaction 194b was reacted with thiophen-2-ylmagnesium bromide and converted to Example 206. MS Found: (M+H)$^+$=367.

Example 207 rac-(1R,2R)-6-cyano-2-methyl-N-1,3,4-thiadiazol-2-yl-1-(2-thienyl)-2,3-dihydro-1H-indene-2-carboxamide

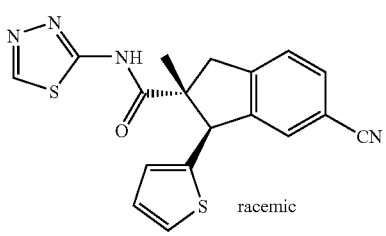

Using conditions similar to reactions 194c-g, the keto ester from reaction 194b was reacted with thiophen-2-ylmagnesium bromide and converted to Example 207. MS Found: (M+H)$^+$=367.

Examples 208 and 209 rac-(1R,2S)-2-methyl-6-(methyloxy)-N-1,3-thiazol-2-yl-1-(3-thienyl)-2,3-dihydro-1H-indene-2-carboxamide; and rac-(1R,2R)-2-methyl-6-(methyloxy)-N-1,3-thiazol-2-yl-1-(3-thienyl)-2,3-dihydro-1H-indene-2-carboxamide

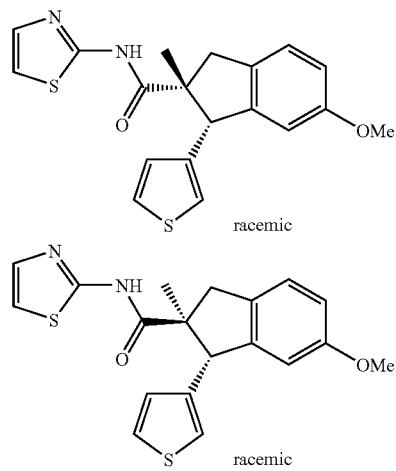

Using conditions similar reactions 179c-d and 179f-g, the keto ester from reaction 179b was reacted with thiophen-3-ylmagnesium iodide and converted to Examples 208 (fast eluting isomer) and 209 (slow eluting isomer). MS Found for both: (M+H)$^+$=371.

Examples 210 and 211 rac-(1R,2S)-6-hydroxy-2-methyl-N-1,3-thiazol-2-yl-1-(3-thienyl)-2,3-dihydro-1H-indene-2-carboxamide; and rac-(1R,2S)-6-hydroxy-2-methyl-N-1,3-thiazol-2-yl-1-(3-thienyl)-2,3-dihydro-1H-indene-2-carboxamide

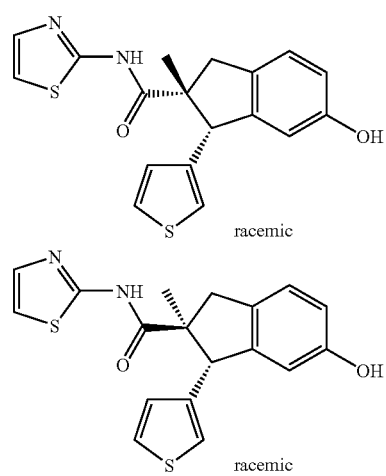

Using a procedure similar to the synthesis of Example 5, Examples 208 and 209 were converted to Examples 210 and 211 respectively. MS Found for both: (M+H)$^+$=357.

Example 212 rac-(1R,2S)-6-cyano-2-methyl-1-(5-methyl-2-thienyl)-N-1,3-thiazol-2-yl-2,3-dihydro-1H-indene-2-carboxamide

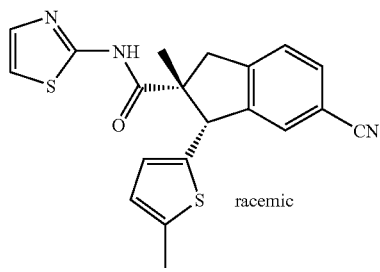

Using conditions similar to reactions 194c-g, the keto ester from reaction 194b was reacted with 5-methyl-2-thienylmagnesium bromide and converted to Example 212. MS Found: $(M+H)^+=380$.

Example 213 rac-(1R,2S)-6-cyano-2-methyl-1-(5-methyl-2-thienyl)-N-1,3,4-thiadiazol-2-yl-2,3-dihydro-1H-indene-2-carboxamide

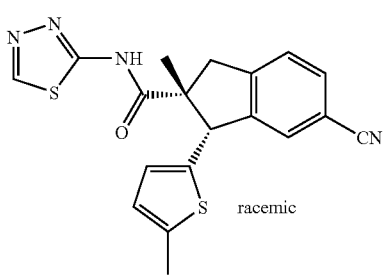

Using conditions similar to reactions 194c-g, the keto ester from reaction 194b was reacted with 5-methyl-2-thienylmagnesium bromide and converted to Example 213. MS Found: $(M+H)^+=381$.

Example 214 rac-(1R,2S)-6-cyano-2-methyl-1-(3-(methyloxy)phenyl)-N-1,3-thiazol-2-yl-2,3-dihydro-1H-indene-2-carboxamide

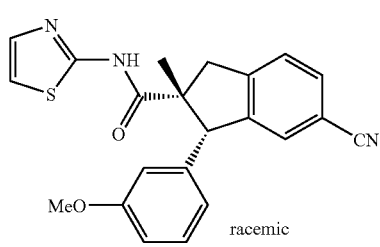

Using conditions similar to reactions 194c-g, the keto ester from reaction 194b was reacted with 3-methoxyphenylmagnesium bromide and converted to Example 214. MS Found: $(M+H)^+=390$.

Example 215 rac-(1R,2S)-6-cyano-2-methyl-1-(3-(methyloxy)phenyl)-N-1,3,4-thiadiazol-2-yl-2,3-dihydro-1H-indene-2-carboxamide

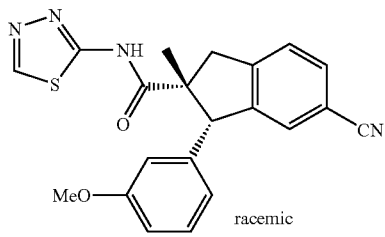

Using conditions similar to reactions 194c-g, the keto ester from reaction 194b was reacted with 3-methoxyphenylmagnesium bromide and converted to Example 215. MS Found: $(M+H)^+=391$.

Example 216 rac-(1R,2S)-6-cyano-1-(3-hydroxyphenyl)-2-methyl-N-1,3-thiazol-2-yl-2,3-dihydro-1H-indene-2-carboxamide

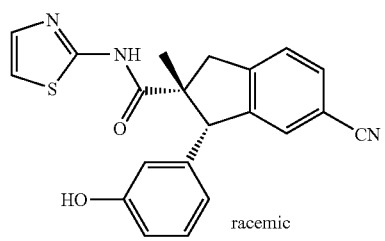

Using a procedure similar to the synthesis of Example 5, Examples 214 was converted to Example 216. MS Found: $(M+H)^+=376$.

Example 217 rac-(1R,2S)-6-cyano-1-(3-hydroxyphenyl)-2-methyl-N-1,3,4-thiadiazol-2-yl-2,3-dihydro-1H-indene-2-carboxamide

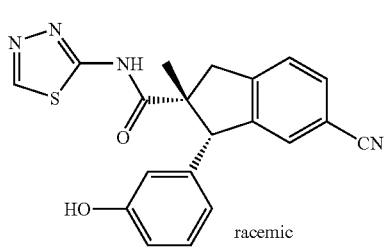

Using a procedure similar to the synthesis of Example 5, Examples 215 was converted to Example 217. MS Found: $(M+H)^+=377$.

Example 218 rac-(1R,2S)-6-cyano-2-methyl-1-(3-(phenyloxy)phenyl)-N-1,3,4-thiadiazol-2-yl-2,3-dihydro-1H-indene-2-carboxamide

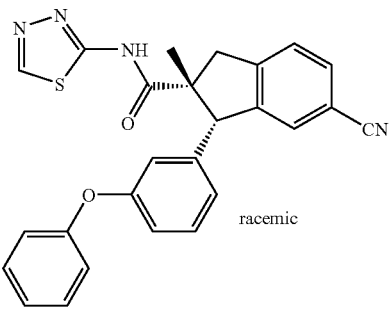

Following a procedure similar to the preparation of Example 155, Example 217 (13 mg, 0.035 mmol) was converted to Example 218 (3.4 mg, 22%). MS Found: (M+H)$^+$=453.

Example 219 rac-(1R,2S)-1-(3-bromophenyl)-6-cyano-2-methyl-N-1,3-thiazol-2-yl-2,3-dihydro-1H-indene-2-carboxamide

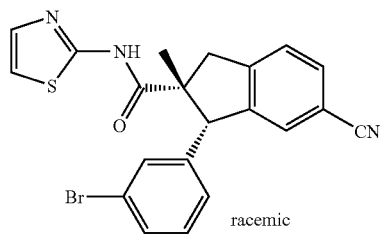

(219a-e) Using a procedure similar to reactions 3b-f, ethyl (4-iodobenzyl)acetate and 3-bromobenzaldehyde were reacted to give a mixture of cis and trans 1-(3-bromophenyl)-6-iodo-indane acids. MS Found: (M+Na)$^+$=479, 481.

(219f) Following a procedure similar to the preparation of Example 85 except that the microwave reaction was run at 150° C., the acids from 219e was converted to bromo cyano acids and dicyano acids. The mixture was separated into cis and trans isomers of the corresponding acids by preparative reverse-phase HPLC (60-85% solvent B gradient).

(219f) Following a procedure similar to the preparation of Example 2, the cis bromo cyano acid from reaction 219f (6 mg, 0.017 mmol) was reacted with 2-aminothiazole to give Example 219 (4.3 mg, 96%). MS Found: (M+H)$^+$=438, 440.

Example 220 rac-(1R,2S)-1-(3-bromophenyl)-6-cyano-2-methyl-N-1,3,4-thiadiazol-2-yl-2,3-dihydro-1H-indene-2-carboxamide

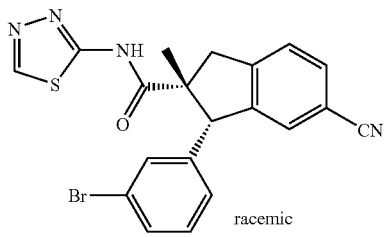

Following a procedure similar to the preparation of Example 2, the cis bromo cyano acid from reaction 219f (7 mg, 0.02 mmol) was reacted with 2-amino-1,3,4-thiadiazole to give Example 220 (5.3 mg, 60%). MS Found: (M+H)$^+$=439, 441.

Example 221 rac-(1R,2S)-6-cyano-1-(3-cyanophenyl)-2-methyl-N-1,3-thiazol-2-yl-2,3-dihydro-1H-indene-2-carboxamide

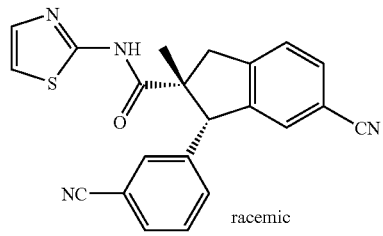

Following a procedure similar to the preparation of Example 2, the cis dicyano acid from reaction 219 (2.6 mg, 0.009 mmol) was reacted with 2-aminothiazole to give Example 221 (2.3 mg, 67%). MS Found: (M+H)$^+$=385.

Example 222 rac-(1R,2S)-6-cyano-1-(3-cyanophenyl)-2-methyl-N-1,3,4-thiadiazol-2-yl-2,3-dihydro-1H-indene-2-carboxamide

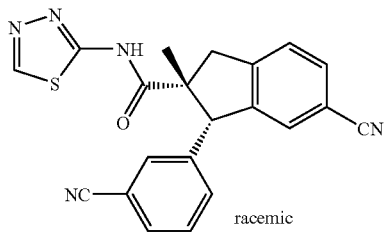

Following a procedure similar to the preparation of Example 2, the cis dicyano acid from reaction 219f (4 mg, 0.013 mmol) was reacted with 2-amino-1,3,4-thiadiazole to give Example 222 (2.7 mg, 53%). MS Found: (M+H)$^+$=386.

Example 223 rac-(1R,2R)-2-methyl-1-phenyl-N-(4-((4-(4-pyridinyl)phenyl)methyl)-1,3-thiazol-2-yl)-2,3-dihydro-1H-indene-2-carboxamide

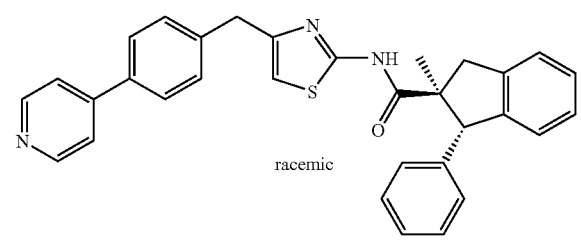

Using a procedure similar to reaction 8d, the ester from reaction 18c was reacted with 2-amino-4-(4-(pyridin-4-yl)benzyl)thiazole (for synthesis, see WO2004009017) to give Example 223. MS Found: (M+H)$^+$=502.

Example 224 rac-(1R,2R)-1-phenyl-N-(4-((4-(4-pyridinyl)phenyl)methyl)-1,3-thiazol-2-yl)-2,3-dihydro-1H-indene-2-carboxamide

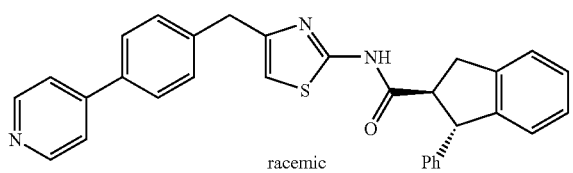

(224a) Benzaldehyde (3.05 mL, 1 eq) was added to a mixture of ethyl benzoylacetate (5.47 mL, 30.0 mmol) and aluminum chloride (6.00 g, 1.5 eq) in nitroethane (100 mL) at room temperature. The mixture was heated to 110° C. for 3 h, cooled to room temperature, treated with 1 N HCl (200 mL) and extracted with EtOAc (3×100 mL). The combined extracts were washed with 1 N HCl (25 mL), water (25 mL), brine (25 mL), dried (MgSO$_4$) and concentrated. Silica gel chromatography (EtOAc-hexane, 8:92 then 10:90 then 15:85) gave impure keto ester (5.77 g), which was taken to next step without further purification. MS Found: (M+Na)$^+$=303.

(224b) NaBH$_4$ (5.67 g, 150 mmol) was added in several portions to the keto ester from reaction 224a in MeOH at 0° C. After 4 h at 0° C., the mixture was quenched with saturated NH$_4$Cl (200 mL). After evaporation of MeOH in vacuo, the residue was extracted with EtOAc (3×100 mL). The combined extracts were washed with water (10 mL), brine (10 mL), dried (MgSO$_4$) and concentrated. The crude hydroxyl ester was taken to next step without purification.

(224c) Diisopropylethylamine (16.9 mL), methanesulfonyl chloride (3.17 mL) and DMAP (250 mg) were added successively to the crude hydroxyl ester from reaction 224b in CH$_2$Cl$_2$ (100 mL) at 0° C. After 1 h at this temperature, saturated NH$_4$Cl (200 mL) was added. The two phases were separated. The aqueous phase was extracted with CH$_2$Cl$_2$ (2×100 mL). The combined CH$_2$Cl$_2$ extracts were washed with water (20 mL), brine (20 mL), dried (MgSO$_4$) and concentrated. Silica gel chromatography (EtOAc-hexane, 3:97 then 5:95 then 8:92 then 10:90) gave ethyl 3-phenyl-1H-indene-2-carboxylate (496 mg, 9% for three steps). MS Found: (M+Na)$^+$=287.

(224d) A mixture of the ester from reaction 224c (389 mg, 1.47 mmol), 10% Pd/C (389 mg) and EtOH (10 mL) was hydrogenated under 50 psi H$_2$ for 12 h. Additional Pd/C (389 mg) was added and the mixture hydrogenated for additional 24 h. The catalyst was removed by filtration. The filtrate was concentrated to give the desired cis-indane ester (391 mg, 100%). MS Found: (M+Na)$^+$=289.

(224e) A mixture of the ester from reaction 224d (84 mg, 0.316 mmol), 1 N NaOH (2 mL), THF (1 mL) and MeOH (0.5 mL) was stirred at 70° C. for 4 h, then quenched with 1 N HCl (3 mL). After evaporation of organic solvents in vacuo, the residue was extracted with EtOAc (2×15 mL). The combined extracts were washed with water (3 mL), brine (3 mL), dried (MgSO$_4$) and concentrated to give a 4:1 mixture of trans and cis isomers (53.2 mg, 71%). MS Found: (M−H)$^−$=237.

(224f) Using a procedure similar to reaction Id, the acid from reaction 224e (12.8 mg, 0.054 mmol) was reacted with 2-amino-4-(4-(pyridin-4-yl)benzyl)thiazole to give Example 224 (20.7 mg, 64%), as a TFA salt. MS Found: (M+H)$^+$=488.

Example 225 rac-(1R,2S)-1-phenyl-N-(4-((4-(4-pyridinyl)phenyl)methyl)-1,3-thiazol-2-yl)-2,3-dihydro-1H-indene-2-carboxamide

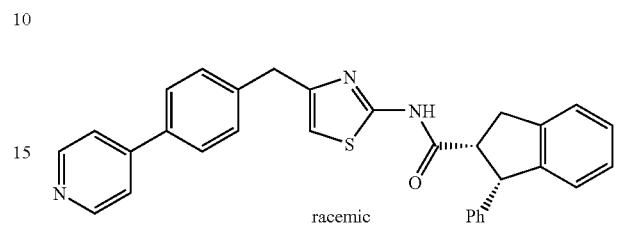

(225a) A mixture of the cis-indane ester from reaction 224d (35.2 mg, 0.137 mmol), MeOH (2 mL) and concentrated HCl (0.1 mL) was heated at 70° C. for 20 h, then concentrated to give the corresponding methyl ester (30.9 mg, 90%). MS Found: (M+Na)$^+$=275.

(225b) Using a procedure similar to reaction 8d, the ester from reaction 225a (10.5 mg, 0.042 mmol) was reacted with 2-amino-4-(4-(pyridin-4-yl)benzyl)thiazole to give Example 225 (13.6 mg, 54%), as a TFA salt. MS Found: (M+H)$^+$=502.

Example 226 rac-(1R,2S)-2-methyl-1-phenyl-N-(4-((4-(4-pyridinyl)phenyl)methyl)-1,3-thiazol-2-yl)-2,3-dihydro-1H-indene-2-carboxamide

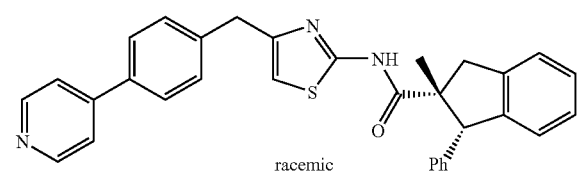

Using a sequence similar to the synthesis of Example 21, Example 226 was prepared using 2-amino-4-(4-(pyridin-4-yl)benzyl)thiazole. MS Found: (M+H)$^+$=502.

Example 227 rac-(1R,2S)-1-(2,4-dimethyl-1,3-thiazol-5-yl)-1-methyl-N-(4-((4-(4-pyridinyl)phenyl)methyl)-1,3-thiazol-2-yl)-2,3-dihydro-1H-indene-2-carboxamide

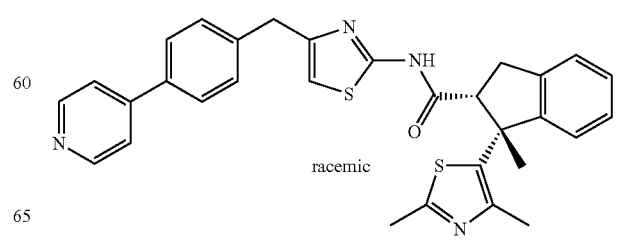

(227a-c) Using a procedure similar to reactions 10a-c, the thiazole-substituted indane esters were prepared from 5-acetyl-2,4-dimethylthiazole and methyl diethylphosphonoacetate. MS Found: (M+H)$^+$=302.

(227d) Using a procedure similar to reaction 10d, the esters from reaction 227c were hydrolyzed and purified by reverse phase HPLC (45-90% solvent B gradient) to give the first isomer as the trans acid and the second isomer as the cis acid. MS Found: (M+H)$^+$=288.

(227e) Using a procedure similar to the synthesis of Example 2, the trans acid from reaction 227d was reacted with 2-amino-4-(4-(pyridin-4-yl)benzyl)thiazole to give Example 227. MS Found: (M+H)$^+$=537.

Examples 228 and 229 rac-(1R,2S)-1-methyl-1-phenyl-N-(4-((4-(4-pyridinyl)phenyl)methyl)-1,3-thiazol-2-yl)-2,3-dihydro-1H-indene-2-carboxamide, and rac-(1R,2R)-1-methyl-1-phenyl-N-(4-((4-(4-pyridinyl)phenyl)methyl)-1,3-thiazol-2-yl)-2,3-dihydro-1H-indene-2-carboxamide, respectively

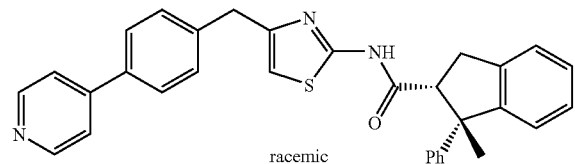

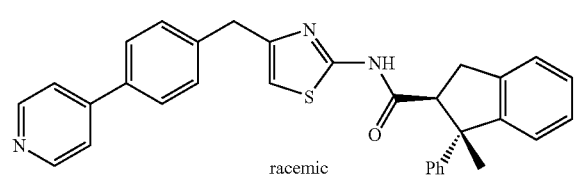

Using a sequence similar to the synthesis of Examples 10 and 11, Examples 228 and 229 were prepared using 2-amino-4-(4-(pyridin-4-yl)benzyl)thiazole. MS Found: (M+H)$^+$=502.

Example 230 rac-(1R,2R)-1-(1,1-dimethylethyl)-1-methyl-N-(4-((4-(4-pyridinyl)phenyl)methyl)-1,3-thiazol-2-yl)-2,3-dihydro-1H-indene-2-carboxamide

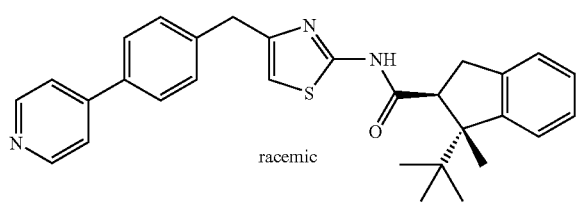

(230a-c) Using a sequence similar to reactions 10a-c, the 1-t-butyl-substituted t-butyl indanecarboxylates were prepared from pinacolone and t-butyl diethylphosphonoacetate.

(230d) The esters from reaction 230c were treated with trifluoroacetic acid to give the acids. MS Found: (M+H)$^+$=233.

(230e) Using a procedure similar to the synthesis of Example 2, the acids from reaction 230d were coupled with 2-amino-4-(4-(pyridin-4-yl)benzyl)thiazole and purified by reverse-phase HPLC (70-100% solvent B gradient) to give the first isomer as Example 230. MS Found: (M+H)$^+$=482.

Example 231 rac-(1R,2S)-1-methyl-1-(4-pyridinyl)-N-(4-((4-(4-pyridinyl)phenyl)methyl)-1,3-thiazol-2-yl)-2,3-dihydro-1H-indene-2-carboxamide

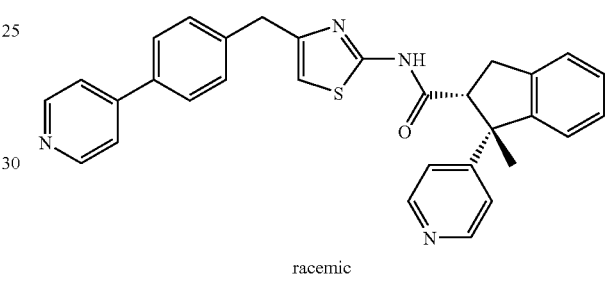

Using a procedure similar to reaction Id, the cis acid from reaction 12d (16.6 mg, 0.057 mmol) was reacted with 2-amino-4-(4-(pyridin-4-yl)benzyl)thiazole to give Example 231 (12.4 mg, 30%). MS Found: (M+H)$^+$=503.

Example 232 rac-(1R,2R)-1-methyl-1-(4-pyridinyl)-N-(4-((4-(4-pyridinyl)phenyl)methyl)-1,3-thiazol-2-yl)-2,3-dihydro-1H-indene-2-carboxamide

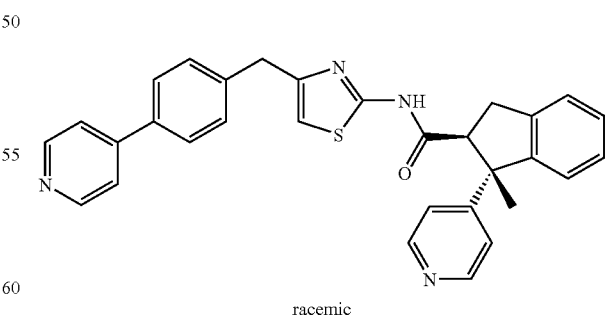

Using a procedure similar to reaction Id, the trans acid from reaction 12d (40.7 mg, 0.111 mmol) was reacted with 2-amino-4-(4-(pyridin-4-yl)benzyl)thiazole to give Example 232 (34.1 mg, 42%). MS Found: (M+H)$^+$=503.

Examples 233 and 234

(1S,2S)-1-methyl-1-(4-pyridinyl-N-(4-((4-(4-pyridinyl)phenyl)methyl)-1,3-thiazol-2-yl)-2,3-dihydro-1H-indene-2-carboxamide, and (1R,2R)-1-methyl-1-(4-pyridinyl)-N-(4-((4-(4-pyridinyl)phenyl)methyl)-1,3-thiazol-2-yl)-2,3-dihydro-1H-indene-2-carboxamide and (1S,2S)—N-(4-(4-(pyridin-4-yl)benzyl)thiazol-2-yl)-1-methyl-1-(pyridin-4-yl)-2,3-dihydro-1H-indene-2-carboxamide.

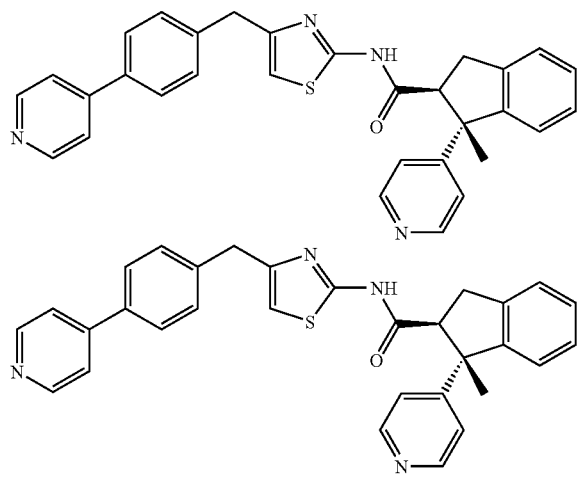

Example 232 was separated on Chiralcel-OD HPLC column (30×250 mm, 5μ packing particle size, 12.5% MeOH—12.5% EtOH-75% Heptane, 20 mL/min) to give the fast enantiomer as Example 234 and slow enantiomer as Example 233. MS Found: $(M+H)^+=503$.

Example 235 rac-(1R,2R)-1-methyl-1-(3-pyridinyl)-N-(4-((4-(4-pyridinyl)phenyl)methyl)-1,3-thiazol-2-yl)-2,3-dihydro-1H-indene-2-carboxamide

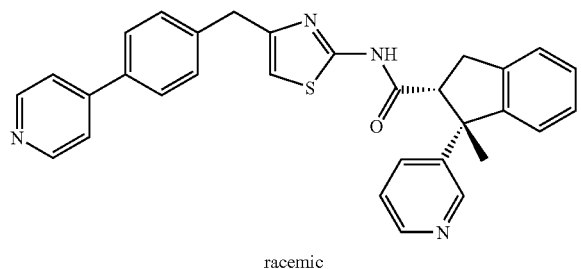

racemic (235a-c) Using a procedure similar to reactions 10a-c, the 1-(pyridine-3-yl)-substituted indane esters were prepared from 3-acetylpyridine and methyl diethylphosphonoacetate. MS Found: $(M+H)^+=268$.

(235d) Using a procedure similar to reaction 10d, the esters from reaction 235c was hydrolyzed and purified by reverse phase HPLC (40-70% solvent B gradient) to give the first isomer as the trans acid and the second isomer as the cis acid. MS Found: $(M+H)^+=254$.

(235e) Using a procedure similar to the synthesis of Example 2, the cis acid from reaction 235d was reacted with 2-amino-4-(pyridin-4-yl)benzyl)thiazole to give Example 235. MS Found: $(M+H)^+=503$.

Example 236 rac-(1R,2S)-1-methyl-1-(3-pyridinyl)-N-(4-((4-(4-pyridinyl)phenyl)methyl)-1,3-thiazol-2-yl)-2,3-dihydro-1H-indene-2-carboxamide

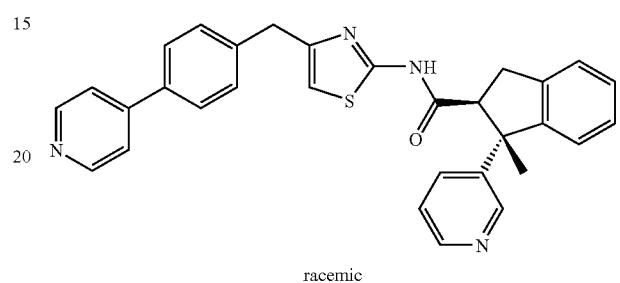

racemic

Using a procedure similar to the synthesis of Example 2, the trans acid from reaction 235d (22.5 mg, 0.061 mmol) was reacted with 2-amino-4-(4-(pyridin-4-yl)benzyl)thiazole to give Example 236 (18.2 mg, 41%). MS Found: $(M+H)^+=503$.

Example 237

1-methyl-1-(2-pyridinyl)-N-(4-((4-(4-pyridinyl)phenyl)methyl)-1,3-thiazol-2-yl)-2,3-dihydro-1H-indene-2-carboxamide

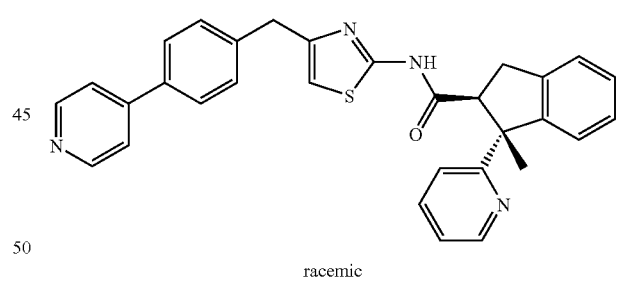

racemic (237a-c) Using a procedure similar to reactions 10a-c, the 1-(pyridine-2-yl)-substituted indane esters were prepared from 2-acetylpyridine and methyl diethylphosphonoacetate. MS Found: $(M+H)^+=268$.

(237d) Using a procedure similar to reaction 10d, the esters from reaction 237c were hydrolyzed and purified by reverse phase HPLC (40-80% solvent B gradient) to give the first isomer as the trans acid and the second isomer as the cis acid. MS Found: $(M+H)^+=254$.

(237e) Using a procedure similar to the synthesis of Example 2, the trans acid from reaction 237d was reacted with 2-amino-4-(4-(pyridin-4-yl)benzyl)thiazole to give Example 237. MS Found: $(M+H)^+=503$.

Example 238 rac-(1S,2S)—N-(4-(4-fluoro-1-naphthalenyl)-1,3-thiazol-2-yl)-1-methyl-2,3-dihydro-1H-indene-2-carboxamide

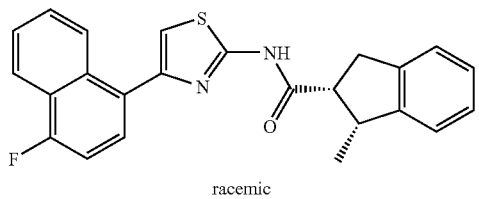

racemic (238a) Using a procedure similar to the reaction 124a, the 3-methyl-1H-indene-2-carboxylic acid (96.8 mg, 0.556 mmol) was hydrogenated to give the cis-1-methyl-2-indanecarboxylic acid (89 mg, 91%). MS Found: $(M-H)^-=175$.

(238b) Using a procedure similar to the synthesis of Example 2, the acid from reaction 238a (26.4 mg, 0.15 mmol) was coupled with 2-amino-4-(4-fluoronaphthalen-1-yl)thiazole to give Example 238 (38.4 mg, 64%) as a 2:1 inseparable mixture of cis and trans isomers. MS Found: $(M+H)^+=403$.

Example 239 rac-(1S,2S)—N-(4-(3-(((3-chloro-4-(methyloxy)phenyl)amino)carbonyl)phenyl)-1,3-thiazol-2-yl)-1-methyl-2,3-dihydro-1H-indene-2-carboxamide

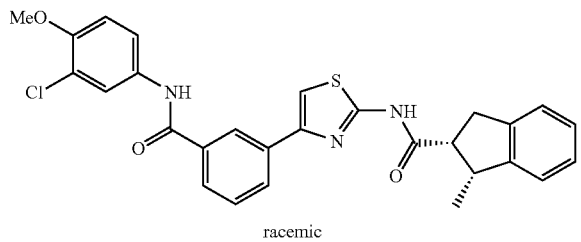

racemic

Using a procedure similar to the synthesis of Example 2, the acid from reaction 238a (24.6 mg, 0.14 mmol) was coupled with 3-(2-aminothiazol-4-yl)-N-(3-chloro-4-methoxyphenyl)benzamide to give Example 239 (46.6 mg, 64%) as a 3:2 inseparable mixture of cis and trans isomers. MS Found: $(M+H)^+=518$.

Example 240 rac-(1R,2R)-1-methyl-N-(4-((4-(4-pyridinyl)phenyl)methyl)-1,3-thiazol-2-yl)-2,3-dihydro-1H-indene-2-carboxamide

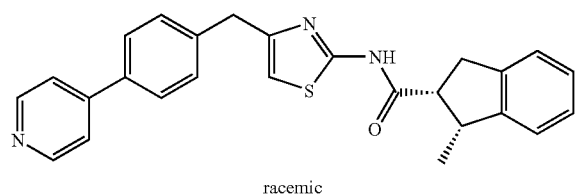

racemic

Following a procedure similar to reaction 8d, the ester from reaction 24b (8.4 mg, 0.044 mmol) was reacted with 2-amino-4-(4-(pyridin-4-yl)benzyl)thiazole to give Example 240 (2.8 mg, 12%), as a TFA salt. MS Found: $(M+H)^+=426$.

Example 241 rac-(1R,2S)—N-(4-(4-fluoro-1-naphthalenyl)-1,3-thiazol-2-yl)-1-methyl-2,3-dihydro-1H-indene-2-carboxamide

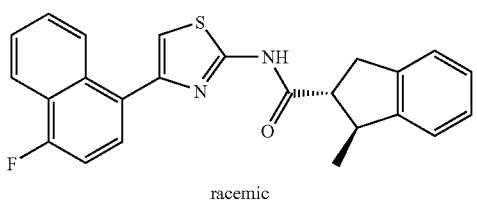

racemic (241a) Using a procedure similar to the reaction 10b, methyl but-3-enoate (2.56 g, 25.6 mmol) was deprotonated with LDA and reacted with 2-bromobenzyl bromide to give the alkylated product (3.56 g, 57%). MS Found: $(M+H)^+=269, 271$.

(241b) To a benzene (106 mL) solution of the product from reaction 241a (1 g, 3.74 mmol) and tributyltin hydride (1.58 g, 1.5 eq) was added AIBN (63 mg, 0.1 eq) under nitrogen atmosphere. The mixture was heated to reflux for 31 h, concentrated and purified by flash column chromatography (0-5% ethyl acetate-hexanes) to give a mixture of three isomers: methyl cis-1-methyl-2-indanecarboxylate (11%), methyl 1,2,3,4-tetrahydronaphthalene-2-carboxylate (10%) and methyl trans-1-methyl-2-indanecarboxylate (79%). MS Found: $(M+H)^+=191$.

(241c) A MeOH and water solution of the carboxylates from 241b and LiOH was stirred at room temperature for 24 h. The mixture was concentrated to give a mixture of acids.

(241d) Following a procedure similar to the synthesis of Example 2, the acids from reaction 241c were reacted with 2-amino-4-(4-fluoronaphthalen-1-yl)thiazole and purified by preparative reverse-phase HPLC (50-100% solvent B gradient) to give the slow eluding isomer as Example 241. MS Found: $(M+H)^+=403$.

Example 242 rac-(1R,2S)-1-methyl-N-(4-((4-(methyloxy)phenyl)methyl)-1,3-thiazol-2-yl)-2,3-dihydro-1H-indene-2-carboxamide

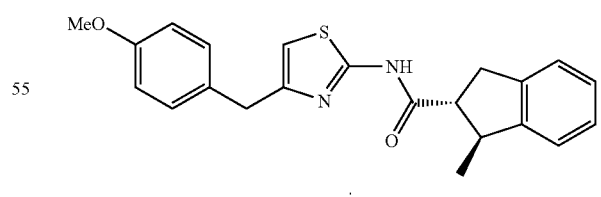

racemic

Following a procedure similar to the synthesis of Example 2, the acids from reaction 241c were reacted with 2-amino-4-(4-methoxybenzyl)imidazole and purified by reverse-phase HPLC (80-100% solvent B gradient) to the give the slow eluding isomer as Example 242. MS Found: $(M+H)^+=379$.

Example 243 rac-(1R,2S)—N-(4-(3-(((3-chloro-4-(methyloxy)phenyl)amino)carbonyl)phenyl)-1,3-thiazol-2-yl)-1-methyl-2,3-dihydro-1H-indene-2-carboxamide

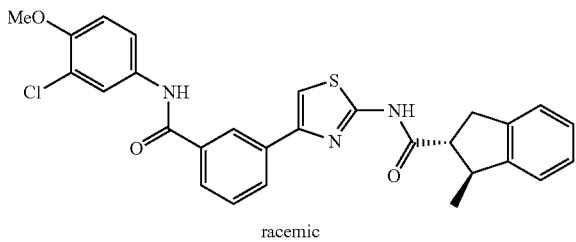

racemic

Following a procedure similar to the synthesis of Example 2, the acids from reaction 241c were reacted with 3-(2-aminothiazol-4-yl)-N-(3-chloro-4-methoxyphenyl)benzamide and purified by reverse-phase HPLC (80-100% solvent B gradient) to give the slow eluding isomer as Example 243. MS Found: $(M+H)^+=518$.

Example 244

3-phenyl-N-(4-((4-(4-pyridinyl)phenyl)methyl)-1,3-thiazol-2-yl)-1H-indene-2-carboxamide

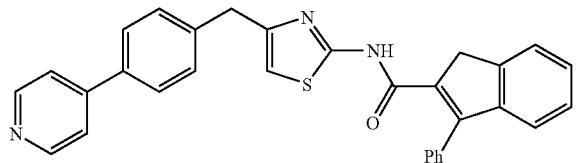

(244a) A mixture of the ester from reaction 224c (106.7 mg, 0.404 mmol), 1 N NaOH (4 mL), THF (4 mL) and MeOH (4 mL) was stirred at room temperature for 6 h, then acidified to pH 2 with 1 N HCl. After evaporation of organic solvents in vacuo, the residue was extracted with EtOAc (2×20 mL). The combined extracts were washed with water (4 mL), brine (4 mL), dried (MgSO$_4$) and concentrated. Reverse phase HPLC (80-100% solvent B gradient) gave the desired acid (17.0 mg, 18%). MS Found: $(M-H)^-=235$.

(244b) Using a procedure similar to reaction Id, the acid from reaction 244a (10.3 mg, 0.044 mmol) was reacted with 2-amino-4-(4-(pyridin-4-yl)benzyl)thiazole to give Example 244 (0.39 mg, 2%), as a TFA salt. MS Found: $(M+H)^+=486$.

Examples 245 and 246

3-oxo-1-phenyl-N-(4-((4-(4-pyridinyl)phenyl)methyl)-1,3-thiazol-2-yl)-2,3-dihydro-1H-indene-1-carboxamide, and 1-phenyl-N-(4-((4-(4-pyridinyl)phenyl)methyl)-1,3-thiazol-2-yl)-2,3-dihydro-1H-indene-1-carboxamide, respectively

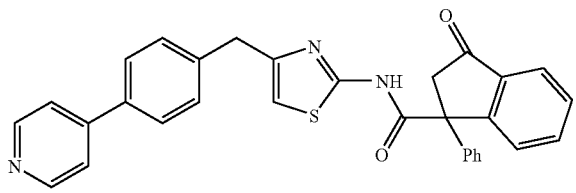

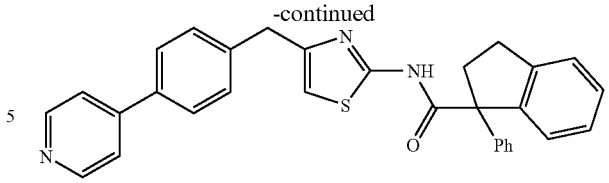

(245a) A mixture of 2-phenylacetonitrile (5.86 g, 50 mmol) and 2-chlorobenzonitrile (7.22 g, 1.05 eq) in DMF (15 mL) was added to a solution of potassium t-butoxide (13.0 g, 2.2 eq, 95%) in DMF (30 mL) cooled with an ice-water bath at a rate such that the internal temperature not exceeding 25° C. 30 min after completion of addition, t-butyl bromoacetate (8.86 mL, 1.2 eq) was added dropwise. The resultant mixture was stirred at room temperature for 24 h, then poured to a mixture of 0.1 N HCl (200 mL), heptane (30 mL) and toluene (15 mL). No solid precipitate was formed. The mixture was extracted with ether (3×150 mL). The combined extracts were washed with water, brine, dried (MgSO$_4$) and concentrated to about 50 mL of total volume to give a precipitate. The solid was collected by filtration, and washed with hexane, and ethyl acetate-hexane mixture (1:1) to give the desired tert-butyl 3-amino-1-cyano-1-phenyl-1H-indene-2-carboxylate (7.65 g, 46%). MS Found: $(M+H)^+=333$.

(245b) Sulfuric acid (4 mL) was slowly added to the ester from reaction 245a (1.00 g, 3.01 mmol) in acetic acid (6 mL) at 100° C. Gas evolution was observed during the addition. The mixture was stirred at 110° C. for 6 h, cooled to room temperature and extracted with toluene (3×30 mL). The combined extracts were washed with water (3×20 mL) and extracted with 1 N NaOH (3×30 mL). The combined aqueous extract was acidified to pH 2 with HCl and extracted with toluene (3×30 mL). The combined toluene extracts were washed with water (5 mL), brine (5 mL), dried (MgSO$_4$) and concentrated to give 3-oxo-1-phenyl-2,3-dihydro-1H-indene-1-carboxylic acid (652 mg, 86%) as a viscous liquid. MS Found: $(M+H)^+=253$.

(245c) A mixture of the acid from reaction 245b (640 mg, 2.54 mmol), 10% Pd/C (640 mg), acetic acid (20 mL) and concentrated HCl (10 mL) was mixed in a Parr-Shaker under 55 psi H$_2$ for 18 h. The catalyst was removed by filtration. The filtrate was concentrated to give a 1:1 mixture of unreacted starting material and 1-phenyl-2,3-dihydro-1H-indene-1-carboxylic acid (610 mg), which was used without separation.

(245d) Using a procedure similar to reaction Id, the acid mixture from reaction 245c (22.7 mg, 0.0934 mmol) was reacted with 2-amino-4-(4-(pyridin-4-yl)benzyl)thiazole to give Examples 245 (12.3 mg, 21%) and 246 (16.3 mg, 29%). MS Found: Example 245 $(M+H)^+=502$; Example 246 $(M+H)^+=488$.

Example 247

1-methyl-N-(4-((4-(methyloxy)phenyl)methyl)-1,3-thiazol-2-yl)-1-phenyl-1H-indene-2-carboxamide

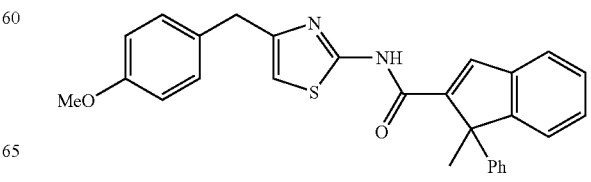

(247a) A solution of 3-methyl-3-phenyl-2,3-dihydroinden-1-one (5.052 g, 22.8 mmol, reference Roberge et. al *Synth. Commun.* 1979, 9, 129) in THF (20 mL) was added over 20 min to a 1 M hexane solution of LiHMDS (47.9 mL, 2.1 eq) in THF (200 mL) at −78° C. After 30 min at −78° C., methyl cyanoformate (2.33 g, 1.2 eq) in THF (20 mL) was added dropwise. After 30 min at −78° C., HMPA (3.97 mL, 1 eq) was added dropwise. The mixture was allowed to stirred overnight while slowly warm to room temperature. After addition of saturated NH$_4$Cl (200 mL), THF was evaporated in vacuo. The residue was extracted with ether (3×100 mL). The combined extracts were washed with brine (20 mL), dried (MgSO$_4$) and concentrated. Silica gel chromatography, twice, with EtOAc-hexane (5:95 then 7.5:92.5 then 10:90) gave the desired ketoester (0.666 g) and a mixture of the ketoester and unreacted starting material. MS Found: (M+Na)$^+$=303.

(247b) Following a procedure similar to reaction 224b, the ketoester from reaction 247a (0.666 g, 2.38 mmol) was reduced with NaBH$_4$ to give the desired hydroxyl ester (222 mg, impure). MS Found: (M+Na)$^+$=305.

(247c) Following a procedure similar to reaction 224c, the hydroxyl ester from reaction 247b was converted to methyl 1-methyl-1-phenyl-1H-indene-2-carboxylate (147 mg, 23% for 2 steps). MS Found: (M+H)$^+$=287.

(247d) A mixture of the ester from reaction 247c (147 mg, 0.557 mmol), 1 N NaOH (5 mL) and MeOH (10 mL) was stirred at 70° C. for 4 h, concentrated to remove MeOH, acidified with concentrated HCl until pH under 2, and extracted with EtOAc (3×10 mL). The combined extracts were washed with brine (2 mL), dried (MgSO$_4$) and concentrated to give the desired acid (132 mg, 95%). MS Found: (M+Na)$^+$=273.

(247e) Using a procedure similar to the synthesis of Example 2, the acid from reaction 247d (12.5 mg, 0.050 mmol) was reacted with 2-amino-4-(4-methoxybenzyl)thiazole (for synthesis, see WO2004009017) to give Example 247 (9.5 mg, 42%). MS Found: (M+H)$^+$=453.

Example 248

1-methyl-1-phenyl-N-(4-((4-(4-pyridinyl)phenyl)methyl)-1,3-thiazol-2-yl)-1H-indene-2-carboxamide

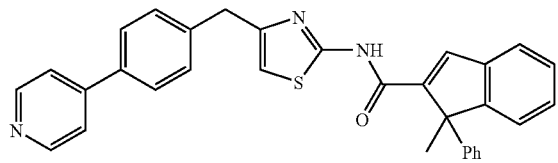

Using a procedure similar to the synthesis of Example 2, the acid from reaction 247d (12.5 mg, 0.050 mmol) was reacted with 2-amino-4-(4-(pyridin-4-yl)benzyl)thiazole to give Example 248 (7.0 mg, 23%), as a TFA salt. MS Found: (M+H)$^+$=500.

Examples 249 and 250

N-(4-((4-(4-pyridinyl)phenyl)methyl)-1,3-thiazol-2-yl)-2',3'-dihydrospiro[cyclohex-2-ene-1,1'-indene]-2'-carboxamide, and N-(4-((4-(4-pyridinyl)phenyl)methyl)-1,3-thiazol-2-yl)-2',3'-dihydrospiro[cyclohex-3-ene-1,1'-indene]-2'-carboxamide, respectively

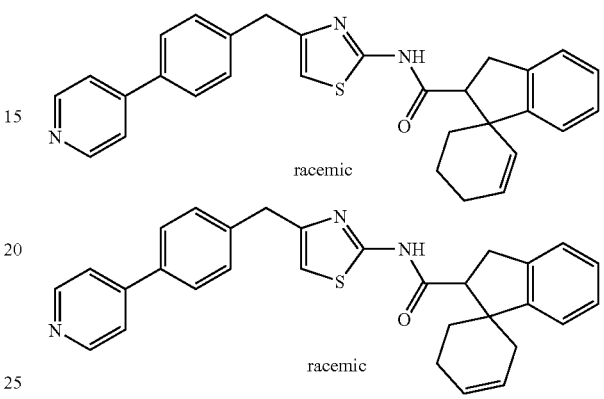

(249a) Using a procedure similar to the reaction 3a, 1-cyclohexenylacetic acid (3.5 g, 24.5 mmol) was converted to its methyl ester (2.75 g, 71%). MS Found: (M+H)$^+$=155.

(249b) Using a procedure similar to the reaction 10b, the ester from reaction 249a (1.32 g, 8.56 mmol) was deprotonated by LDA and reacted with 2-bromobenzyl bromide to give the alkylated product (2.11 g, 67%). MS Found: (M+Na)$^+$=393.

(261c) Using a procedure similar to the reaction 10c, the product from reaction 249b (0.99 g, 2.67 mmol) was cyclized to give a mixture of indane esters (0.38 g, 59%). MS Found: (M+Na)$^+$=265.

(249d) Using a procedure similar to the reaction 3c, the esters from reaction 249c (0.12 g, 0.5 mmol) were hydrolyzed to give a mixture of indane acids (0.07 g, 61%). MS Found: (M+Na)$^+$=251.

(249e) Following a procedure similar to the synthesis of Example 2, the acids from reaction 249d (32 mg, 0.14 mmol) were reacted with 2-amino-4-(4-(pyridin-4-yl)benzyl)thiazole and purified by reverse-phase HPLC (70-100% solvent B gradient) to give the first eluding isomer as Example 249 (6.6 mg, 10%) and the second eluding isomer as Example 250 (10.7 mg, 16%). Both MS Found: (M+H)$^+$=478.

Example 251

(1S,2R)-6-cyano-2-methyl-1-(3-(methyloxy)phenyl)-N-1,3-thiazol-2-yl-2,3-dihydro-1H-indene-2-carboxamide

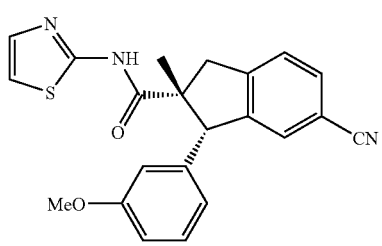

(251a) Using conditions similar to reactions 20a-e, ethyl (4-iodobenzoyl)acetate (9.58 g, 30.12 mmol) and 3-methoxybenzaldehyde (4.31 g, 1.05 eq) were reacted and purified by preparative reverse-phase HPLC (90-100% solvent B gradient) to give the cis-6-iodo-1-(3-methoxyphenyl)-2-methyl-2,3-dihydro-1H-indane-2-carboxylic acid (1.68 g, 14%) and the trans isomer (0.43 g). The cis isomer was resolved by preparative chiral SFC-HPLC(OJ column, 30×250 mm, 15% MeOH/85% $CO_2$) to give the fast enantiomer (636 mg) and the slow enantiomer (640 mg). MS Found for both: $(M+Na)^+$=431.

(251b) Using a procedure similar to Example 85, the slow enantiomer from the reaction 251a (398 mg, 0.97 mmol) was reacted with CuCN (353 mg, 5.6 eq) to give the desired cyano acid (179 mg, 60%).

(251c) Following a procedure similar to the synthesis of Example 2, the acid from reaction 251b (89.7 mg, 0.29 mmol) was reacted with 2-aminothiazole and purified by preparative reverse-phase HPLC (70-85% solvent B gradient) to give Example 251 (109.6 mg, 96%). MS Found: $(M+H)^+$=390.

Example 252

(1S,2R)-6-cyano-2-methyl-1-(3-(methyloxy)phenyl)-N-1,3,4-thiadiazol-2-yl-2,3-dihydro-1H-indene-2-carboxamide

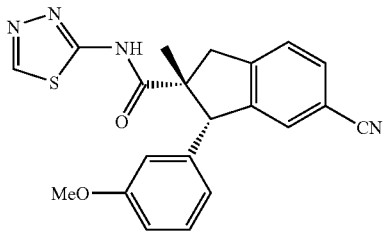

Following a procedure similar to the synthesis of Example 2, the acid from reaction 251b (89.7 mg, 0.29 mmol) was reacted with 2-amino-1,3,4-thiadiazole and purified by preparative reverse-phase HPLC (70-80% solvent B gradient) to give Example 252 (96.5 mg, 85%). MS Found: $(M+H)^+$=391.

Example 253 rac-(1R,2S)-1-(3-chlorophenyl)-6-cyano-2-methyl-N-1,3-thiazol-2-yl-2,3-dihydro-1H-indene-2-carboxamide

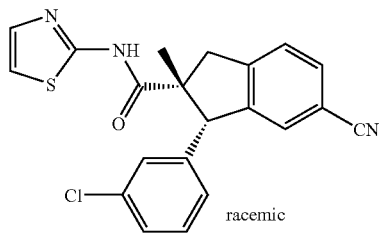

(253a) Using conditions similar to reactions 20a-e, ethyl (4-iodobenzoyl)acetate (9.6 g, 30.18 mmol) and 3-bromobenzaldehyde (6.03 g, 1.08 eq) were reacted and purified by preparative reverse-phase HPLC (95-100% solvent B gradient) to give the cis-6-iodo-1-(3-bromophenyl)-2-methyl-2,3-dihydro-1H-indane-2-carboxylic acid (1.38 g, 10%) and the trans isomer (3.44 g). MS Found for both: $(M+Na)^+$=479, 481.

(253b) Following a procedure similar to the preparation of Example 85 except that the microwave reaction was run at 180° C. for 30 min, the cis acid from 253a (94 mg, 0.206 mmol) was converted to bromo cyano acid and dicyano acid. Then following a procedure similar to the preparation of Example 157, the bromo cyano acid in the mixture was reacted with CuCl and purified by preparative reverse-phase HPLC (70-90% solvent B gradient) to give the chloro cyano acid (17 mg, 27%). MS Found: $(M+H)^+$=312.

(253c) Following a procedure similar to the synthesis of Example 2, the chloro cyano acid from reaction 253b (10.3 mg, 0.033 mmol) was reacted with 2-aminothiazole and purified by preparative reverse-phase HPLC (80-95% solvent B gradient) to give Example 253 (11.5 mg, 88%). MS Found: $(M+H)^+$=394.

Example 254 rac-(1R,2S)-1-(3-chlorophenyl)-6-cyano-2-methyl-N-1,3,4-thiadiazol-2-yl-2,3-dihydro-1H-indene-2-carboxamide

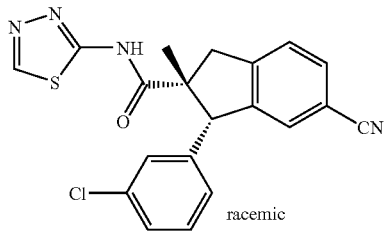

Following a procedure similar to the synthesis of Example 2, the acid from reaction 253b (13.6 mg, 0.044 mmol) was reacted with 2-amino-1,3,4-thiadiazole and purified by preparative reverse-phase HPLC (70-85% solvent B gradient) to give Example 254 (9.7 mg, 56%). MS Found: $(M+H)^+$=395.

Example 255 rac-(1R,2S)-6-cyano-2-methyl-1-(3-methylphenyl)-N-1,3-thiazol-2-yl-2,3-dihydro-1H-indene-2-carboxamide

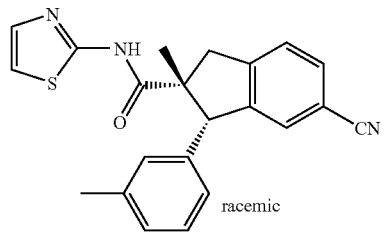

(255a) Following a procedure similar to reaction 179c, the keto ester from reaction 194b (4 g, 14.1 mmol) was reacted with 3-tolylmagnesium bromide to give the alcohol (4.16 g, 78%).

(255b) Following a procedure similar to reaction 179d, the alcohol from reaction 255a was reduced to a mixture of cis and trans indane esters.

(255c) Following a procedure similar to reaction 179f, the esters from reaction 255b was hydrolyzed to give the bromo acids.

(255d) Following a procedure similar to the preparation of Example 85, the bromo acids from reaction 255c was converted to the cyano acids and separated by preparative reverse-phase HPLC (75-90% solvent B gradient) to give cis cyano acid (280 mg, 21% for 3 steps) and trans cyano acid (426 mg, 32% for 3 steps). MS Found for both: $(M+H)^+=292$.

(255e) Following a procedure similar to the preparation of Example 2, the cis cyano acid from reaction 255d (12.9 mg, 0.044 mmol) was reacted with 2-aminothiazole to give Example 255 (13.3 mg, 81%). MS Found: $(M+H)^+=374$.

Example 256 rac-(1R,2S)-6-cyano-2-methyl-1-(3-methylphenyl)-N-1,3,4-thiadiazol-2-yl-2,3-dihydro-1H-indene-2-carboxamide

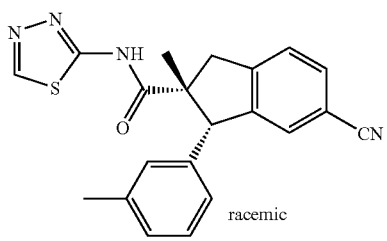

Following a procedure similar to the synthesis of Example 2, the acid from reaction 255d (13.5 mg, 0.046 mmol) was reacted with 2-amino-1,3,4-thiadiazole to give Example 256 (12.6 mg, 72%). MS Found: $(M+H)^+=375$.

Example 257 rac-(1R,2S)-6-cyano-2-methyl-1-(4-(methyloxy)phenyl)-N-1,3-thiazol-2-yl-2,3-dihydro-1H-indene-2-carboxamide

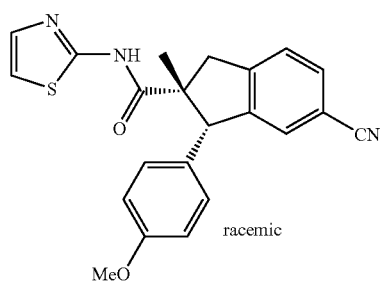

(257a) Following a procedure similar to reaction 179c, the keto ester from reaction 194b (4.2 g, 14.8 mmol) was reacted with 4-methoxymagnesium bromide to give the alcohol (4.88 g, 84%).

(257b) Following a procedure similar to reaction 179d, the alcohol from reaction 257a was reduced to a mixture of cis and trans indane esters.

(257c) Following a procedure similar to reaction 179, the esters from reaction 257b was hydrolyzed to give the bromo acids.

(257d) The bromo acids from reaction 257c was separated by preparative reverse-phase HPLC (85-100% solvent B gradient) to give the cis bromo acid (580 mg, 14% for 2 steps) and trans bromo acid (1.95 g, 46% for 2 steps).

(257e) Following a procedure similar to the preparation of Example 85, the cis bromo acid from reaction 257d (306.8 mg, 0.85 mmol) was converted to the cis cyano acid (139.6 mg, 54%). MS Found: $(M+H)^+=308$.

(257f) Following a procedure similar to the preparation of Example 2, the cis cyano acid from reaction 257e (10 mg, 0.033 mmol) was reacted with 2-aminothiazole to give Example 257 (7.9 mg, 62%). MS Found: $(M+H)^+=390$.

Example 258 rac-(1R,2S)-6-cyano-2-methyl-1-(4-(methyloxy)phenyl)-N-1,3,4-thiadiazol-2-yl-2,3-dihydro-1H-indene-2-carboxamide

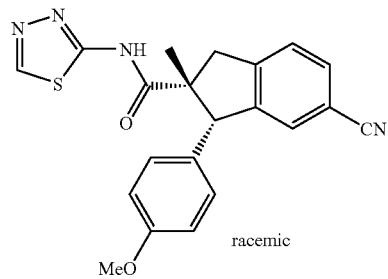

Following a procedure similar to the synthesis of Example 2, the acid from reaction 257e (12.4 mg, 0.04 mmol) was reacted with 2-amino-1,3,4-thiadiazole to give Example 258 (9.5 mg, 60%). MS Found: $(M+H)^+=391$.

Example 259 rac-(1R,2S)-1-(4-bromophenyl)-2-methyl-6-(methyloxy)-N-1,3-thiazol-2-yl-2,3-dihydro-1H-indene-2-carboxamide

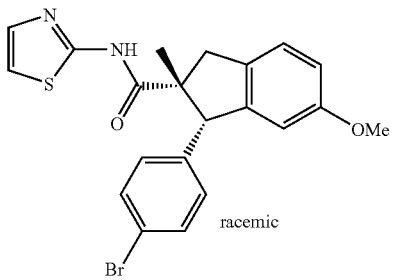

(259a-e) Using conditions similar to reactions 20a-e, ethyl (4-methoxybenzoyl)acetate (25 g, 112.49 mmol) and 4-bromobenzaldehyde (20.89 g, 1 eq) were reacted to give the bromo acid (25.98 g, 64% for 5 steps). MS Found: $(M+H)^+=383, 385$.

(259f) Following a procedure similar to the preparation of Example 2, the bromo acid from reaction 259e (5 g, 13.84 mmol) was reacted with 2-aminothiazole to give Example 259 (4.94 g, 80%). MS Found: $(M+H)^+=443, 445$.

Example 260 rac-(1R,2S)-1-(4-bromophenyl)-6-hydroxy-2-methyl-N-1,3-thiazol-2-yl-2,3-dihydro-1H-indene-2-carboxamide

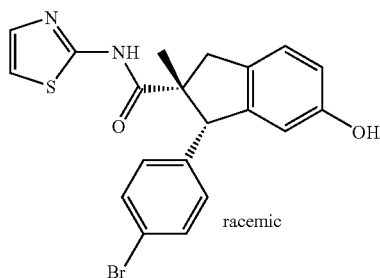

racemic

Following a procedure similar to the preparation of Example 5, Example 259 was converted to Example 260. MS Found: (M+H)⁺=429, 431.

Example 261 rac-(1R,2S)-1-(4-bromophenyl)-2-methyl-6-(methyloxy)-N-1,3,4-thiadiazol-2-yl-2,3-dihydro-1H-indene-2-carboxamide

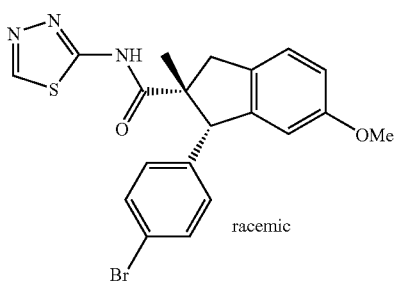

racemic

Following a procedure similar to the synthesis of Example 2, the acid from reaction 259e (6 g, 16.6 mmol) was reacted with 2-amino-1,3,4-thiadiazole to give Example 261 (4.21 g, 57%). MS Found: (M+H)⁺=444, 446.

Example 262 rac-(1R,2S)-1-(4-bromophenyl)-6-cyano-2-methyl-N-1,3-thiazol-2-yl-2,3-dihydro-1H-indene-2-carboxamide

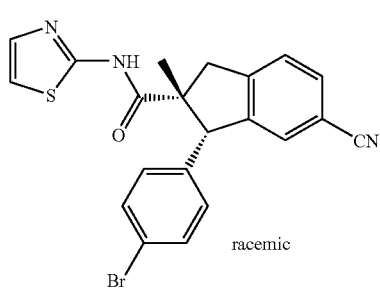

racemic (262a) A CH₂Cl₂ (20 mL) solution of Example 260 (313 mg, 0.73 mmol), 2-[N,N-bis(trifluoromethylsulfonyl)amino]pyridine (2.98 g, 7 eq) and triethylamine (3.4 mL) was stirred at room temperature overnight. The mixture was concentrated, dissolved in ethyl acetate (50 mL), washed with 1 N HCl (10 mL) and brine (50 mL) and concentrated. The resulting solid was triturated with CH₂Cl₂ (50 mL) and filtered. The filtrate was concentrated and purified by silica gel column (ISCO 40 g cartridge, 10 to 50% ethyl acetate-hexanes) to give the bromo triflate (405 mg, 99%). MS Found: (M+H)⁺=561, 563.

(262b) A DMF (1 mL) solution of the triflate from reaction 262a (53.7 mg, 0.096 mmol), Pd₂(dba)₃ (10 mg, 0.11 eq), dppf (12.5 mg, 0.24 eq) and KCN (6.7 mg, 1.1 eq) was purged with argon for 10 min. The mixture was put in a sealed-tube and heated at 80° C. overnight. After cooling to room temperature, the mixture was poured into ethyl acetate (20 mL) and saturated NH₄Cl (10 mL). The organic layer was separated, washed with brine (10 mL), dried (MgSO₄), concentrated and purified by silica gel column (ISCO 12 g cartridge, 0 to 50% ethyl acetate-hexanes). Further purification with preparative reverse-phase HPLC (80-100% solvent B gradient) gave Example 262 (14.3 mg, 34%). MS Found: (M+H)⁺=438, 440.

Example 263 rac-(1R,2S)-1-(4-bromophenyl)-6-hydroxy-2-methyl-N-1,3,4-thiadiazol-2-yl-2,3-dihydro-1H-indene-2-carboxamide

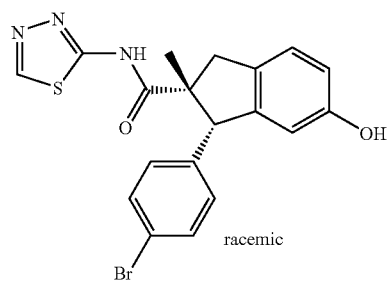

racemic

Following a procedure similar to the preparation of Example 5, Example 261 was converted to Example 263. MS Found: (M+H)⁺=430, 432.

Example 264 rac-(1R,2S)-1-(4-chlorophenyl)-6-cyano-2-methyl-N-1,3-thiazol-2-yl-2,3-dihydro-1H-indene-2-carboxamide

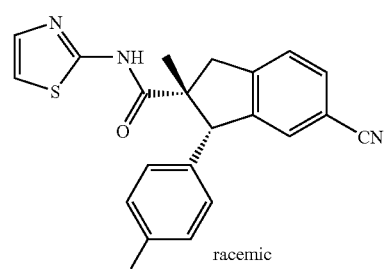

racemic

Following a procedure similar to the preparation of Example 157, Example 262 (21.8 mg, 0.05 mmol) was converted to Example 264 (11 mg, 56%). MS Found: (M+H)⁺=394.

Example 265 rac-(1R,2S)-6-cyano-1-(4-cyanophenyl)-2-methyl-N-1,3-thiazol-2-yl-2,3-dihydro-1H-indene-2-carboxamide

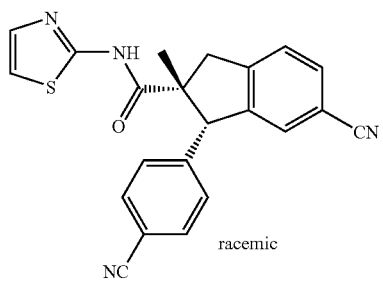
racemic

Following a procedure similar to the preparation of Example 85, Example 262 (22 mg, 0.05 mmol) was converted to Example 265 (7 mg, 36%). MS Found: (M+H)$^+$=385.

Example 266 rac-(1R,2S)-6-cyano-1-(4-cyanophenyl)-2-methyl-N-1,3,4-thiadiazol-2-yl-2,3-dihydro-1H-indene-2-carboxamide

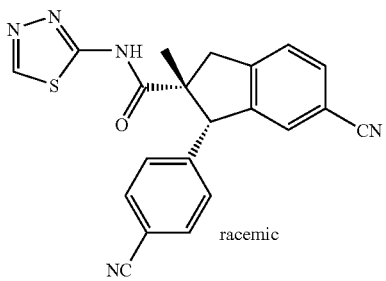
racemic (266a) Following a procedure similar to the reaction 262a, Example 263 (3.65 g, 8.48 mmol) was converted to the bromo triflate (3.83 g, 80%). MS Found: (M+H)$^+$=562, 564.

(266b) Following a procedure similar to the reaction 262b, the bromo triflate from reaction 266a (61 mg, 0.109 mmol) was converted to Example 266 (8.7 mg, 21%). MS Found: (M+H)$^+$=386.

Example 267 rac-(1R,2S)-1-(4-bromophenyl)-6-cyano-2-methyl-N-1,3,4-thiadiazol-2-yl-2,3-dihydro-1H-indene-2-carboxamide

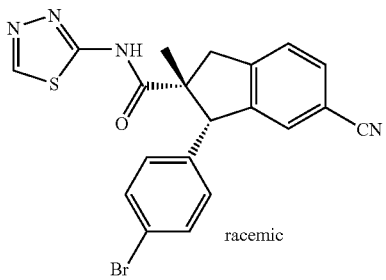
racemic

Following a procedure similar to the reaction 262b, the triflate from reaction 266a (67 mg, 0.119 mmol) was converted to Example 267 (5.1 mg, 10%). MS Found: (M+H)$^+$=439, 441.

Examples 268 and 269

(1S,2R)-6-cyano-2-methyl-1-(5-methyl-2-thienyl)-N-1,3,4-thiadiazol-2-yl-2,3-dihydro-1H-indene-2-carboxamide and (1R,2S)-6-cyano-2-methyl-1-(5-methyl-2-thienyl)-N-1,3,4-thiadiazol-2-yl-2,3-dihydro-1H-indene-2-carboxamide

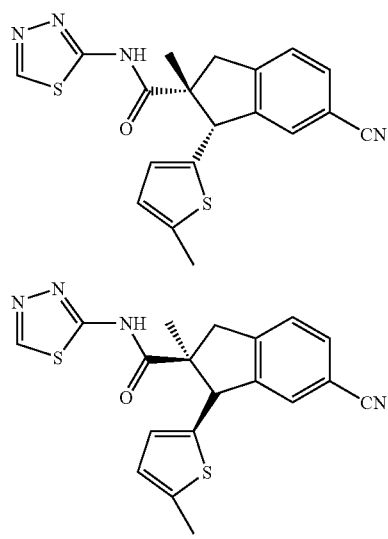

Example 213 (16.6 mg) was separated by preparative chiral HPLC (Chiralcel OD column, 30×250 mm, 7.5% EtOH-7.5% MeOH—85% Heptane, 20 mL/min) to give the fast eluding enantiomer as Example 268 (3.2 mg) and the slow eluding enantiomer as Example 269 (3.8 mg). Both MS Found: (M+H)$^+$=381.

Examples 270 and 271

(1S,2R)-1-(3-chlorophenyl)-6-cyano-2-methyl-N-1,3,4-thiadiazol-2-yl-2,3-dihydro-1H-indene-2-carboxamide and (1R,2S)-1-(3-chlorophenyl)-6-cyano-2-methyl-N-1,3,4-thiadiazol-2-yl-2,3-dihydro-1H-indene-2-carboxamide

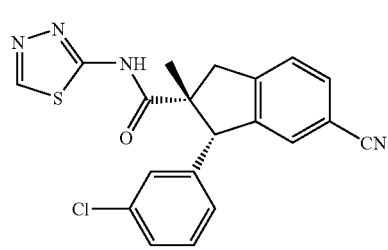

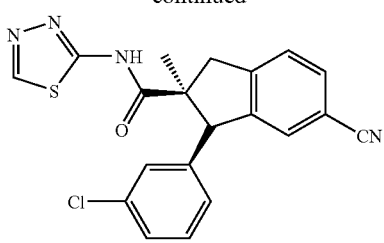

Example 254 (31.5 mg) was separated by preparative chiral HPLC (Chiralcel OD column, 30×250 mm, 7.5% EtOH-7.5% MeOH—85% Heptane, 18 mL/min) to give the fast eluding enantiomer as Example 270 (4.9 mg) and the slow eluding enantiomer as Example 271 (6.0 mg). Both MS Found: (M+H)$^+$=395.

Example 272

(1S,2R)-6-(4-((dimethylamino)carbonyl)phenyl)-2-methyl-1-phenyl-N-1,3-thiazol-2-yl-2,3-dihydro-1H-indene-2-carboxamide

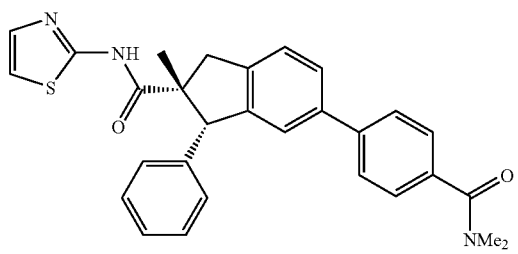

(272a) The racemate acid from the reaction 20e (34 g) was separated by preparative chiral SFC-HPLC (Chiralcel OJ column, 4.6×250 mm, 5 µparticle size, 35° C., 4 mL/min 10% MeOH—CO$_2$) to give the fast enantiomer (15.88 g) and the slow enantiomer (11.86 g).

(272b) Using a procedure similar to the synthesis of Example 2, the slow enantiomer acid from the reaction 272a (8 g, 28.3 mmol) was reacted with 2-aminothiazole to give the methoxy amide (9.96 g, 96%). MS Found: (M+H)$^+$=365.

(272c) Using a procedure similar to the synthesis of Example 5, the methoxy amide from the reaction 272b (9.96 g, 27.3 mmol) was converted to phenol amide. MS Found: (M+H)$^+$=351.

(272d) Following a procedure similar to the reaction 262a, the phenol amide from the reaction 272c was converted to the triflate. MS Found: (M+H)$^+$=483.

(272e) Following a procedure similar to the preparation of Example 77, the triflate from the reaction 272d (29.5 mg, 0.061 mmol) was coupled with 4-(N,N-dimethylaminocarbonyl)phenyl boronic acid (37.8 mg, 3.2 eq) to give Example 272 (22.1 mg, 75%). MS Found: (M+H)$^+$=482.

Example 273 rac-4'-((1R,2S)-6-hydroxy-2-methyl-2-((4,3-thiazol-2-ylamino)carbonyl)-2,3-dihydro-1H-inden-1-yl)-N,N-dimethyl-4-biphenylcarboxamide

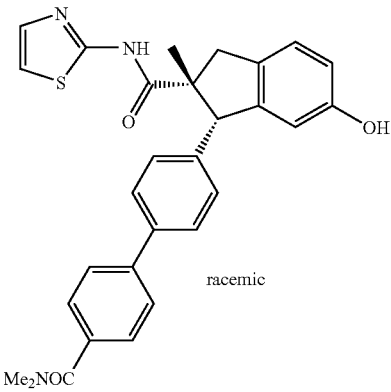

Following a procedure similar to the preparation of Example 77, Example 260 (101.5 mg, 0.236 mmol) was coupled with 4-(N,N-dimethylaminocarbonyl)phenyl boronic acid (92.2 mg, 2 eq) to give the Example 273 (57.3 mg, 49%). MS Found: (M+H)$^+$=498.

Example 274 rac-(1R,2S)-5-(4-((dimethylamino)carbonyl)phenyl)-2-methyl-1-phenyl-N-1,3-thiazol-2-yl-2,3-dihydro-1H-indene-2-carboxamide

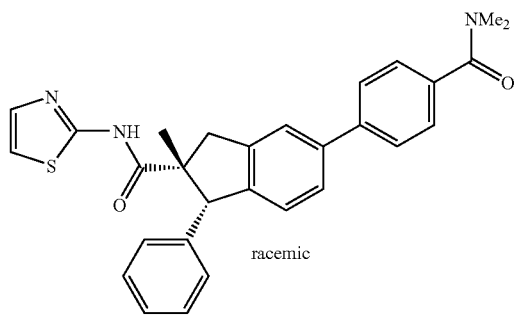

(274a) Following a procedure similar to the reaction 262a, Example 36 (23.5 mg, 0.067 mmol) was converted to the triflate (24.2 mg, 75%). MS Found: (M+H)$^+$=483.

(274b) Following a procedure similar to the preparation of Example 77, the triflate from the reaction 274a (24 mg, 0.05 mmol) was coupled with 4-(N,N-dimethylaminocarbonyl) phenyl boronic acid (25.3 mg, 2.6 eq) to give the Example 274 (5.9 mg, 25%). MS Found: (M+H)$^+$=482.

Example 275 rac-4'((1S,2R)-6-cyano-2-methyl-2-((1,3-thiazol-2-ylamino)carbonyl)-2,3-dihydro-1H-inden-1-yl)-N,N-dimethyl-4-biphenylcarboxamide

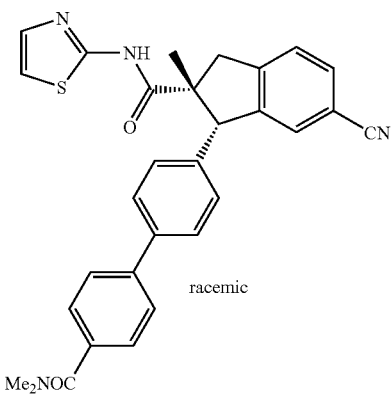

(275a) Following a procedure similar to the reaction 262a, Example 273 (54.7 mg, 0.11 mmol) was converted to the triflate (60.3 mg, 87%). MS Found: (M+H)$^+$=630.

(275b) Following a procedure similar to the reaction 262b, the triflate from the reaction 275a (60.3 mg, 0.096 mmol) was converted to Example 275 (41.5 mg, 86%). MS Found: (M+H)$^+$=507.

Examples 276 and 277

(1S,2R)-6-cyano-N-((1R,2R)-2-hydroxycyclopentyl)-2-methyl-1-phenyl-2,3-dihydro-1H-indene-2-carboxamide and (1S,2R)-6-cyano-N-((1S,2S)-2-hydroxycyclopentyl)-2-methyl-1-phenyl-2,3-dihydro-1H-indene-2-carboxamide

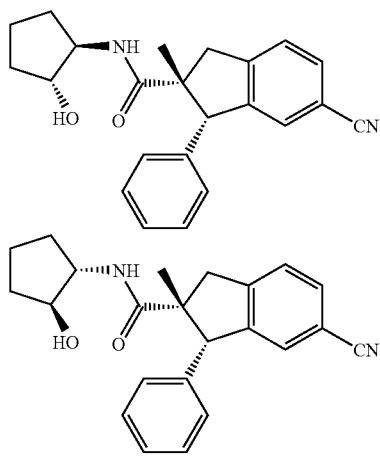

Following a procedure similar to the synthesis of Example 2, the chiral acid from reaction 90b (81 mg, 0.292 mmol) was reacted with trans-2-aminocyclopentanol HCl salt (36 mg, 1.2 eq). The product mixture was separated by preparative reverse-phase HPLC (40-60% solvent B gradient) to give the fast diastereomer as Example 276 (16.9 mg) and the slow diastereomer as Example 277 (16.1 mg). MS Found for both: (M+H)$^+$=361.

What is claimed is:

1. A compound according to formula (IA):

$$\text{(IA)}$$

or an enantiomer, diastereomer, or a pharmaceutically-acceptable salt thereof, in which:
  $R_1$, $R_2$, $R_3$, and $R_4$ are independently selected from hydrogen, cyano, hydroxy, alkoxy, phenyl or substituted phenyl;
  X is -$A_1QA_2$-;
  Q is —C(=O)N$R_5$—;
  $A_1$ and $A_2$ are independently selected from a bond, $C_{1-3}$alkylene, $C_{1-3}$alkylene substituted with halogen or hydroxyl;
  $R_5$ is hydrogen;
  $R_7$ is alkyl or substituted alkyl;
  $R_8$ is phenyl;
  $R_9$ is H or alkyl;
  $R_{10}$, and $R_{11}$ are each H;
  Y is selected from phenyl, $C_{1-6}$alkyl, substituted $C_{1-6}$alkyl, and heteroaryl which is imidazolyl, thiazolyl or thienyl.

2. A compound according to claim 1, or an enantiomer, diastereomer, or a pharmaceutically-acceptable salt thereof, in which $A_1$ and $A_2$ are independently selected from a bond, methylene, and methylene substituted with hydroxy or fluoro.

3. A compound according to claim 1, or enantiomers, diastereomers, or a pharmaceutically-acceptable salt, thereof, wherein $R_7$ is alkyl.

4. A compound according to claim 3, or an enantiomer, diastereomer, or a pharmaceutically-acceptable salt thereof, wherein
  $R_7$ is $C_{1-6}$alkyl.

5. A compound according to claim 1 or enantiomers, diastereomers, or a pharmaceutically-acceptable salt thereof, wherein X is —C(=O)N$R_5$ having the carbon atom attached to Y.

6. A compound according to claim 5, or enantiomers, diastereomers, or a pharmaceutically-acceptable salt thereof, wherein Y is selected from imidazole, thienyl or thiazole.

7. A compound according to claim 1, or enantiomers, diastereomers, or a pharmaceutically-acceptable salt thereof, wherein:
  $A_1$ and $A_2$ are independently a bond, methylene, or methylene substituted with hydroxy or fluoro; and
  Y is
  (i) methyl, ethyl, or $CF_3$; or
  (ii) a phenyl, thienyl, thiazolyl, or imidazolinyl.

8. A compound selected from the following:
  (i) rac-(1R,2R)-1-methyl-N-(4-((4-(methyloxy)phenyl)methyl)-1H-imidazol-2-yl)-1-phenyl-2,3-dihydro-1H-indene-2-carboxamide;
  rac-(1R,2S)—N-1H-imidazol-2-yl-2-methyl-6-(methyloxy)-1-phenyl-2,3-dihydro-1H-indene-2-carboxamide;
  rac-(1R,2S)-6-hydroxy-N-1H-imidazol-2-yl-2-methyl-1-phenyl-2,3-dihydro-1H-indene-2-carboxamide;
  rac-2-(((1R,2S)-6-hydroxy-2-methyl-1-phenyl-2,3-dihydro-1H-inden-2-yl)carbonyl)hydrazinecarboxamide;

rac-5-(((1R,2S)-2-methyl-6-(methyloxy)-1-phenyl-2,3-dihydro-1H-inden-2-yl)-2,4-dihydro-3H-1,2,4-triazol-3-one;
rac-((1R,2S)-6-bromo-2-methyl-1-phenyl-2,3-dihydro-1H-inden-2-yl)methanol;
rac-(1R,2S)-6-cyano-2-methyl-N-(methylsulfonyl)-1-phenyl-2,3-dihydro-1H-indene-2-carboxamide;
rac-(1R,2S)-6-cyano-2-methyl-1-phenyl-N-(phenylsulfonyl)-2,3-dihydro-1H-indene-2-carboxamide;
((1R,2S)-6-cyano-2-methyl-1-phenyl-2,3-dihydro-1H-inden-2-yl)methyl rac-phenylcarbamate;
rac-(2R,3S)-2-((R)-hydroxy(2-thienyl)methyl)-2-methyl-3-phenyl-2,3-dihydro-1H-indene-5-carbonitrile;
(2R,3S)-2-((S)-hydroxy(2-thienyl)methyl)-2-methyl-3-phenyl-2,3-dihydro-1H-indene-5-carbonitrile;
rac-(2R,3S)-2-methyl-3-phenyl-2-(2-thienylcarbonyl)-2,3-dihydro-1H-indene-5-carbonitrile;
rac-(2R,3S)-2-((R)-hydroxy(3-thienyl)methyl)-2-methyl-3-phenyl-2,3-dihydro-1H-indene-5-carbonitrile;
(2R,3S)-2-((S)-hydroxy(3-thienyl)methyl)-2-methyl-3-phenyl-2,3-dihydro-1H-indene-5-carbonitrile;
rac-(2R,3S)-2-methyl-3-phenyl-2-(3-thienylcarbonyl)-2,3-dihydro-1H-indene-5-carbonitrile;
rac-(2R,3S)-2-[((4R)-2,5-dioxo-4-imidazolidinyl)-2-methyl-3-phenyl-2,3-dihydro-1H-indene-5-carbonitrile;
(2R,3S)-2-((4S)-2,5-dioxo-4-imidazolidinyl)-2-methyl-3-phenyl-2,3-dihydro-1H-indene-5-carbonitrile;
rac-(2R,3S)-2-methyl-3-phenyl-2-(1H-pyrazol-5-yl)-2,3-dihydro-1H-indene-5-carbonitrile;
rac-(2R,3S)-2-(3-aminoimidazo[1,2-a]pyridin-2-yl)-2-methyl-3-phenyl-2,3-dihydro-1H-indene-5-carbonitrile;
methyl rac-(2E)-3-((1R,2R)-6-cyano-2-methyl-1-phenyl-2,3-dihydro-1H-inden-2-yl)-2-propenoate;
Nrac-N-((1R,2S)-6-cyano-2-methyl-1-phenyl-2,3-dihydro-1H-inden-2-yl)-2-thiophenecarboxamide;
rac-N-((1R,2S)-6-cyano-2-methyl-1-phenyl-2,3-dihydro-1H-inden-2-yl)-2-(2-thienyl)acetamide;
rac-1-((1R,2S)-6-cyano-2-methyl-1-phenyl-2,3-dihydro-1H-inden-2-yl)-3-phenylurea;
rac-N-(((1R,2S)-6-cyano-2-methyl-1-phenyl-2,3-dihydro-1H-inden-2-yl)methyl)acetamide;
rac-N-(((1R,2S)-6-cyano-2-methyl-1-phenyl-2,3-dihydro-1H-inden-2-yl)methyl)-2,2,2-trifluoroacetamide;
rac-N-((1R,2S)-6-cyano-2-methyl-1-phenyl-2,3-dihydro-1H-inden-2-yl)methanesulfonamide;
rac-N-((1R,2S)-6-cyano-2-methyl-1-phenyl-2,3-dihydro-1H-inden-2-yl)-2,2,2-trifluoroacetamide;
(1S,2R)-6-cyano-N-ethyl-2-methyl-1-phenyl-2,3-dihydro-1H-indene-2-carboxamide;
(1S,2R)-6-cyano-N,N,2-trimethyl-1-phenyl-2,3-dihydro-1H-indene-2-carboxamide;
rac-N-((1R,2S)-6-cyano-2-methyl-1-phenyl-2,3-dihydro-1H-inden-2-yl)-2,2,3,3,3-pentafluoropropanamide;
rac-2-((1R,2S)-6-bromo-2-methyl-1-phenyl-2,3-dihydro-1H-inden-2-yl)-1,3-benzothiazole;
rac-2-((1R,2S)-6-bromo-2-methyl-1-phenyl-2,3-dihydro-1H-inden-2-yl)-1H-benzimidazole;
rac-2-((1R,2S)-6-bromo-2-methyl-1-phenyl-2,3-dihydro-1H-inden-2-yl)-3H-imidazo[4,5-b]pyridine;
(1S,2R)-6-cyano-N-((1R,2R)-2-hydroxycyclopentyl)-2-methyl-1-phenyl-2,3-dihydro-1H-indene-2-carboxamide; or
(1S,2R)-6-cyano-N-((1S,2S)-2-hydroxycyclopentyl)-2-methyl-1-phenyl-2,3-dihydro-1H-indene-2-carboxamide; or (ii) an enantiomer, diastereomer, or a pharmaceutically-acceptable salt of (i), thereof.

9. A pharmaceutical composition comprising a compound as defined in claim 1 and a pharmaceutically acceptable carrier therefor.

10. A compound of the structure

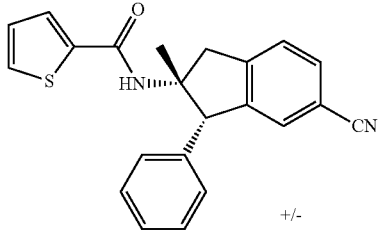

or a pharmaceutically acceptable salt thereof.

* * * * *

UNITED STATES PATENT AND TRADEMARK OFFICE
CERTIFICATE OF CORRECTION

PATENT NO. : 8,324,401 B2
APPLICATION NO. : 12/542762
DATED : December 4, 2012
INVENTOR(S) : Jingwu Duan et al.

It is certified that error appears in the above-identified patent and that said Letters Patent is hereby corrected as shown below:

In the Claims:

Claim 4:

Column 150, line 41, change "$R_7$ is $C_{1-6}$alkyl." to

-- $R_7$ is $C_{1-6}$alkyl;
$R_9$ is hydrogen. --.

Signed and Sealed this
Fourteenth Day of May, 2013

Teresa Stanek Rea
*Acting Director of the United States Patent and Trademark Office*